US007268232B2

(12) United States Patent
Schlienger et al.

(10) Patent No.: US 7,268,232 B2
(45) Date of Patent: Sep. 11, 2007

(54) ANDROGEN RECEPTOR MODULATORS AND METHOD OF TREATING DISEASE USING THE SAME

(75) Inventors: Nathalie Schlienger, Frederiksberg (DK); Jan Pawlas, Frederiksberg (DK); Alma Fejzic, Copenhagen S (DK); Roger Olsson, Bunkeflostrand (SE); Birgitte Winther Lund, Bagsvaerd (DK); Fabrizio Badalassi, Copenhagen K (DK); Rasmus Lewinsky, Herlev (DK); Mikkel Boas Thygesen, Copenhagen (DK)

(73) Assignee: Acadia Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 11/130,669

(22) Filed: May 16, 2005

(65) Prior Publication Data
US 2006/0014739 A1    Jan. 19, 2006

Related U.S. Application Data

(60) Provisional application No. 60/571,961, filed on May 17, 2004.

(51) Int. Cl.
*C07D 451/02* (2006.01)
*C07D 401/00* (2006.01)
*C07D 405/00* (2006.01)
*C07D 409/00* (2006.01)
*C07D 413/00* (2006.01)

(52) U.S. Cl. .................. 546/124; 546/126; 544/127
(58) Field of Classification Search ............ 546/124, 546/126; 544/127
See application file for complete search history.

(56) References Cited

U.S. PATENT DOCUMENTS

| 5,707,798 A | 1/1998 | Brann |
| 6,670,386 B2 | 12/2003 | Sun et al. |
| 2004/0181064 A1 | 9/2004 | Sun et al. |

FOREIGN PATENT DOCUMENTS

| EP | 1553 074 A1 | 7/2005 |
| WO | 308 897 A | 3/1989 |
| WO | WO 2003/011824 A | 2/2003 |
| WO | WO 2003/096980 A | 11/2003 |
| WO | WO 2004/016576 A | 2/2004 |
| WO | 2005/090282 * | 9/2005 |

OTHER PUBLICATIONS

Kashman et al., Tetrahedron, "Circular dichroism of heterocyclohexan-4-onic systems-II", 1972, vol. 28, pp. 155-165.*
Alm et al., *Prog. Clin. Biol. Res.*, 312:447-58 (1989).
Alterman and Hallberg (*J. Org. Chem.*, 2000, 65, 7984-7989).
Antilla & Buchwald, *Org. Lett.*, 2001, 3, 2077-2079.
Arvela & Leadbeater, *J. Org. Chem*, 2003, 68, 9122-9125.
Bassilios et al, *Recueil.*, 1962, 81, 209-214.
"Bioreversible Carriers in Drug Design: Theory and Application", edited by E. B. Roche, Pergamon Press: New York, 14-21 (1987).
Brown & Reid, *J. Am. Chem. Soc.*, 1924, 46, 1838.
Buchwald et al, *J. Am. Chem. Soc.*, 2002, 124, 7421-7428.
Buchwald et al, *Org. Lett.*, 2002, 4, 581-584.
Bun-Hoi et al, *J. Org. Chem.*, 1951, 16, 988.
Bundgaard, H. et al., *J. Med. Chem.*, 32, 2503-2507 (1989).
Cacchi et al, *Org. Lett*, 2003, 5, 289-293.
Cacchi et al, *Org. Lett*, 2003, 5, 4269-4293.
Cakmak O. et al., *Collect. Czech. Chem. Commun.* 2000, 65, 1791-1804.
Consden & Kenyon, *J. Chem. Soc.*, 1935, 1591-1596.
Davies H. M. L. et al., *J. Org. Chem.* 1991, 56, 5696-5700.
Dewar et al., *J. Am. Chem. Soc.*, 1962, 84, 3541-3546.
Emerson & Walters, *J. Am. Chem. Soc.*, 1938, 60, 2023.
Fingl et al. 1975, in "The Pharmacological Basis of Therapeutics".
Frost & Wadsworth, *Chem. Commun.*, 2001, 22, 2316-2317.
G. Schiemann et al., *Ann.*, 1931, 487, 270-287.
Greene & Wuts, *Protective Groups in Organic Synthesis*, John Wiley & Sons, 1991.
Guthrie et al, *Can. J. Chem.*, 1993, 71, 2109-2122.
Hartwig, *Angew. Chem. Int. Ed.*, 1998, 37, 2046-2067.
Hartwig in *Modern Amination Methods*; Ricci, Ed.; Willey-VCH: Weinheim, Germany, 2000.
Hirst & Cohen, *J. Chem. Soc.*, 1895, 67, 830.
Joshi, A., *J. Ocul. Pharmacol.*, 10(1):29-45 (1994).
Klitgaard, N. et al., Acta Chem. Scand. 1970, 24, 33-42.
Kwong & Buchwald, *Org. Lett.*, 2003, 5, 793-796.
Kwong & Buchwald, *Org. Lett.*, 2002, 4, 3517-3520.
L. Paquette, ed., *Encyclopedia of Reagents for Organic Synthesis*, John Wiley and Sons, 1995.
Landini & Rocca, Synthesis, 1974, 565-566.
Li, *J. Org. Chem.*, 2002, 67, 3643-3650.
Mahfous, N.H. et al, *J. Pharm. Pharmacol.*, 53, 841-848 (2001).
Mayer et al., *Ophthamologica*, 210(2):101-3 (1996).
Milovic et al, *Synthesis*, 1991, 11, 1043-1045.
Mordenti, *Toxicol. Sci.*, 52(1):101-6 (1999).
Nigam & Weedon, *J. Chem. Soc.*, 1957, 200.
Olah & Kuhn, *Chem. Ber.* 1956, 89, 2211.
*Protective Groups in Organic Chemistry* (ed. J.F.W. McOmie, Plenum Press, 1973).
R. Larock, *Comprehensive Organic Transformations*, VCH Publishers, 1989.
Read, *J. Am. Chem. Soc.*, 1922, 44, 1746-1755.
*Remington's Pharmaceutical Sciences*, 18th Ed., Mack Publishing Co., Easton, PA (1990).

(Continued)

Primary Examiner—Margaret D. Seaman
Assistant Examiner—Niloofar Rahmani
(74) Attorney, Agent, or Firm—Wilson Sonsini Goodrich & Rosati

(57) ABSTRACT

Disclosed herein are bicycloaryl compounds of Formula (I) that selectively modulate nuclear receptors, preferably the androgen receptor, or a pharmaceutically acceptable salt, ester, amide, or prodrug thereof, and methods of treating disease comprising administering a compound of Formula (I) to a patient in need thereof.

10 Claims, 7 Drawing Sheets

OTHER PUBLICATIONS

Rice & Kohn, *J. Am. Chem. Soc.*, 1955, 77, 4052.
S. Sekiguchi et al., *J. Org. Chem.*, 1979, 44, 3921-3925.
Screttas and Micha-Screttas, *J. Org. Chem.*, 1978, 43, 1064-1071.
Shedden et al., *Clin. Ther.*, 23(3):440-50 (2001).
Sundermeier et al, *Angew. Chem. Int. ed.*, 2003, 42, 1661-1664.
T. Higuchi and V. Stella, in "Prodrugs as Novel Delivery Systems", vol. 14, A.C.S. Symposium Series, American Chemical Society (1975).
T. Wang et al., *Org. Lett.*, 2003, 5, 897-900.
Vogel, *J. Chem. Soc.*, 1948, 1809.
W. Adcock et al., *J. Am. Chem. Soc.*, 1967, 89, 386-390.
Wan et al, *J. Org. Chem.*, 202, 67, 6232-6235.
Whitmore and Lester, *J. Am. Chem. Soc.*, 1942, 64, 1247.
Whitmore et al, *J. Am. Chem. Soc.*, 1947, 69, 235-237.
Wolf, *Liebigs Ann. Chem.*, 1952, 576, 35.
Wolfe and Buchwald *Tetrahedron Lett.*, 1997, 37, 6359-6362.
Gooβen and Ghosh, *Angew. Chem. Int. Ed. Engl.*, 2001, 40, 3458-3460.
Yasukara et al, *J. Chem. Soc. Perkin Trans. 1*, 2000, 17, 2901-2902.
Yang & Buchwald, *J. Organometallic Chem.*, 1999, 576, 125-146.
Yang and Denny, *J. Org. Chem.*, 2002, 67, 8958-8961.
Yin & Buchwald, *J. Am. Chem. Soc.*, 2002, 124, 6043-6048.
International Search Report for corresponding PCT Application No. PCT/US2005/017143, mailed on Nov. 30, 2005.
International Written Opinion for corresponding PCT Application No. PCT/US2005/017143, mailed on Nov. 30, 2005.

* cited by examiner

Castrated rats treated daily (two week dosing)

ANDROGEN RECEPTOR MODULATORS AND METHOD OF TREATING DISEASE USING THE SAME

RELATED APPLICATIONS

This non-provisional patent application claims the benefit of the filing date of U.S. Provisional Patent Application Ser. No. 60/571,961, entitled "ANDROGEN RECEPTOR MODULATORS AND METHOD OF TREATING DISEASE USING THE SAME," and filed on May 17, 2004. The disclosure of the '961 application is incorporated by reference herein in its entirety, including any drawings.

BACKGROUND OF THE INVENTION

1. Field of the Invention

The present invention relates novel compounds and methods of using the same for medicinal use and/or to modulate androgen receptors.

2. Description of the Related Art

The androgen receptor (AR) belongs to the family of nuclear hormone receptors. Nuclear hormone receptors define a superfamily of ligand activated transcription factors. Members of this family are characterized by a number of modular domains: a zinc finger DNA binding domain (DBD) triggers the interaction of the receptor with specific response elements at the DNA site, a ligand binding domain (LBD) adjacent to the DBD, and two transcriptional activation domains AF-1 and AF-2, which are ligand-independent and ligand-dependent, respectively. Upon ligand binding to the receptor, a conformational change occurs within the LBD bringing the AF-2 domain in closer proximity and allowing for the recruitment of co-activators. Co-activators create a physical interaction between the nuclear hormone receptor and components of the transcriptional machinery, establishing transcriptional modulation of target genes.

The steroid sex hormones testosterone and the more potent dihydroxy testosterone (DHT) represent the AR endogenous ligands. Through activation of the receptor, these "male sex hormones" modulate a number of physiological processes most notably primary and secondary male characteristics.

Clinical situations in which levels of plasma testosterone are decreased, also known as hypogonadism, have been extensively studied. For instance, children suffering from such a condition exhibit a total absence of pubertal development. Delay in puberty leads to psychological problems, secondary to short stature and/or delay in the acquisition of secondary sexual characteristics and the reduction of bone mass. Moreover, several epidemiological studies have confirmed that plasma testosterone levels gradually decrease with aging. On average a quarter of men in their sixties display clinical hypogonadism. This condition is even more prevalent among male octogenarians where 50-80% of men in this age group clinically qualify for hypogonadism. Decreased testosterone plasma levels are also seen in aging women. Age-related hypogonadism is associated with an obvious impairment in the quality of life from physical manifestations (muscle, bone density loss) to psychological problems (mood disorders, cognition, decreased libido). This condition is referred to as "male menopause" or "andropause".

Current therapies rely on the use of testosterone and testosterone analogs. They are the treatment of choice in delayed male puberty, male fertility as well as endometriosis. Because of the strong anabolic effects of this class of steroid hormones, they have been therapeutically approved for restoring skeletal muscle mass in patients suffering from burns. A number of placebo controlled clinical studies have reported a therapeutic benefit to androgen agonism in aging men. In particular, reports have emerged demonstrating the benefit of testosterone replacement therapy in improving a number of aspects of age related hypogonadism such as bone density, anabolism, libido, mood disorders (lack of vigor, well being) and cognition, and in the ophthalmologic arena, in disorders such as dry eye. More recent studies have highlighted a correlation between decreasing testosterone levels and increased incidence of Alzheimer's disease.

Since oral preparations of testosterone and testosterone analogs are ineffective due to enhanced first-pass metabolism and hepatotoxicity, intramuscular injectable forms of long-acting esters have constituted the basis of testosterone replacement therapy. However, the large fluctuations of serum testosterone levels induced by these preparations cause unsatisfactory shifts of mood and sexual function in some men; combined with the frequent injections, this delivery mode is thus far from being ideal. In contrast, transdermal testosterone patches display more favorable pharmacokinetic properties and have proven to be an effective mode of delivery. Nevertheless, testosterone patch systems (especially scrotal patches) are hampered by the high rate of skin irritations. Recently, testosterone gels have gained approval. Gels are applied once daily on the skin in quantities large enough to deliver sufficient amounts of testosterone to restore normal hormonal values and correct the signs and symptoms of hypogonadism. However while being very effective, this mode of application raises matters of adequate and consistent delivery.

Finally, the use of such steroid replacement therapy is widely believed to yield increase in prostate size. This androgenic property of testosterone and testosterone analogs constitute an additional and significant risk for prostate cancer.

SUMMARY OF THE INVENTION

One aspect of the present invention provides compounds of the general Formula (I) that selectively modulate nuclear receptors, preferably the androgen receptor,

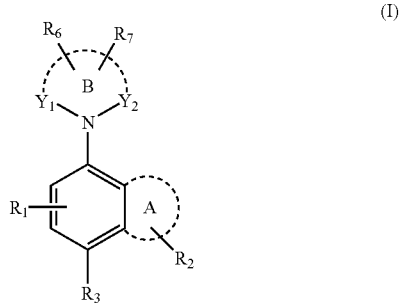

or a pharmaceutically acceptable salt, ester, amide, or prodrug thereof, wherein $R_1$ and $R_2$ are each independently selected from the group consisting of hydrogen, lower alkyl, alkenyl, alkynyl, halo, nitro, cyano, hydroxy, amino, lower aminoalkyl, lower alkoxy, aryl, heteroaryl, $COOR_4$, $CONR_4R_5$, $NHCOR_4$, $NHSO_2R_4$, $OCOR_4$, $COR_4$, $SR_4$, $S(O)_nR_8$, $SO_2NR_8R_9$;

$R_3$ is selected from the group consisting of cyano, nitro, $S(O)_nR_8$, $SO_2NR_8R_9$, $OSO_2R_4$, $P(O)(OR_4)(OR_5)$, $P(O)(OH)(NR_4R_5)$, $PO(NR_4R_5)_2$, $COOR_4$;

ring A is a 5- or 6-membered, optionally aromatic, partially saturated or completely saturated carbocycle or heterocycle, containing up to two heteroatoms or heterogroups selected from the group consisting of $NR_6R_7$, O, $SO_2$, S, C=O and C=S;

ring B is an optionally substituted monocyclic or bicyclic heterocycle, containing up to three heteroatoms or heterogroups, selected from the group consisting of $NR_6R_7$, O, $SO_2$, S, C=O and C=S;

$Y_1$ and $Y_2$ are $CR_6R_7$;

$R_4$ and $R_5$ are each independently selected from the group consisting of hydrogen, cyano, optionally substituted alkyl, optionally substituted alkenyl, optionally substituted alkynyl, optionally substituted cycloalkyl, optionally substituted heterocyclylalkyl, optionally substituted arylalkyl, optionally substituted aryl, optionally substituted heteroarylalkyl, optionally substituted heteroaryl;

$R_6$ and $R_7$ are each independently selected from the group consisting of hydrogen, halo, cyano, hydroxy, optionally substituted alkyl, optionally substituted alkenyl, optionally substituted alkynyl, optionally substituted cycloalkyl, optionally substituted heterocyclylalkyl, optionally substituted arylalkyl, optionally substituted aryl, optionally substituted heteroarylalkyl, optionally substituted heteroaryl, $OR_4$, $NR_4R_5$, $SR_4$, $COR_4$, $COOR_4$, $CONR_4R_5$, $NHCOR_4$, $OCOR_4$, $CSR_4$, $CSOR_4$, $CSNR_4R_5$, $NHCSR_4$, $OCSR_4$, $S(O)_nR_4$, $SO_2NR_4R_5$, $OSO_2R_4$, $NHSO_2R_4$;

$R_8$ and $R_9$ are each independently selected from the group consisting of hydrogen, optionally substituted alkyl, optionally substituted alkenyl, optionally substituted alkynyl, optionally substituted cycloalkyl, optionally substituted heterocyclylalkyl, optionally substituted arylalkyl, optionally substituted heteroarylalkyl; and n is an integer from 1 to 3.

In another aspect, the present invention relates to the administration of a compound of Formula (I) to a patient in order to treat a condition in the patient. In various embodiments, the condition treated includes hypogonadism, lower than normal testosterone plasma levels, infertility, sexual arousal disorder, sexual orgasmic disorders, disorders of libido, muscle wasting due to cachexia, HIV wasting, or critical illnesses, sarcopenia, frailty, short stature, dwarfism, bone density loss, mood disorders including lack of well being, lack of vigor, anger, irritability, sadness, tiredness, nervousness, depression, impaired cognitive functions including verbal fluency and spatial memory, neurodegenerative disorders, including Alzheimer's disease, Mild cognition impairment (MCI), Lewis body dementia, and frontal temporal dementia, xerophthalmia, metabolic disorders, including dyslipidemia, atherosclerosis, and non-insulin dependent diabetes (NIDDM), cardiovascular disorders including but not limited to hypertension, coronary artery disease, and myocardial perfusion, obesity, anemia, prostate cancer, and schizophrenia. In other embodiments, a compound of Formula (I) may be administered to a patient in order to prevent a condition in the patient. In various embodiments, the condition prevented includes bone density loss; xerophthalmia; metabolic disorders, including dyslipidemia, atherosclerosis, and non-insulin dependent diabetes (NIDDM); cardiovascular disorders including hypertension, coronary artery disease, and myocardial perfusion; obesity; and prostate cancer.

DETAILED DESCRIPTION OF THE PREFERRED EMBODIMENT

Figure 1:
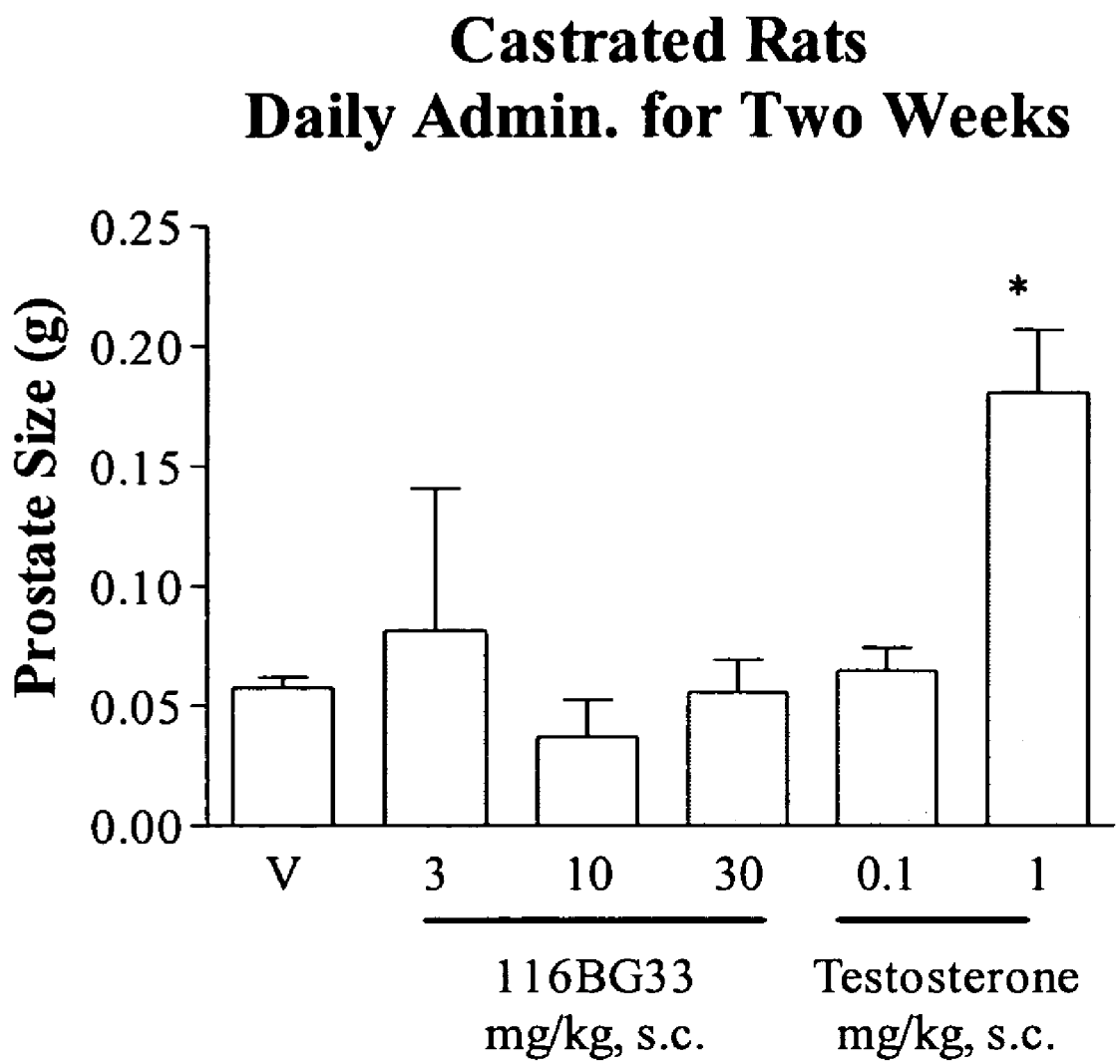
FIG. 1 shows the effect of daily subcutaneous administration for two weeks of 3, 10 or 30 mg/kg 116BG33 or 0.1 mg/kg testosterone propionate (TP) on wet weight of prostate.

Because of the undesirable adverse-effects of steroidal AR ligands, the search for Selective Androgen Receptor Modulators or SARMs has been initiated. This class of ligands demonstrate better pharmacokinetic and specificity profiles than the current steroidal therapies. In particular, non-steroidal SARMs display evident therapeutic benefit but lack androgenic properties. These adverse androgenic effects include manifestations such as prostate enlargement, acne, hirsutism, virilization and masculinization. Second generation SARMs contribute additional therapeutic benefits by displaying positive anabolic properties and antagonistic androgenic components. Another desirable feature of SARMs is significant bioavailabaility. In some embodiments, the SARMs are provided in a "once-a-day" dosing pill.

Thus, in a first aspect, the present invention provides compounds of the Formula (I) that selectively modulate nuclear receptors, preferably the androgen receptor,

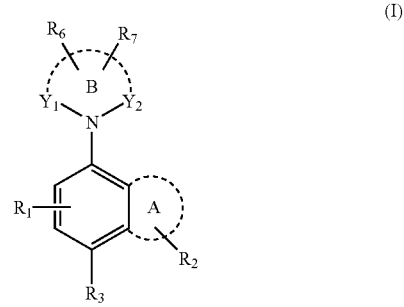

(I)

wherein $R_1$ and $R_2$ are each independently selected from the group consisting of hydrogen, lower alkyl, alkenyl, alkynyl, halo, nitro, cyano, hydroxy, amino, lower aminoalkyl, lower alkoxy, aryl, heteroaryl, $COOR_4$, $CONR_4R_5$, $NHCOR_4$, $NHSO_2R_4$, $OCOR_4$, $COR_4$, $SR_4$, $S(O)_nR_8$, $SO_2NR_8R_9$;

$R_3$ is selected from the group consisting of cyano, nitro, $S(O)_nR_8$, $SO_2NR_8R_9$, $OSO_2R_4$, $P(O)(OR_4)(OR_5)$, $P(O)(OH)(NR_4R_5)$, $PO(NR_4R_5)_2$, $COOR_4$;

ring A is a 5- or 6-membered, optionally aromatic, partially saturated or completely saturated carbocycle or heterocycle, containing up to two heteroatoms, selected from the group consisting of $NR_6R_7$, O, $SO_2$, S, C=O and C=S;

ring B is an optionally substituted monocyclic or bicyclic heterocycle, containing up to three heteroatoms or heterogroups, selected from the group consisting of $NR_6R_7$, O, $SO_2$, S, C=O and C=S;

$Y_1$ and $Y_2$ are $CR_6R_7$;

$R_4$ and $R_5$ are each independently selected from the group consisting of hydrogen, cyano, optionally substituted alkyl, optionally substituted alkenyl, optionally substituted alkynyl, optionally substituted cycloalkyl, optionally substituted heterocyclylalkyl, optionally substituted arylalkyl, optionally substituted aryl, optionally substituted heteroarylalkyl, optionally substituted heteroaryl;

$R_6$ and $R_7$ are each independently selected from the group consisting of hydrogen, halo, cyano, hydroxy, optionally substituted alkyl, optionally substituted alkenyl, optionally substituted alkynyl, optionally substituted cycloalkyl, optionally substituted heterocyclylalkyl, optionally substituted arylalkyl, optionally substituted aryl, optionally substituted heteroarylalkyl, optionally substituted heteroaryl, $OR_4$, $NR_4R_5$, $SR_4$, $COR_4$, $COOR_4$, $CONR_4R_5$, $NHCOR_4$, $OCOR_4$, $CSR_4$, $CSOR_4$, $CSNR_4R_5$, $NHCSR_4$, $OCSR_4$, $S(O)_nR_4$, $SO_2NR_4R_5$, $OSO_2R_4$, $NHSO_2R_4$;

$R_8$ and $R_9$ are each independently selected from the group consisting of hydrogen, optionally substituted alkyl, optionally substituted alkenyl, optionally substituted alkynyl, optionally substituted cycloalkyl, optionally substituted heterocyclylalkyl, optionally substituted arylalkyl, optionally substituted heteroarylalkyl; and n is an integer from 1 to 3.

In some embodiments, the compound of Formula (I) is not 4-piperidin-1-ylnaphthalene-1-carbonitrile. In other embodiments, the compound of Formula (I) is not 4-piperidin-1-ylnaphthalene-1-carbonitrile. In yet other embodiments, the compound of Formula (I) is not 4-piperidin-1-ylnaphthalene-1-carbonitrile As used herein, a "heterogroup" refers to a group of two or more atoms, at least one of which is not carbon or hydrogen. Thus, a carbonyl group (C=O) or thiocarbonyl group (C=S), or a substituted nitrogen atom (NRR') in a ring are examples of heterogroups.

The compounds of the invention can be used alone, in combination with other compounds in the invention, or in combination with one or more other agents active in the therapeutic areas described herein.

Some embodiments include prodrugs, stereoisomers and pharmaceutically acceptable salts thereof. In one embodiment ring A is an aromatic, heteroaromatic, or aliphatic ring. In some embodiments, ring A is benzene, cyclohexyl or pyridine. In one embodiment ring B is a bicyclic heterocycle. In one embodiment ring B is tropane or an optionally substituted tropane. In one embodiment $R_3$ is cyano or nitro. In one embodiment ring B is optionally substituted with one or more groups selected from the group consisting of hydrogen, halogen, hydroxy, optionally substituted alkoxy, optionally substituted alkyl, optionally substituted alkenyl, optionally substituted alkynyl, optionally substituted aminoalkyl, and $NHCOR_4$. In one embodiment ring B is optionally substituted with one or more hydroxy groups. In one embodiment $R_6$ or $R_7$ is hydroxy or alkyl. Some embodiments include a prodrug ester, carbonate, carbamate, sulfate, amide, phosphate or phosphoramidate derivative.

In one embodiment, ring B includes only bicyclic or tricyclic non-aromatic heterocycles as described above. In one embodiment, ring B does not include piperazine or 1,4-diazepine.

In some embodiments, prodrugs, metabolites, stereoisomers, and pharmaceutically acceptable salts of the compounds of Formula (I) are provided.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Conventional procedures for the selection and preparation of suitable prodrug derivatives are described, for example, in *Design of Prodrugs*, (ed. H. Bundgaard, Elsevier, 1985), which is hereby incorporated herein by reference in its entirety. A non-limiting example of a prodrug for use herein includes those that promote the solubility of alcohols such as by the procedures described in Mahfous, N. H. et al, *J. Pharm. Pharmacol.*, 53, 841-848 (2001) and Bundgaard, H. et al., *J. Med. Chem.*, 32, 2503-2507 (1989), both of which are incorporated herein by reference in their entirety.

The term "prodrug ester" refers to derivatives of the compounds disclosed herein formed by the addition of any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of prodrug ester groups can be found in, for example, T. Higuchi and V. Stella, in "Prodrugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

Metabolites of the compounds of Formula (I) include active species that are produced upon introduction of the compounds into the biological milieu.

Where the compounds of Formula (I) have at least one chiral center, they may exist as a racemate or as enantiomers. It should be noted that all such isomers and mixtures thereof are included in the scope of the present invention. Furthermore, some of the crystalline forms for the compounds of Formula (I) may exist as polymorphs. Such polymorphs are included in one embodiment of the present invention. In addition, some of the compounds of the present invention may form solvates with water (i.e., hydrates) or common organic solvents. Such solvates are included in one embodiment of the present invention.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

If the manufacture of pharmaceutical formulations involves intimate mixing of the pharmaceutical excipients and the active ingredient in its salt form, then it may be desirable to use pharmaceutical excipients which are non-basic, that is, either acidic or neutral excipients.

In various embodiments, the compounds of Formula (I) can be used alone, in combination with other compounds according to Formula (I), or in combination with one or more other agents active in the therapeutic areas described herein.

The term "halogen atom," as used herein, means any one of the radio-stable atoms of column 7 of the Periodic Table of the Elements, e.g., fluorine, chlorine, bromine, or iodine, with fluorine and chlorine being preferred.

The term "ester" refers to a chemical moiety with formula —(R)$_n$—COOR', where R and R' are independently selected from the group consisting of alkyl, cycloalkyl, aryl, heteroaryl (bonded through a ring carbon), heterocyclylalkyl, arylalkyl or heteroarylalkyl, cycloalkylalkyl, (the rings bonded through the alkyllinker) and heteroalicyclic (bonded through a ring carbon), and where n is 0 or 1.

An "amide" is a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon), heterocyclylalkyl, arylalkyl or heteroarylalkyl, cycloalkylalkyl, (the rings bonded through the alkyllinker) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

The term "aromatic" refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

The term "alkyl," as used herein, means any unbranched or branched, substituted or unsubstituted, saturated hydrocarbon. The alkyl moiety, may be branched, straight chain, or cyclic. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from substituted or unsubstituted cycloalkyl, substituted or unsubstituted cylcloalkenyl, substituted or unsubstituted aryl, substituted or unsubstituted heteroaryl, substituted or unsubstituted heteroaryloxy, heterocyclyl, heterocyclooxy, heteroalicyclyl, hydroxy, substituted or unsubstituted alkoxy, substituted or unsubstituted aryloxy, acyl, thiol, substituted or unsubstituted thioalkoxy, alkylthio, arylthio, cyano, halo, carbonyl, thiocarbonyl, acylalkyl, acylamino, acyloxy, aminoacyl, aminoacyloxy, oxyacylamino, keto, thioketo, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and substituted or unsubstituted amino, including mono- and di-substituted amino groups, and the protected derivatives thereof, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substitutent may be substituted with one of the above substituents.

In the present context, the term "cycloalkyl" is intended to cover three-four-, five-, six-, seven-, and eight- or more membered rings comprising carbon atoms only. A cycloalkyl can optionally contain one or more unsaturated bonds situated in such a way, however, that an aromatic pi-electron system does not arise. Some examples of "cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, or cycloheptene.

An "alkenyl" moiety refers to a group consisting of at least two carbon atoms and at least one carbon-carbon double bond. An alkenyl may be unbranched or branched, substituted or unsubstituted, unsaturated hydrocarbon including polyunsaturated hydrocarbons. In some embodiments, the alkenyl is a $C_1$-$C_6$ unbranched, mono-unsaturated or di-unsaturated, unsubstituted hydrocarbons. The term "cycloalkenyl" refers to any non-aromatic hydrocarbon ring, preferably having five to twelve atoms comprising the ring.

An "alkyne" moiety refers to a group consisting of at least two carbon atoms and at least one carbon-carbon triple bond.

The substituent "R" appearing by itself and without a number designation refers to a substituent selected from the group consisting of alkyl, cycloalkyl, aryl, heteroaryl (bonded through a ring carbon) and heteroalicyclyl (bonded through a ring carbon).

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring.

An "O-carboxy" group refers to a RC(=O)O— group, where R is as defined herein.

A "C-carboxy" group refers to a —C(=O)OR groups where R is as defined herein.

An "acetyl" group refers to a —C(=O)CH$_3$, group.

A "trihalomethanesulfonyl" group refers to a X$_3$CS(=O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonamido" group refers to a X$_3$CS(=O)$_2$NR— group with X and R as defined herein.

An "O-carbamyl" group refers to a —OC(=O)—NR, group-with R as defined herein.

An "N-carbamyl" group refers to a ROC(=O)NH— group, with R as defined herein.

An "O-thiocarbamyl" group refers to a —OC(=S)—NR, group with R as defined herein.

An "N-thiocarbamyl" group refers to an ROC(=S)NH— group, with R as defined herein.

A "C-amido" group refers to a —C(=O)—NR$_2$ group with R as defined herein.

An "N-amido" group refers to a RC(=O)NH— group, with R as defined herein.

The term "perhaloalkyl" refers to an alkyl group where all of the hydrogen atoms are replaced by halogen atoms.

The term "acylalkyl" refers to a RC(=O)R'— group, with R as defined herein, and R' being a diradical alkylene group. Examples of acylalkyl, without limitation, may include CH$_3$C(=O)CH$_2$—, CH$_3$C(=O)CH$_2$CH$_2$—, CH$_3$CH$_2$C(=O)CH$_2$CH$_2$—; CH$_3$C(=O)CH$_2$CH$_2$CH$_2$—, and the like.

The term "aminoalkyl" refers to a substituent selected from the group consisting of —RNR'R", —RNHR', and —RNH$_2$, with R, R', and R" independently being as R is defined herein.

Unless otherwise indicated, when a substituent is deemed to be "optionally substituted," it is meant that the substituent is a group that may be substituted with one or more group(s) individually and independently selected from morpholinoalkanoate, cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

The term "heterocyclyl" is intended to mean three-, four-, five-, six-, seven-, and eight- or more membered rings wherein carbon atoms together with from 1 to 3 heteroatoms constitute said ring. A heterocyclyl can optionally contain one or more unsaturated bonds situated in such a way, however, that an aromatic pi-electron system does not arise. The heteroatoms are independently selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like.

Heterocyclyl rings can optionally also be fused to aryl rings, such that the definition includes bicyclic structures. Typically such fused heterocyclyl groups share one bond with an optionally substituted benzene ring. Examples of benzo-fused heterocyclyl groups include, but are not limited to, benzimidazolidinone, tetrahydroquinoline, and methylenedioxybenzene ring structures.

Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Binding to the heterocycle can be at the position of a heteroatom or via a carbon atom of the heterocycle, or, for benzo-fused derivatives, via a carbon of the benzenoid ring.

In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. The term "aryl" relates to aromatic, including, for example, benzenoid groups, connected via one of the ring-forming carbon atoms, and optionally carrying one or more substituents selected from heterocyclyl, heteroaryl, halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

In the present context, the term "heteroaryl" is intended to mean a heterocyclic aromatic group where one or more carbon atoms in an aromatic ring have been replaced with one or more heteroatoms selected from the group comprising nitrogen, sulfur, phosphorous, and oxygen.

Furthermore, in the present context, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one cycloalkyl ring share at least one chemical bond.

The term "heteroaryl" is understood to relate to aromatic, $C_{3-8}$ cyclic groups further containing one oxygen or sulfur atom or up to four nitrogen atoms, or a combination of one oxygen or sulfur atom with up to two nitrogen atoms, and their substituted as well as benzo- and pyrido-fused derivatives, for example, connected via one of the ring-forming carbon atoms. Heteroaryl groups can carry one or more substituents, selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. In some embodiments, heteroaryl groups can be five- and six-membered aromatic heterocyclic systems carrying 0, 1, or 2 substituents, which can be the same as or different from one another, selected from the list above. Representative examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quionoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

The terms "purified," "substantially purified," and "isolated" as used herein refer to the compounds of the invention being free of other, dissimilar compounds with which the compounds of the invention are normally associated in their natural state, so that the compounds of the invention comprise at least 0.5%, 1%, 5%, 10%, or 20%, and most preferably at least 50% or 75% of the mass, by weight, of a given sample.

In certain embodiments, the compound of Formula (I) is selected from
- 1-(4-Nitronaphthalen-1-yl)pyrrolidine (116BG33),
- 3,5-Dimethyl-4-(4-nitronaphthalen-1-yl)piperidine (116BG35-5),
- 1-(4-Cyanonaphthalen-1-yl)piperidine-3-carboxylic acid diethylamide (136BG73-4),
- 2,6-Dimethyl-4-(4-nitronaphthalen-1-yl)morpholine (116BG35-23),
- 1-(4-Nitronaphthalen-1-yl)-4-pyrrolidin-1-yl-piperidine (116BG35-2),
- 1-(4-Nitronaphthalen-1-yl)piperidine (116BG35-6),
- 4-Methyl-4-(4-nitronaphthalen-1-yl)piperidine (116BG35-7),
- 1-(4-Nitronaphthalen-1-yl)piperidine-4-carboxylic acid ethyl ester. (116BG35-1),
- 4-(4-Nitronaphthalen-1-yl)morpholine (116BG35-10),
- 2,5-Dimethyl-4-(4-nitronaphthalen-1-yl)pyrrolidine (116BG35-24),
- 4-(3-Hydroxymethylpiperidin-1-yl)naphthalene-1-carbonitrile (136BG73-1),
- 4-[4-(2-Hydroxyethyl)piperidin-1-yl]naphthalene-1-carbonitrile (136BG73-9),
- 4-Piperidin-1-ylnaphthalene-1-carbonitrile (136BG73-10),
- 4-(4-Methylpiperidin-1-yl)naphthalene-1-carbonitrile (136BG73-11),
- 4-(4-Hydroxypiperidin-1-yl)naphthalene-1-carbonitrile (136BG73-12),
- 4-(4-Hydroxymethylpiperidin-1-yl)naphthalene-1-carbonitrile (136BG73-13),
- 1-(4-Cyanonaphthalen-1-yl)piperidine-4-carboxylic acid amide (136BG73-17),
- N-[1-(4-Cyanonaphthalen-1-yl)pyrrolidin-3-yl]-N-methylacetamide (136BG73-18),
- 4-(3-Dimethylaminopyrrolidin-1-yl)naphthalene-1-carbonitrile (136BG73-19),
- 4-(3-Hydroxypiperidin-1-yl)naphthalene-1-carbonitrile (136BG73-25),
- 4-(2,6-Dimethylmorpholin-4-yl)naphthalene-1-carbonitrile (136BG73-26),
- 4-(3-Hydroxypyrrolidin-1-yl)naphthalene-1-carbonitrile (136BG85-2),
- 4-((S)-2-Hydroxymethylpyrrolidin-1-yl)naphthalene-1-carbonitrile (136BG85-3-3),
- 4-Pyrrolidin-1-ylnaphthalene-1-carbonitrile (136BG65-3),
- 4-Pyrrolidin-1-ylnaphthalene-1-carboxylic acid ethyl ester (154BG19),
- 4-Pyrrolidin-1-ylnaphthalene-1-carboxylic acid (154BG23),
- 4-(3-endo-Hydroxy-8-azabicyclo[3.2.1]oct-8-yl)naphthalene-1-carbonitrile (154BG31),
- 4-(3-Oxo-8-azabicyclo[3.2.1]oct-8-yl)naphthalene-1-carbonitrile (156AF03-217),
- 4-(3-Propylamino-8-azabicyclo[3.2.1]oct-8-yl)naphthalene-1-carbonitrile, hydrochloride (156AF01-222 & 156AF01-223),
- 4-(3-Dimethylamino-8-azabicyclo[3.2.1]oct-8-yl)naphthalene-1-carbonitrile, hydrochloride (156AF05-224),
- 4-[3-(3-Hydroxypropylamino)-8-azabicyclo[3.2.1]oct-8-yl]naphthalene-1-carbonitrile, hydrochloride (156AF07-225),
- 4-[3-(2-Ethoxyethylamino)-8-azabicyclo[3.2.1]oct-8-yl]naphthalene-1-carbonitrile, hydrochloride (156AF09-226 & 156AF09-227),
- 4-{3-[2-(1H-Imidazol-4-yl)ethylamino]-8-azabicyclo[3.2.1]oct-8-yl}naphthalene-1-carbonitrile, dihydrochloride (156AF11-229),
- 4-(3-Cyclopropylamino-8-azabicyclo[3.2.1]oct-8-yl)naphthalene-1-carbonitrile, hydrochloride (156AF11-230),
- 4-[3-(2-Dimethylaminoethylamino)-8-azabicyclo[3.2.1]oct-8-yl]naphthalene-1-carbonitrile, dihydrochloride (156AF11-231),
- 4-[3-(Cyclohexylmethylamino)-8-azabicyclo[3.2.1]oct-8-yl]naphthalene-1-carbonitrile, hydrochloride (156AF11-232), 4-{3-[(Furan-2-ylmethyl)amino]-8-azabicyclo[3.2.1]oct-8-yl}naphthalene-1-carbonitrile, hydrochloride (156AF11-233),
4-[3-(2-Morpholin-4-ylethylamino)-8-azabicyclo[3.2.1]oct-8-yl]naphthalene-1-carbonitrile, dihydrochloride (156AF11-234),
4-{3-[(Pyridin-2-ylmethyl)amino]-8-azabicyclo[3.2.1]oct-8-yl}naphthalene-1-carbonitrile, dihydrochloride (156AF11-235),
4-[3-(2-Isopropoxyethylamino)-8-azabicyclo[3.2.1]oct-8-yl]naphthalene-1-carbonitrile, hydrochloride (156AF11-237),
4-(1,4-Dioxa-8-azaspiro[4.5]dec-8-yl)naphthalene-1-carbonitrile (156AF14-239),
4-(3-Hydroxyimino-8-azabicyclo[3.2.1]oct-8-yl)naphthalene-1-carbonitrile (156AF17-240),
3-Chloropropionic acid endo-8-(4-cyanonaphthalen-1-yl)-8-azabicyclo[3.2.1]oct-3-yl ester (156AF31-245),
Methoxyacetic acid endo-8-(4-cyanonaphthalen-1-yl)-8-azabicyclo[3.2.1]oct-3-yl ester (88PS39),
3-Morpholin-4-ylpropionic acid endo-8-(4-cyanonaphthalen-1-yl)-8-azabicyclo[3.2.1]oct-3-yl ester, hydrochloride (156AF32-246),
3-(4-Ethylpiperazin-1-yl)propionic acid endo-8-(4-cyanonaphthalen-1-yl)-8-azabicyclo[3.2.1]oct-3-yl ester, hydrochloride (156AF35-247),
3-Diethylaminopropionic acid endo-8-(4-cyanonaphthalen-1-yl)-8-azabicyclo[3.2.1]oct-3-yl ester, hydrochloride (88PS37),
Chloroacetic acid endo-8-(4-cyanonaphthalen-1-yl)-8-azabicyclo[3.2.1]oct-3-yl ester (156AF36-248),
Morpholin-4-ylacetic acid endo-8-(4-cyanonaphthalen-1-yl)-8-azabicyclo[3.2.1]oct-3-yl ester, hydrochloride (156AF37-249),
Imidazol-1-ylacetic acid endo-8-(4-cyanonaphthalen-1-yl)-8-azabicyclo[3.2.1]oct-3-yl ester, hydrochloride (156AF40-251),
(4-Ethylpiperazin-1-yl)acetic acid endo-8-(4-cyanonaphthalen-1-yl)-8-azabicyclo[3.2.1]oct-3-yl ester, dihydrochloride (156AF42-252),
Diethylaminoacetic acid endo-8-(4-cyanonaphthalen-1-yl)-8-azabicyclo[3.2.1]oct-3-yl ester, hydrochloride (156AF43-253),
Succinic acid mono endo-[8-(4-cyanonaphthalen-1-yl)-8-azabicyclo[3.2.1]oct-3-yl]ester (156AF48-254),
Trifluoroacetic acid endo-8-(4-cyanonaphthalen-1-yl)-8-azabicyclo[3.2.1]oct-3-yl ester (156AF54-259),
4-(3,4-Dihydroxypyrrolidin-1-yl)naphthalene-1-carbonitrile (156AF59-258),
4-(3-exo-Ethynyl-3-endo-hydroxy-8-azabicyclo[3.2.1]oct-8-yl)naphthalene-1-carbonitrile (88PS41),
4-[3-(2-[1,3]Dioxan-2-ylethyl)-3-hydroxy-8-azabicyclo[3.2.1]oct-8-yl]naphthalene-1-carbonitrile (156AF53-260),
4-(endo-3-Methoxy-8-azabicyclo[3.2.1]oct-8-yl)naphthalene-1-carbonitrile (88PS44),
(1S,4S)-5-(4-Cyanonaphthalen-1-yl)-2,5-diazabicyclo[2.2.1]heptane-2-carboxylic acid tert-butyl ester (165RL03),
4-((1S,4S)-2,5-Diazabicyclo[2.2.1]hept-2-yl)naphthalene-1-carbonitrile hydrochloride (165RL09),
4-[(1S,4S)-5-(Methoxyacetyl)-2,5-diazabicyclo[2.2.1]hept-2-yl]naphthalene-1-carbonitrile (165RL10),
4-((1S,4S)-5-Acetyl-2,5-diazabicyclo[2.2.1]hept-2-yl)naphthalene-1-carbonitrile (165RL11),
4-[(1S,4S)-5-(2-Hydroxyethyl)-2,5-diazabicyclo[2.2.1]hept-2-yl]naphthalene-1-carbonitrile (165RL12),
4-((1S,4S)-5-Methyl-2,5-diazabicyclo[2.2.1]hept-2-yl)naphthalene-1-carbonitrile hydrochloride (165RL15),
4-(3-Amino-8-azabicyclo[3.2.1]oct-8-yl)naphthalene-1-carbonitrile, hydrochloride (165RL21),
2-Chloro-N-[8-(4-cyanonaphthalen-1-yl)-8-azabicyclo[3.2.1]oct-3-yl]acetamide, hydrochloride (165RL23),
N-[8-(4-Cyanonaphthalen-1-yl)-8-azabicyclo[3.2.1]oct-3-yl]-2-(4-ethylpiperazin-1-yl)acetamide, dihydrochloride (165RL27),
N-[8-(4-Cyanonaphthalen-1-yl)-8-azabicyclo[3.2.1]oct-3-yl]-2-diethylaminoacetamide, hydrochloride (165RL28),
2-Cyanoethyl endo-8-(4-cyanonaphthalen-1-yl)-8-azabicyclo[3.2.1]oct-3-yl N,N-diisopropylamidophosphate (165RL22),
Endo-8-(4-cyanonaphthalen-1-yl)-8-azabicyclo[3.2.1]oct-3-yl hydrogen N,N-diisopropylamidophosphate (165RL29),
1-(3,4-Dinitronaphthalen-1-yl)pyrrolidine, hydrochloride (159JP06),
1-(4,5,7-Trinitronaphthalen-1-yl)pyrrolidine, hydrochloride (159JP09),
2-Bromo-4-pyrrolidin-1-ylnaphthalene-1-carbonitrile, hydrochloride (159JP07),
4-Pyrrolidin-1-ylnaphthalene-1,3-dicarbonitrile, hydrochloride (159JP26),
1-(4,8-Dinitronaphthalen-1-yl)pyrrolidine, hydrochloride (159JP29),
4-Pyrrolidin-1-ylnaphthalene-1-sulfonic acid (139MBT58-C),
[4-(Pyrrolidin-1-yl)naphthalen-1-yl]phosphonic acid diethyl ester (139MBT64-B),
[4-(Pyrrolidin-1-yl)naphthalen-1-yl]phosphonic acid monoethyl ester (139MBT64-2C),
1-(4-Methanesulfonylnaphthalen-1-yl)pyrrolidine (139MBT70-B),
[4-(Pyrrolidin-1-yl)naphthalen-1-yl]sulfonic acid amide (139MBT76-C),
[8-(4-Cyanonaphthalen-1-yl)-8-azabicyclo[3.2.1]oct-3-yl]urea (139MBT94-C),
Dimethylcarbamic acid endo-8-(4-cyanonaphthalen-1-yl)-8-azabicyclo[3.2.1]oct-3-yl ester (139MBT84-1E),
4-(4-Hydroxy-4-phenylpiperidin-1-yl)naphthalene-1-carbonitrile (196MBT2-4),
4-Azepan-1-ylnaphthalene-1-carbonitrile (196MBT2-6),
4-(2,5-Dimethyl-2,5-dihydropyrrol-1-yl)naphthalene-1-carbonitrile (196MBT2-7),
4-(3,6-Dihydro-2H-pyridin-1-yl)naphthalene-1-carbonitrile (196MBT2-9),
4-(8-Oxo-1,5,6,8-tetrahydro-2H,4H-1,5-methanopyrido[1,2-a][1,5]diazocin-3-yl)naphthalene-1-carbonitrile (196MBT2-10),
4-Thiomorpholin-4-ylnaphthalene-1-carbonitrile (196MBT2-11),
4-(4-Benzyl-4-hydroxypiperidin-1-yl)naphthalene-1-carbonitrile (196MBT2-16),
4-(4-Oxo-1-phenyl-1,3,8-triaza-spiro[4.5]dec-8-yl)naphthalene-1-carbonitrile (196MBT2-17),
4-(4-Benzoylpiperidin-1-yl)naphthalene-1-carbonitrile (196MBT2-19),
1-(4-Cyanonaphthalen-1-yl)$_4$-phenylpiperidine-4-carbonitrile (196MBT2-20),
4-((S)-4a-Hydroxyoctahydroisoquinolin-2-yl)naphthalene-1-carbonitrile (196MBT2-24),
4-(6-Methoxy-3,4-dihydro-1H-isoquinolin-2-yl)naphthalene-1-carbonitrile (196MBT2-26), 4-((R)-2-Phenylaminomethylpyrrolidin-1-yl)naphthalene-1-carbonitrile (196MBT2-2),
4-(9-Hydroxy-1,5,7-trimethyl-3,7-diazabicyclo[3.3.1]non-3-yl)naphthalene-1-carbonitrile (196MBT2-13),
4-(3-Endo-hydroxy-3-exo-methyl-8-azabicyclo[3.2.1]oct-8-yl)naphthalene-1-carbonitrile (156AF70-267),
4-(3-endo-hydroxy-3-exo-propyl-8-azabicyclo[3.2.1]oct-8-yl)naphthalene-1-carbonitrile (156AF96-284),
4-(endo-Spiro[8-azabicyclo[3.2.1]octane-3,2'-oxiran]-8-yl)naphthalene-1-carbonitrile (183AF16-294),
4-[3-exo-(4-ethylpiperazin-1-ylmethyl)-3-endo-hydroxy-8-azabicyclo[3.2.1]oct-8-yl]naphthalene-1-carbonitrile (183AF 18-295),
4-(3-endo-hydroxy-3-exo-hydroxymethyl-8-azabicyclo[3.2.1]-oct-8-yl)naphthalene-1-carbonitrile (183AF19-296),
4-(3-exo-Cyanomethyl-3-endo-hydroxy-8-azabicyclo[3.2.1]oct-8-yl)naphthalene-1-carbonitrile (183AF21-297),
4-(3-endo-Hydroxy-3-exo-{[2-(1H-imidazol-4yl)ethylamino]methyl}-8-azabicyclo[3.2.1]oct-8-yl)naphthalene-1-carbonitrile (183AF23-298),
4-(3-endo-Hydroxy-3-exo-methoxymethyl-8-azabicyclo[3.2.1]oct-8-yl)naphthalene-1-carbonitrile (183AF24-299),
7-Bromo-4-pyrrolidin-1-ylnaphthalene-1-carbonitrile, hydrochloride and 6-bromo-4-pyrrolidin-1-ylnaphthalene-1-carbonitrile, hydrochloride (159JP02-X3),
4-(8-Azaspiro[4.5]dec-8-yl)naphthalene-1-carbonitrile (159JP61 AA),
4-Nitrobenzoic acid exo-8-(4-cyanonaphthalen-1-yl)-8-azabicyclo[3.2.1]oct-3-yl ester (159JP66C),
4-(3-exo-Hydroxy-8-azabicyclo[3.2.1]oct-8-yl)naphthalene-1-carbonitrile (159JP68F6),
4-(3-exo-Methoxy-8-azabicyclo[3.2.1]oct-8-yl)naphthalene-1-carbonitrile (159JP72A),
(S)-1-(4-Cyanonaphthalen-1-yl)pyrrolidine-2-carboxylic acid methyl ester (159JP74A),
4-(8-Azabicyclo[3.2.1]oct-2-en-8-yl)naphthalene-1-carbonitrile (159JP80XX),
4-(8-Azabicyclo[3.2.1]oct-8-yl)naphthalene-1-carbonitrile (173FBA64b),
Acrylic acid endo-8-(4-cyanonaphthalen-1-yl)-8-azabicyclo[3.2.1]oct-3-yl ester (159JP79),
3-Pyrrolidin-1-yl-propionic acid endo-8-(4-cyanonaphthalen-1-yl)-8-azabicyclo[3.2.1]oct-3-yl ester, fumarate (159JP82F6),
3-Imidazol-1-yl-propionic acid endo-8-(4-cyanonaphthalen-1-yl)-8-azabicyclo[3.2.1]oct-3-yl ester, fumarate (159JP83A),
3-Pyrazol-1-yl-propionic acid endo-8-(4-cyano-naphthalen-1-yl)-8-azabicyclo[3.2.1]oct-3-yl ester, fumarate (159JP85A),
4-(2-Methyl-3-oxo-8-azabicyclo[3.2.1]oct-8-yl)naphthalene-1-carbonitrile (159JP84),
4-(2-Methyl-8-azabicyclo[3.2.1]oct-8-yl)naphthalene-1-carbonitrile (159JP87A),
4-(3-exo-Benzyl-3-endo-hydroxy-8-azabicyclo[3.2.1]oct-8-yl)naphthalene-1-carbonitrile (159JP92A),
8-(4-Cyanonaphthalen-1-yl)-8-azabicyclo[3.2.1]oct-2-ene-2-carboxylic acid methyl ester (159JP95C),
8-(4-Cyanonaphthalen-1-yl)-8-azabicyclo[3.2.1]octane-2-carboxylic acid methyl ester (159JP97A),
4-(2-Hydroxymethyl-8-azabicyclo[3.2.1]oct-2-en-8-yl)naphthalene-1-carbonitrile (159JP98C),
(1R,2R,3S,5S)-3-Benzoyloxy-8-(4-cyanonaphthalen-1-yl)-8-azabicyclo[3.2.1]octane-2-carboxylic acid methyl ester (195JP02A),
(1R,2R,3S,5S)-4-(3-Hydroxy-2-hydroxymethyl-8-azabicyclo[3.2.1]oct-8-yl)naphthalene-1-carbonitrile (195JP05BX),
2-Cyanoethyl endo-8-(4-cyanonaphthalen-1-yl)-8-azabicyclo[3.2.1]oct-3-yl N,N-diisopropylamidophosphite (165RL31),
2-Cyanoethyl endo-8-(4-cyanonaphthalen-1-yl)-8-azabicyclo[3.2.1]oct-3-yl diisopropylamidophosphate (165RL37),
2-Cyanoethyl ethyl endo-8-(4-cyanonaphthalen-1-yl)-8-azabicyclo[3.2.1]oct-3-yl phosphate (165RL38),
Ethyl endo-8-(4-cyanonaphthalen-1-yl)-8-azabicyclo[3.2.1]oct-3-yl hydrogen phosphate (165RL41),
Bis(2-cyanoethyl) endo-8-(4-cyanonaphthalen-1-yl)-8-azabicyclo[3.2.1]oct-3-yl phosphate (165RL42),
Endo-8-(4-cyanonaphthalen-1-yl)-8-azabicyclo[3.2.1]oct-3-yl dihydrogen phosphate (165RL43),
2-Cyanoethyl endo-8-(4-cyanonaphthalen-1-yl)-8-azabicyclo[3.2.1]oct-3-yl phenyl phosphate (165RL44),
Endo-8-(4-cyanonaphthalen-1-yl)-8-azabicyclo[3.2.1]oct-3-yl phenyl hydrogen phosphate (165RL45),
N-[8-(4-cyanonaphthalen-1-yl)-8-azabicyclo[3.2.1]oct-3-yl]acetamide (165RL51),
3-Chloro-N-[8-(4-cyanonaphthalen-1-yl)-8-azabicyclo[3.2.1]oct-3-yl]propanamide (165RL50),
N-[8-(4-cyanonaphthalen-1-yl)-8-azabicyclo[3.2.1]oct-3-yl]-3-(4-ethylpiperazin-1-yl)propanamide, dihydrochloride (165RL52),
N-[8-(4-Cyanonaphthalen-1-yl)-8-azabicyclo[3.2.1]oct-3-yl]-3-diethylaminopropionamide, hydrochloride (165RL53),
N-[8-(4-cyanonaphthalen-1-yl)-8-azabicyclo[3.2.1]oct-3-yl]-3-(1H-imidazol-1-yl)propanamide hydrochloride (165RL55),
N-[8-(4-Cyanonaphthalen-1-yl)-8-azabicyclo[3.2.1]oct-3-yl]-2-(ethoxyethoxy)acetamide (165RL57),
1-(4-Cyanonaphthalen-1-yl)piperidine-3-carboxylic acid ethyl ester (165RL60),
4-(2-Methylpiperidin-1-yl)naphthalene-1-carbonitrile (165RL62),
1-(4-Cyanonaphthalen-1-yl)piperidine-3-carboxylic acid (165RL63),
[1-(4-Cyanonaphthalen-1-yl)piperidin-3-ylmethyl]carbamic acid tert-butyl ester (165RL65),
4-(3-Aminomethylpiperidin-1-yl)naphthalene-1-carbonitrile(165RL66),
N-[1-(4-Cyanonaphthalen-1-yl)piperidin-3-ylmethyl]acetamide (165RL70),
4-(3-Ethylaminomethylpiperidin-1-yl)naphthalene-1-carbonitrile hydrochloride (165RL72sec),
4-(3-Diethylaminomethylpiperidin-1-yl)naphthalene-1-carbonitrile hydrochloride (165RL72tert),
1-(4-Cyanonaphthalen-1-yl)piperidine-3-carbonitrile (165RL73-3),
1-(4-Cyanonaphthalen-1-yl)piperidine-3-carboxamide (165RL73-5),
4-(3-Fluoropiperidin-1-yl)naphthalene-1-carbonitrile (165RL74),
trans-4-(4-Hydroxycyclohexylamino)naphthalene-1-carbonitrile (165RL96),
Methanesulfonic acid trans-4-(4-cyanonaphthalen-1-ylamino)cyclohexyl ester (165RL97),
4-(7-Azabicyclo[2.2.1]hept-7-yl)naphthalene-1-carbonitrile hydrochloride (198RL01), N-[8-(4-cyanonaphthalen-1-yl)-8-azabicyclo[3.2.1]oct-3-yl]-4-methylbenzenesulfonylhydrazone (173FBA60a),
4-[2-(Hydroxymethyl)piperidin-1-yl]naphthalene-1-carbonitrile (173FBA70e),
3-exo-[8-(4-Cyanonaphthalen-1-yl)-3-endo-hydroxy-8-azabicyclo[3.2.1]oct-3-yl]-N,N-dimethylpropanamide (173FBA51bH),
2-exo-[8-(4-Cyanonaphthalen-1-yl)-3-endo-hydroxy-8-azabicyclo[3.2.1]oct-3-yl]-N,N-dimethylethanesulfonamide (173FBA56b3),
4-(3-Endo-hydroxy-3-exo-methyl-8-azabicyclo[3.2.1]oct-8-yl)naphthalene-1-carbonitrile, hydrochloride (197FBA23a),
4-(3-Methyl-8-azabicyclo[3.2.1]oct-2-en-8-yl)naphthalene-1-carbonitrile (197FBA24c),
4-Pyrrolidin-1-yl-phthalazine-1-carbonitrile, hydrochloride (141JP56P2A),
7-Pyrrolidin-1-yl-benzo[1,2,5]thiadiazole-4-carbonitrile, hydrochloride (141JP57P1),
1-Pyrrolidin-1-yl-isoquinoline-4-carbonitrile, hydrochloride (141JP71F),
8-Pyrrolidin-1-yl-quinoxaline-5-carbonitrile, hydrochloride (141JP76PY),
5-Pyrrolidin-1-yl-isoquinoline-8-carbonitrile, hydrochloride (141JP79P1),
8-Pyrrolidin-1-yl-isoquinoline-5-carbonitrile, hydrochloride (141JP79P2A),
5-Nitro-8-pyrrolidin-1-yl-quinoline, hydrochloride (144AF60-214B),
1-(4-Nitro-5,6,7,8-tetrahydronaphthalen-1-yl)pyrrolidine (173FBA22a),
8-Nitro-5-pyrrolidin-1-yl-isoquinoline (173FBA26b),
8-Nitro-5-pyrrolidin-1-yl-1,2,3,4-tetrahydroisoquinoline (173FBA29b3),
5-Nitro-8-pyrrolidin-1-yl-1,2,3,4-tetrahydroquinoline (173FBA33b),
1-(8-Nitro-5-pyrrolidin-1-yl-3,4-dihydro-1H-isoquinolin-2-yl)ethanone (173FBA35b),
5-Pyrrolidin-1-yl-quinoline-8-carbonitrile (88PS18),
3-piperazin-1-ylpropionic acid endo-8-(4-cyanonaphthalen-1-yl)-8-azabicyclo[3.2.1]oct-3-yl ester, dihydrochloride 88PS64),
3-[Bis(2-hydroxyethyl)amino]propionic acid endo-8-(4-cyanonaphthalen-1-yl)-8-azabicyclo[3.2.1]oct-3-yl ester, fumarate (88PS65),
3-(3-Dimethylaminopyrrolidin-1-yl)propionic acid endo-8-(4-cyanonaphthalen-1-yl)-8-azabicyclo[3.2.1]oct-3-yl ester, difumarate (88PS67),
3-(4-Methylpiperazin-1-yl)propionic acid endo-8-(4-cyanonaphthalen-1-yl)-8-aza-bicyclo[3.2.1]oct-3-yl ester, difumarate (88PS69), and
4-(3-Diethylaminomethyl-3-hydroxy-8-azabicyclo[3.2.1]oct-8-yl)naphthalene-1-carbonitrile, hydrochloride, (183AF03-288).

Methods of Preparation

The compounds of Formula (I) can be synthesized by methods described below, or by modification of these methods. Ways of modifying the methodology include, among others, temperature, solvent, reagents etc., and will be obvious to those skilled in the art. In general, during any of the processes for preparation of the compounds of Formula (I), it may be necessary and/or desirable to protect sensitive or reactive groups on any of the molecules concerned. This can be achieved by means of conventional protecting groups, such as those described in *Protective Groups in Organic Chemistry* (ed. J. F. W. McOmie, Plenum Press, 1973); and Greene & Wuts, *Protective Groups in Organic Synthesis*, John Wiley & Sons, 1991, which are both hereby incorporated herein by reference in their entirety. The protecting groups can be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety.

In one embodiment, the compounds disclosed herein can be prepared starting from halo-substituted aromatic rings such as C (Scheme1) by base catalyzed aromatic nucleophilic substitution of a halogen with the appropriate amine D to get compounds of the general Formula (I). The process can be carried out in a suitable solvent, e.g. an aprotic solvent such as toluene, acetonitrile, benzene, dioxane, THF, DMSO or DMF with a suitable base such as pyridine, DBU or potassium carbonate and using an excess of the secondary amine (which also can act as the base). The reaction can occur at a temperature between +20° C. and +150° C. Alternatively, the reaction can be carried out under microwave irradiation at temperatures up to 300° C.

Scheme 1

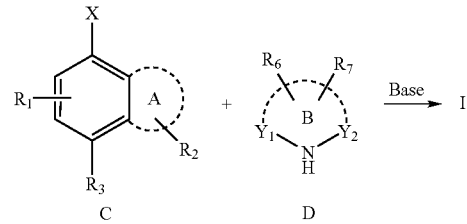

$R_1$, $R_2$, $R_3$, $R_6$, $R_7$ in Scheme I are defined as in Formula (I), above, or are suitable precursors thereof, and X represents a halide.

In another embodiment, the compounds of Formula (I) disclosed herein can be prepared by introducing the amine D through metal-catalysed (e.g. palladium or nickel) nucleophilic substitution on an appropriately substituted halo- or pseudohalo bicyclic (e.g. Br, I-, Cl-, triflate-, nonaflate-, tosylate-substituted aryl derivatives) (Hartwig, *Angew. Chem. Int. Ed.*, 1998, 37, 2046-2067; Yang & Buchwald, *J. Organometallic Chem.*, 1999, 576, 125-146; Hartwig in *Modern Amination Methods*; Ricci, Ed.; Wiley-VCH: Weinheim, Germany, 2000) or Cu-catalyzed (Buchwald et al, *Org. Lett.*, 2002, 4, 581-584; Kwong & Buchwald, *Org. Lett.*, 2003, 5, 793-796). Metal-catalyzed amination reaction can also be performed under microwave irradation (T. Wang et al., *Org. Lett.*, 2003, 5, 897-900); all of which are hereby incorporated herein by reference in their entirety.

In yet another embodiment, the compounds of Formula (I) disclosed herein can be prepared from the appropriately substituted aniline-based derivatives using an appropriate bifunctional alkyl-linker as shown in Scheme 2. The leaving groups $L_1$ and $L_2$ are suitably a halogen atom, e.g., chlorine, bromine or iodine, or a sulfonate, e.g., tosylate or mesylate, or another leaving group favoring the reaction. The reaction is conveniently carried out by stirring the reagent under basic conditions in an inert solvent, e.g., diisopropylethylamine in acetonitrile, or $K_2CO_3$ in N,N-dimethylformamide. The reaction is typically carried out at temperatures between room temperature and 120° C.

Scheme 2

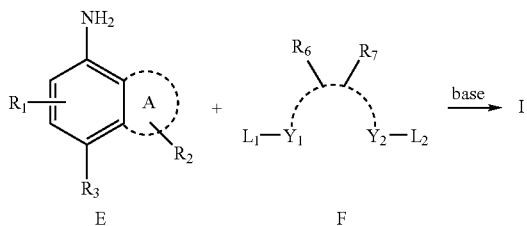

$R_1$, $R_2$, $R_3$, $R_6$, $R_7$ in Scheme 2 are defined in are defined as in Formula (I), above, or are suitable precursors thereof, and $L_1$ and $L_2$ represent a suitable leaving group.

The appropriate starting materials are commercially available or can be prepared according to methodology disclosed in the literature. Substituents $R_1$, $R_2$ and $R_3$ and any $R_6$ and $R_7$ can each be individually introduced at any appropriate stage of the preparation of the compounds, following procedures known in the literature (e.g. W. Adcock et al., *J. Am. Chem. Soc.*, 1967, 89, 386-390; G. Schiemann et al., *Ann.*, 1931, 487, 270-287; Dewar et al., *J. Am. Chem. Soc.*, 1962, 84, 3541-3546; S. Sekiguchi et al., *J. Org. Chem.*, 1979, 44, 3921-3925, all of which are incorporated by reference herein in their entirety).

Compounds of the invention in which $R_3$ is nitro can be prepared by classical nitration methods described in the literature, using $HNO_3/H_2SO_4$ or other methods known to those skilled in the art.

Compounds of the invention in which $R_1$, $R_2$ or $R_3$ are halogen, can be prepared by classical halogenation methods described in the literature, using $Br_2$ or other methods known to those skilled in the art. Alternatively, an appropriately substituted aniline-based precursor can be converted into a halo-derivative via a diazotization according to the Sandmeyer methodology using sodium nitrite in acetic acid or trifluoroacetic acid, and then reacted with an acid, e.g. with hexafluorophosphoric acid, and decomposition of the resulting salt to obtain the fluoro-derivative (W. Adcock et al., *J. Am. Chem. Soc.*, 1967, 89, 386-390, which is hereby incorporated herein by reference in its entirety).

Compounds of the invention in which $R_1$, $R_2$ or $R_3$ are cyano, $CONR_4R_5$, $COOR_4$ can be obtained by Pd catalyzed cyanation from corresponding iodides, bromides (Alterman & Hallberg, *J. Org. Chem.*, 2000, 65, 7984-7989) and chlorides (Sundermeier et al, *Angew. Chem. Int. ed.*, 2003, 42, 1661-1664) as well as by Ni mediated cyanation of aryl bromides and chlorides (Arvela & Leadbeater, *J. Org. Chem.*, 2003, 68, 9122-9125); where all these references are incorporated herein by reference in its entirety. The nitriles can also be obtained by reaction of a halo-derivative or a Sandmeyer diazo-intermediate with cuprous cyanide. The aryl nitriles thus obtained can be either converted to the corresponding tetrazoles by microwave-induced cycloaddition chemistry (Alterman & Hallberg, *J. Org. Chem.*, 2000, 65, 7984-7989, which is hereby incorporated herein by reference in its entirety) or hydrolyzed to corresponding carboxylic acids. In addition, compounds bearing carboxylic acid residues can be accessed from corresponding aryl iodides, bromides and triflates by Pd catalyzed hydroxycarbonylation chemistry (Cacchi et al, *Org. Lett*, 2003, 5, 4269-4293; which is hereby incorporated herein by reference in its entirety), compounds bearing aryl amide residues can be accessed from corresponding aryl bromides by Pd catalyzed aminocarbonylation chemistry (Wan et al, *J. Org. Chem.*, 2002, 67, 6232-6235, which is hereby incorporated herein by reference in its entirety). The carboxylic acids can be further derivatized to amides by classical acylation reactions or coupling agents methodology described in the art.

Compounds of the invention in which $R_1$, $R_2$ or $R_3$ are $S(O)R_8$, $S(O)_2R_8$, $S(O)(OR_8)$, $S(O)_2(OR_8)$, or $SO_2NR_8R_9$ can be prepared using the following methods: Sulfonates can be prepared by direct aryl sulfonation by use of concentrated sulfuric acid, $SO_3$ or chlorosulphonic acid or by hydrolysis of a sulfonyl chloride. The sulfonyl chloride can be obtained by addition of $SO_2$ to a diazonium salt in the presence of cupric chloride. Alternatively, sulfonyl chlorides can be prepared by addition of $SO_2$ (forming a sulfinic acid salt) to aryl metal complexes, e.g. aryl lithium or aryl Grignard reagents, followed by reaction with sulfuryl chloride. Sulfonic acid esters and sulfonamides are conveniently prepared from sulfonyl chlorides by reaction alcohols and amines. Sulfones can be prepared by Friedel-Crafts type reaction of aromatic compounds with sulfonyl halides, by reaction of alkyl halides or sulfonates with aryl sulfinic acid salts, by addition of Grignard reagents to sulfonyl chlorides or by oxidation of aryl sulfides. Sulfoxides may be prepared by oxidation of aryl sulfides.

Compounds of the invention in which $R_3$ are $P(O)(OR_4)(OR_5)$, $P(O)(OH)(NR_4R_5)$, $PO(NR_4R_5)_2$ can be prepared using the following methods: Phosphonates can be prepared by addition of dialkylchlorophosphates to aryl metal complexes, e.g. aryl lithium or aryl Grignard reagents, followed by hydrolysis of one or both of the ester groups. Alternatively, phosphonates can be prepared by addition of $PCl_3$ to a diazonium salt in the presence of cuprous chloride, followed by hydrolysis. In a similar fashion, using the appropriate halide derivatives, phosphonoamidates or —diamidates can be prepared.

Compounds of the invention in which $R_1$, $R_2$ or $R_3$ are alkoxy, $OCOR_4$ can be typically prepared by Williamson ether synthesis from the corresponding hydroxyaryl derivatives for the alkoxy derivatives or by acylation using methods described below.

Compounds of the invention in which $R_1$, $R_2$ or $R_3$ are $COR_4$ can be prepared from corresponding aryl iodides by Pd catalyzed acylation chemistry (Cacchi et al, *Org. Lett*, 2003, 5, 289-293, which is hereby incorporated herein by reference in its entirety). Alternatively, they can be obtained from the corresponding aryls by Friedel-Crafts chemistry (Read, *J. Am. Chem. Soc.*, 1922, 44, 1746-1755, which is hereby incorporated herein by reference in its entirety), or by addition of aryl-Grignard reagents to nitriles (Whitmore et al, *J. Am. Chem. Soc.*, 1947, 69, 235-237, which is hereby incorporated herein by reference in its entirety) or to acyl chlorides (Whitmore & Lester, *J. Am. Chem. Soc.*, 1942, 64, 1247, which is hereby incorporated herein by reference in its entirety), or by either Pd-catalyzed (Gooβen and Ghosh, *Angew. Chem. Int. Ed. Engl.*, 2001, 40, 3458-3460) or Rh-catalyzed acylation of arylboronic acids (Frost & Wadsworth, *Chem. Commun.*, 2001, 22, 2316-2317, both of which are hereby incorporated herein by reference in its entirety).

Compounds of the invention in which $R_1$, $R_2$ or $R_3$ are amino, lower aminoalkyl, $NHCOR_4$, $NHSO_2R_4$ can be obtained from an aniline-based precursor, which is commercially available or can be obtained by reduction from a nitro-derivative prepared as described above, using e.g. Raney nickel and hydrazine or Pd or Pt catalysts and hydrogen. Alternatively, an aminoalkyl group can be introduced following the same methods as described above (Scheme 1) or by reductive amination (Emerson & Walters, *J. Am. Chem. Soc.*, 1938, 60, 2023; Milovic et al, *Synthesis*, 1991, 11, 1043-1045, both of which are hereby incorporated herein by reference in its entirety), or by dehydrative alkylation (Rice & Kohn, *J. Am. Chem. Soc.*, 1955, 77, 4052; Brown & Reid, *J. Am. Chem. Soc.*, 1924, 46, 1838, both of which are hereby incorporated herein by reference in its entirety). Additionally, compounds of this type can also be synthesized from corresponding boronic acids by Cu-catalyzed coupling (Antilla & Buchwald, *Org. Lett.*, 2001, 3, 2077-2079, which is hereby incorporated herein by reference in its entirety). The amino group can be further derivatized by alkylation, acylation (Wolf, *Liebigs Ann. Chem.*, 1952, 576, 35; Yasukara et al, *J. Chem. Soc. Perkin Trans.* 1, 2000, 17, 2901-2902; Nigam & Weedon, *J. Chem. Soc.*, 1957, 2000, all of which are hereby incorporated herein by reference in its entirety), formylation (Hirst & Cohen, *J. Chem. Soc.*, 1895, 67, 830; Olah & Kuhn, *Chem. Ber.* 1956, 89, 2211; Guthrie et al, *Can. J. Chem.*, 1993, 71, 2109-2122, all of which are hereby incorporated herein by reference in its entirety) or sulfonylation. Alternatively, compounds bearing amide substituents can be obtained from suitable halo- or pseudohalo precursor either by Pd catalyzed (Yin & Buchwald, *J. Am. Chem. Soc.*, 2002, 124, 6043-6048, which is hereby incorporated herein by reference in its entirety) or by Cu catalyzed (Buchwald et al, *J. Am. Chem. Soc.*, 2002, 124, 7421-7428, which is hereby incorporated herein by reference in its entirety) amidation chemistries.

Compounds of the invention in which $R_1$ or $R_2$ is $SR_4$ can be obtained from a suitable halo- or pseudohalo precursor by Pd catalyzed (Li, *J. Org. Chem.*, 2002, 67, 3643-3650, which is hereby incorporated herein by reference in its entirety), or Cu catalyzed thioetherification chemistry (Kwong & Buchwald, *Org. Lett.*, 2002, 4, 3517-3520, which is hereby incorporated herein by reference in its entirety). Alternatively, these compounds can be prepared by alkylation of corresponding aryl-thiol precursors (Vogel, *J. Chem. Soc.*, 1948, 1809; Landini & Rocca, *Synthesis*, 1974, 565-566; Bun-Hoi et al, *J. Org. Chem.*, 1951, 16, 988, all of which are hereby incorporated herein by reference in its entirety). Alternatively, alkylarylsulfanyls can be obtained by irradiation of benzenethiols and alkenes (Screttas and Micha-Screttas, *J. Org. Chem.*, 1978, 43, 1064-1071, which is hereby incorporated herein by reference in its entirety).

Furthermore, starting from aryl bromides and iodides, employing alkyl lithium and alkyl Grignard reagents, halogen-metal exchange chemistry can be utilized to introduce a broad range of electrophiles such as alkyls, —Si(R)$_3$, —CHO, —COOH, —CN, —SO$_2$N(R)$_2$, —SR, —B(OR)$_2$, —Sn(R)$_3$, —ZnX (X=Br, Cl).

In general, an amine or alcohol functionality can be further derivatized and for example acylated using any carboxylic acid halide e.g., chloride, or carboxylic anhydride to give amides, as exemplified in Scheme 3 by amine or alcohol K. The reaction is typically carried out using an excess of the acylating agent and a suitable base, e.g., triethylamine or diisopropylethylamine in an inert solvent, e.g., dichloromethane, at a temperature between 0° C. and room temperature and under dry conditions. As an alternative to the carboxylic acid halides and carboxylic acid anhydrides, the amine/alcohol can be acylated using a carboxylic acid and a suitable coupling reagent e.g. PyBroP, DCC or EDCI. The reaction is typically carried out using an excess of the acylating agent and the coupling reagent in an inert solvent, e.g., dichloromethane, at a temperature between 0° C. and 100° C. under dry conditions.

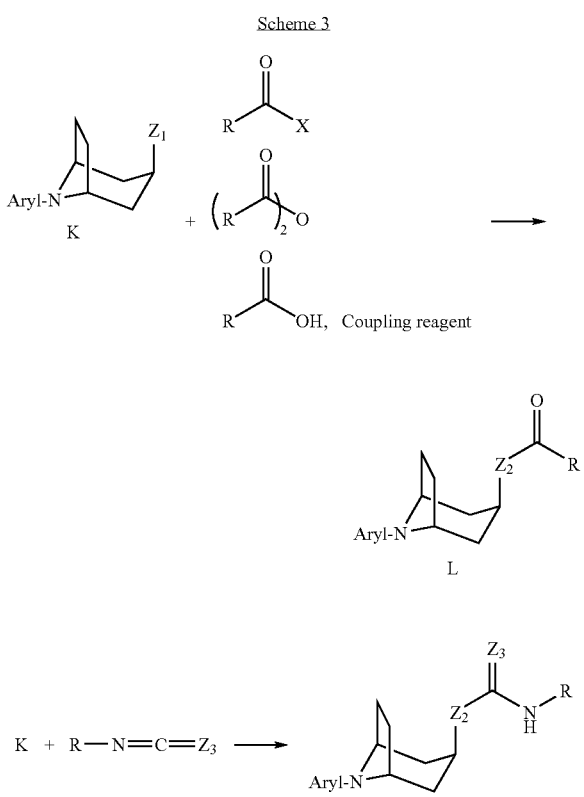

wherein R and Aryl are defined in agreement with Formula (I), $Z_1$ is OH, NH$_2$, NHR* or SH, $Z_2$ is O, NH, NR* or S, $Z_3$ is O or S. and X represents a halide and R* is an alkyl or substituted alkyl.

Alternatively, an amine or alcohol functionality can be alkylated using an appropriate alkylating agents, such as T-L$_1$. Leaving group L$_1$ is suitably a halogen atom, e.g., chlorine, bromine or iodine, or a sulfonate, e.g., tosylate or mesylate, or another leaving group favoring the reaction. The reaction is conveniently carried out by stirring the reagent under basic conditions in an inert solvent, e.g., diisopropylethylamine in acetonitrile, or K$_2$CO$_3$ in N,N-dimethylformamide. The reaction is typically carried out at temperatures between room temperature and 80° C.

Furthermore, ketones, exemplified in Scheme 4 by tropanone derivative G, can be modified by reductive amination using any primary or secondary amine HNRR*, Alternatively the same methodology can be used to modify primary or secondary amines, exemplified by amine J (Scheme 4). The reaction is conveniently carried out by stirring the reactants in an inert solvent such as methanol or ethanol. As a reducing agent, solid-supported borohydride, NaBH$_4$, NaCNBH$_3$, BH$_3$.pyridine, H$_2$/Pd—C or any related reagent can be used, including solid-supported reagents. The reaction is typically carried out at room temperature, but less reactive carbonyl compounds can require higher temperatures and/or the pre-formation of the corresponding imine under water removal before addition of the reducing agent.

Scheme 4

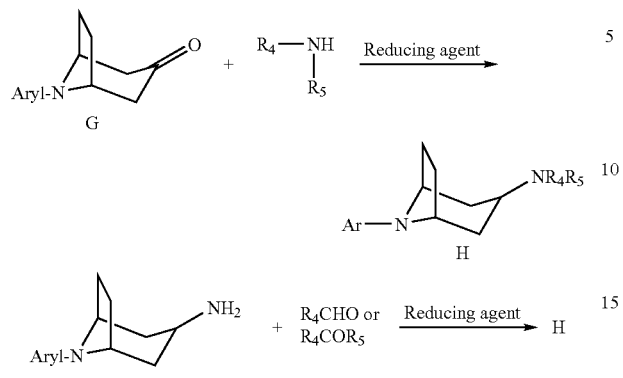

wherein R₄, R₅ and Aryl are defined in agreement with Formula (I)

Furthermore, ketones, exemplified in Scheme 5 by tropanone derivative G, can be reacted with a variety of organometallic reagents, such as Grignard or lithium reagents, where R₆ and Aryl are defined in agreement with Formula (I), to give derivatives such as K. The Grignard reaction is typically carried out in a solvent such as THF, and in some cases the addition of anhydrous cerium trichloride can improve the reaction yields.

Alternatively, ketones exemplified by tropanone G (Scheme 5) can be converted to epoxides L upon reaction with a sulfur ylide such as dimethylsulfoxonium methylide and dimethylsulfonium methylide, generated from trimethylsulfoxonium iodide or trimethylsulfonium iodide by addition of a base such as sodium hydride, in an inert solvent such as dimethylsulfoxide at a temperature of 0-40° C. Alternatively, ketone G can be converted into an olefin by a Wittig or Wadsworth-Horner-Emmons reaction, or by Tebbe olefination. The alkenes thus obtained can then be converted into the corresponding epoxide by treatment with oxidation reagents such as hydroperoxide or MCPBA. Epoxides such as derivative L can be further derivatized by reactions with a wide variety of nucleophiles, such as cyanide, alkoxides, amines, organometallic reagents, or carbanions derived from amide or sulfonamide derivatives upon treatment with base, to give tertiary alcohols exemplified by derivatives M1-M6, where R₄, R₅, R₆, and Aryl are defined in agreement with Formula (I). Certain reactions can be facilitated by the addition of a Lewis acid catalyst such as ytterbium triflate or boron trifluoride etherate. Furthermore, the epoxide can be reduced to the tertiary alcohol using a reducing agent such as LiAlH₄, NaBH₄/LiCl, Superhydride, borane, catalytic hydrogenation or any related reagent can be used, including solid-supported reagents. The reactions can typically be carried out at temperatures of 0-100° C. in solvents such as THF, diethylether, or diglyme.

Scheme 5

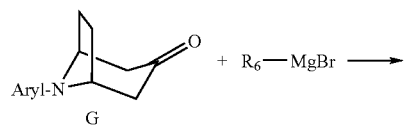

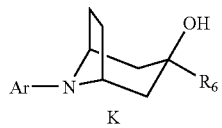

Examples for M

M1

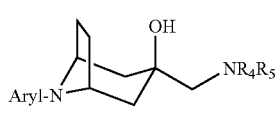

M2

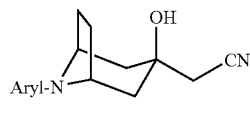

M3

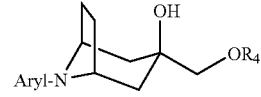

M4

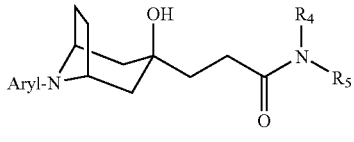

M6

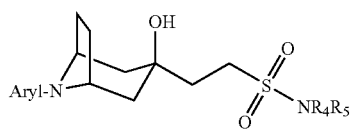

M5

Furthermore, the introduction of substituents on ring A or on the phenyl moiety can occur at any stage of the synthetic pathway, and thus ring A can be prepared first and its amine function reacted with a suitable phenyl precursor in a later step of the synthesis as shown in Scheme 6, in which the tropane derivative P exemplifies ring A as defined in Formula (I). The amine function may require transient protecting groups (PG) such as Boc, CBz, benzyl, p-methoxybenzyl.

Scheme 6

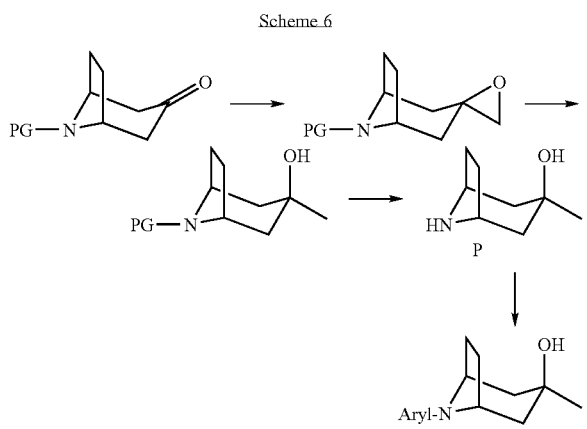

Where the processes for the preparation of the compounds according to the invention give rise to mixtures of stereoisomers, such isomers can be separated by conventional techniques such as preparative chiral chromatography. The compounds can be prepared in racemic form or individual enantiomers can be prepared by stereoselective synthesis or by resolution. The compounds can be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The compounds can also be resolved using a chiral auxiliary by formation of diastereomeric derivatives such as esters, amides or ketals followed by chromatographic separation and removal of the chiral auxiliary Methods of Use In some embodiments, compounds of Formula (I), as disclosed and described herein, are capable of modulating the activity of an androgen receptor.

The term "modulate" refers to the ability of a compound disclosed herein to alter the function of an androgen receptor. A modulator may activate the activity of an androgen receptor, may activate or inhibit the activity of an androgen receptor depending on the concentration of the compound exposed to the androgen receptor, or may inhibit the activity of an androgen receptor. The term "modulate" also refers to altering the function of an androgen receptor by increasing or decreasing the probability that a complex forms between an androgen receptor and a natural binding partner. A modulator may increase the probability that such a complex forms between the androgen receptor and the natural binding partner, may increase or decrease the probability that a complex forms between the androgen receptor and the natural binding partner depending on the concentration of the compound exposed to the androgen receptor, and or may decrease the probability that a complex forms between the androgen receptor and the natural binding partner. In some embodiments, modulation of the androgen receptor may be assessed using Receptor Selection and Amplification Technology (R-SAT) as described in U.S. Pat. No. 5,707,798, the disclosure of which is incorporated herein by reference in its entirety.

The term "activate" refers to increasing the cellular function of an androgen receptor. The term "inhibit" refers to decreasing the cellular function of an androgen receptor. The androgen receptor function may be the interaction with a natural binding partner or catalytic activity.

The term "contacting" as used herein refers to bringing a compound disclosed herein and a target androgen receptor together in such a manner that the compound can affect the activity of the androgen receptor, either directly; i.e., by interacting with the androgen receptor itself, or indirectly; i.e., by interacting with another molecule on which the activity of the androgen receptor is dependent. Such "contacting" can be accomplished in a test tube, a petri dish or the like. In a test tube, contacting may involve only a compound and a androgen receptor of interest or it may involve whole cells. Cells may also be maintained or grown in cell culture dishes and contacted with a compound in that environment. In this context, the ability of a particular compound to affect an androgen receptor related disorder; i.e., the $IC_{50}$ of the compound can be determined before use of the compounds in vivo with more complex living organisms is attempted. For cells outside the organism, multiple methods exist, and are well-known to those skilled in the art, to get the androgen receptors in contact with the compounds including, but not limited to, direct cell microinjection and numerous transmembrane carrier techniques. The term "contacting" can also refer to bringing a compound disclosed herein to contact with a target androgen receptor in vivo. Thus, if a compound disclosed herein, or a prodrug thereof, is administered to an organism and the compound is brought together with an androgen receptor within the organism, such contacting is within the scope of the present disclosure.

In some embodiments, a compound of Formula (I) may be an agonist of an androgen receptor, while in other embodiments, the compound may be an antagonist of an androgen receptor. In yet other embodiments, the compound may be a partial agonist of an androgen receptor. A compound that is a partial agonists may in some cases be a partial activator of a receptor, while in other cases may be a partial repressor of a receptor. In yet other circumstances, the compound may be a tissue-specific modulator, while in other circumstances, the compound may be a gene-specific modulator.

In one embodiment, an androgen receptor is activated by contacting it with a compound of Formula (I). The contacting of the androgen receptor may be in vivo or in vitro. When the receptor is contacted in vivo, the contacting may be accomplished by administering the compound to the living subject containing the receptor. In some embodiments, the living subject is a patient. In certain embodiments, the patient may be a mammal. The mammal may be selected from the group consisting of mice, rats, rabbits, guinea pigs, dogs, cats, sheep, goats, cows, primates, such as monkeys, chimpanzees, and apes, and humans. In some embodiments, the patient is a human.

Another aspect of the present invention is directed to a method of activating an androgen receptor comprising contacting the receptor with a compound of Formula (I).

Another aspect of the present invention is directed to a method of treating hypogonadism comprising identifying a patient inflicted with hypogonadism and administering to the patient a compound of Formula (I).

Another aspect of the present invention is directed to a method of treating a patient with lower than normal testosterone plasma levels comprising identifying a patient having less than normal testosterone plasma and administering to the patient a compound of Formula (I).

Another aspect of the present invention is directed to a method of treating infertility in males comprising identifying a male patient inflicted with infertility and administering to the patient a compound of Formula (I).

Another aspect of the present invention is directed to a method of modulating spermatogenesis in males by administering to a male patient a compound of Formula (I).

Another aspect of the present invention is directed to a method of treating erectile dysfunction in males comprising identifying a male patient inflicted with erectile dysfunction and administering to the patient a compound of Formula (I).

Another aspect of the present invention is directed to a method of treating andropause in males comprising identifying a male patient in a state of andropause and administering to the patient a compound of Formula (I).

Another aspect of the present invention is directed to a method of treating endometriosis in females comprising identifying a female patient inflicted with endometriosis and administering to the patient a compound of Formula (I).

Another aspect of the present invention is directed to a method of treating dyspareunia in females comprising identifying a female patient suffering from dyspareunia and administering to the patient a compound of Formula (I).

Another aspect of the present invention is directed to a method of treating vaginismus in females comprising identifying a female patient suffering from vaginismus and administering to the patient a compound of Formula (I).

Another aspect of the present invention is directed to a method of treating sexual arousal disorders in females comprising identifying a female patient inflicted with sexual arousal disorder and administering to the patient a compound of Formula (I).

Another aspect of the present invention is directed to a method of treating sexual orgasmic disorders in females comprising identifying a female patient inflicted with sexual orgasmic disorder and administering to the patient a compound of Formula (I).

Another aspect of the present invention is directed to a method of treating disorders of libido in males comprising identifying a male patient inflicted with a disorder of libido and administering to the patient a compound of Formula (I).

Another aspect of the present invention is directed to a method of hormonal replacement therapy comprising identifying a patient in need of hormonal replacement therapy and administering to the patient a compound of Formula (I). In one embodiment, the need for hormonal replacement therapy is caused by orchiectomy by surgical or chemical means.

Another aspect of the present invention is directed to a method of treating cachexia, HIV wasting, and critical illnesses in which muscle wasting is apparent comprising identifying a patient inflicted with muscle wasting and administering to the patient a compound of Formula (I).

Another aspect of the present invention is directed to a method of improving muscle strength in conditions including muscular dystrophy, myotonic dystrophy, glucocorticoid-treated asthma comprising identifying a patient in need of muscle strength improvement and administering to the patient a compound of Formula (I).

Another aspect of the present invention is directed to a method of treating a condition selected from the group consisting of sarcopenia; frailty; short stature; dwarfism; bone density loss; mood disorders including lack of well being, lack of vigor, anger, irritability, sadness, tiredness, and nervousness; depression; impaired cognitive functions including verbal fluency and spatial memory; neurodegenerative disorders, including Alzheimer's disease, Mild cognition impairment (MCI), Lewis body dementia, and frontal temporal dementia; xerophthalmia; metabolic disorders, including dyslipidemia, atherosclerosis, and non-insulin dependent diabetes (NIDDM); cardiovascular disorders including but not limited to hypertension, coronary artery disease, and myocardial perfusion; obesity; anemia; prostate cancer; and schizophrenia, comprising identifying a patient inflicted with at least one of these conditions and administering to the patient a compound of Formula (I).

Another aspect of the present invention is directed to a method of preventing a condition selected from the group consisting of bone density loss; xerophthalmia; metabolic disorders, including dyslipidemia, atherosclerosis, and non-insulin dependent diabetes (NIDDM); cardiovascular disorders including hypertension, coronary artery disease, and myocardial perfusion; obesity; and prostate cancer, comprising identifying a patient susceptible to at least one of these conditions and administering to the patient a compound of Formula (I).

Another aspect of the present invention is directed to a method of improving a health-related quality of life parameters selected from the group consisting of survival, impairment, functional status, health perception, and opportunities, comprising identifying a patient desiring an improvement in at least one of said parameters and administering to the patient a compound of Formula (I).

Still another aspect of the present invention is directed to a method of delaying the progression of prostate cancer comprising identifying a patient inflicted with prostate cancer and administering to the patient a compound of Formula (I).

In some embodiments, a compound of Formula (I) is particularly effective in treating certain conditions in male patients. Thus, the compound may be administered to the male patient in order to treat one or more of these conditions. In various embodiments, the condition treated in the male includes infertility, erectile dysfunction, andropause, and disorders of libido. In some embodiments, a compound of Formula (I) may be administered to a male patient in order to modulate spermatogenesis in the male patient.

In other embodiments, a compound of Formula (I) is particularly effective in treating certain conditions in female patients. Thus, the compound may be administered to the female patient in order to treat one or more of these conditions. In various embodiments, the condition treated in the female includes endometriosis, dyspareunia, vaginismus, sexual arousal disorder, and sexual orgasmic disorder.

In one embodiment, a compound of Formula (I) may be administered to a patient in order to effect hormone replacement.

In one embodiment, a compound of Formula (I) may be administered to a patient in order to improve muscle strength. For example, the compound may be administered to a patient in need of improvement in muscle strength due to muscular dystrophy, mytonic dystrophy, or glucocorticoid-treated asthma.

In one embodiment, a compound of Formula (I) may be administered to a patient in order to improve a health-related quality of life parameter such as survival, impairment, functional status, health perception, and opportunities.

In one embodiment, a compound of Formula (I) may be administered to a male patient suffering from prostate cancer in order to delay the progression of the prostate cancer.

Pharmaceutical Compositions

In another aspect, the present disclosure relates to a pharmaceutical composition comprising a physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa, 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections.

The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Ophthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delviery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrastemally, or the like, including infusion pump delivery; (d) administration locally such as by injection directly in the renal or cardiac area, e.g., by depot implantation; as well as (e) administration topically; as deemed appropriate by those of skill in the art for bringing the compound of the invention into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Non-limiting examples of appropriate in vitro animal models include castrated male rats or aged male orchidectomized rats. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

EXAMPLES

Chemical Synthesis

General procedures. $^1$H NMR spectra were recorded at 400 MHz on a Varian Mercury-VX400 MHz spectrometer or on a Bruker Ultrashield 300 MHz and chemical shifts are given in δ-values [ppm] referenced to the residual solvent peak chloroform ($CDCl_3$) at 7.26 and methanol ($CD_3OD$) at 3.31 ppm. Coupling constants, J, are reported in Hertz. Unless otherwise stated, the NMR spectra of the compounds are described for their free amine form. Acidic ion-exchange solid phase extraction (SPE) cartridges were MEGA BE-SCX from Varian. Materials and solvents were of the highest grade available from commercial sources and were used without further purification.

HPLC/LCMS Methods.

Analytical LCMS Method I

The analysis was performed on a combined prep/analytical Waters/Micromass system consisting of a ZMD single quadropole mass spectrometer equipped with electrospray ionization interface. The HPLC system consisted of a Waters 600 gradient pump with on-line degassing, a 2700 sample manager and a 996 PDA detector. Separation was performed on an X-Terra MS C18, 5 μm 4.6×50 mm column. Buffer A: 10 mM ammonium acetate in water, buffer B: 10 mM ammonium acetate in acetonitrile/water 95/5. A gradient was run from 30% B to 100% B in 7 min, hold at 100% B for 1 min and re-equilibrated for 5.5 min. The system was operated at 1 ml/min.

Analytical LCMS Method II

The analysis was performed on a Waters/Micromass LC/MS system consisting of a ZQ single quadropole mass spectrometer equipped with electro-spray ionization interface. The HPLC was a Waters 2795 Alliance HT system with a 996 PDA detector. Separation was performed on an X-Terra MS C18, 3.5 μg/m 4.6×30 mm column. Buffer A: 10 mM ammonium acetate in water, buffer B: 10 mM ammonium acetate in acetonitrile/water 95/5. A gradient was run from 30% B to 100% B in 5.5 min, stay at 100% B for 0.5 min, re-equilibrate for 2.5 min. System was operated at 1 mL/min.

Analytical LC/MS Method III

The analysis was performed on a combined prep/analytical Waters/Micromass system consisting of a ZMD single quadropole mass spectrometer equipped with electro-spray ionization interface. The HPLC system consisted of a Waters 600 gradient pump with on-line degassing, a 2700 sample manager and a 996 PDA detector.

Separation was performed on an YMC C18 J'sphere ODS H80, 5 μm 4.6×100 mm column. Buffer A: 0.15% TFA in water, buffer B: 0.15% TFA in acetonitrile/water 95/5. A gradient was run from 30% B to 100% B in 10 min, stay at 100% B for 2 min, re-equilibrate for 5 min. System was operated at 1 ml/min.

Preparative HPLC Purification Procedure.

Preparative purification was performed on a Waters auto purification system (600 pumps, 2700 sample manager, 996 PDA detector, ZMD mass spectrometer). The columns used were YMC C18 J'sphere ODS H80. Buffer A was 0.15% TFA in water, buffer B was 0.15% TFA in acetonitrile/water 95/5. The columns were operated at 17 mL/min. Following an initial hold of 2.5 min at 30% buffer B, compounds were separated using a gradient of 30-100% buffer B in 8.5 min.

Preparation of hydrochloride salts. Typically, the compounds were dissolved in dichloromethane, treated with an excess of 1 M HCl in diethylether and precipitated from n-heptane. The solvents were removed in vacuo and after drying, the hydrochloride salts were obtained as solids.

Method A

3,5-Dimethyl-4-(4-nitronaphthalen-1-yl)piperidine (116BG35-5)

A Pyrex tube was charged with 1-chloro-4-nitronaphthalene (52 mg, 0.25 mmol) and 3,5-dimethylpiperidine (133 µL, 1.0 mmol) followed by acetonitrile (2 mL). The tube was capped and the reaction tube was exposed to microwave irradiation (180° C., 5 min). The reaction mixture was filtered and the solid washed with cold ethanol. If needed the compound was purified according to Purification method C. Yield: 58 mg (82%).

Major isomer: LCMS m/z 285 [M+H]$^+$. HPLC $t_R$=16.9 min (method III). $^1$H-NMR (CD$_3$OD, 400 MHz) δ 8.58-8.55 (m, 1H), 8.16 (d, J=8.4, 1H), 8.07 (m, 1H), 7.59-7.54 (m, 1H), 7.49-7.44 (m, 1H), 6.89 (d, J=8.4, 1H), 3.35-3.31 (m, 1H), 2.24 (t, J=11.6, 2H), 2.0-1.85 (m, 2H), 1.85-1.79 (m, 1H), 0.85 (t, J=11.6, 2H), 0.68 (q, J=11.6, 1H)

Minor isomer: LCMS m/z 285 [M+H]$^+$. HPLC $t_R$=16.8 min (method III). $^1$H-NMR (CD$_3$OD, 400 MHz) δ 8.58-8.55 (m, 1H), 8.19-8.18 (m, 1H), 8.07 (m, 1H), 7.59-7.54 (m, 1H), 7.49-7.44 (m, 1H), 6.90 (d, J=8.4, 1H), 3.10-3.03 (m, 2H), 2.75-2.63 (m, 2H), 2.18 (m, 2H), 1.43 (t, J=5.7, 2H), 1.03 (d, J=6.6, 1H).

Method B

1-(4-Cyanonaphthalen-1-yl)piperidine-3-carboxylic acid diethylamide (136BG73-4)

A solution of 1-cyano-4-fluoronaphthalene in pyridine (0.6 M, 1 mL) was transferred to a Pyrex tube and N,N-diethylnipecotamide (447 mg, 2.4 mmol) was added. The tube was capped and the reaction tube was exposed to microwave irradiation (220° C., 10 min). The reaction mixture was concentrated and purified according to Purification Method A.

LCMS m/z 336 [M+H]$^+$. HPLC $t_R$=9.0 min (method I). $^1$H-NMR (CD$_3$OD, 400 MHz) δ 8.15 (d, J=8.2, 1H), 8.00 (d, J=8.2, 1H), 7.77 (d, J=7.8, 1H), 7.60-7.52 (m, 2H), 7.05 (d, J=7.8, 1H), 3.60-3.36 (m, 4H), 3.36-3.21 (m, 1H), 3.21-3.10 (m, 1H), 3.03-2.92 (m, 1H), 2.78-2.65 (m, 1H), 2.08-1.83 (m, 4H), 1.78-1.60 (m, 1H), 1.30-1.16 (m, 3H), 1.07 (t, J=7.04, 3H). $^{13}$C-NMR (CD$_3$OD, 100 MHz) 173.9, 155.1, 133,7, 133.6, 128.4, 128.1, 126.6, 125.1, 124.5, 118.1, 114.1, 103.6, 56.1, 53.7, 42.3, 40.4, 39.9, 27.8, 25.0, 14.2, 12.2.

Purification Method A

The concentrated crude material was taken up in ethyl acetate and extracted with 2 M HCl. The organic phase was then dried over Na$_2$SO$_4$, filtered and concentrated in vacuo.

Purification Method B

The concentrated crude material was taken up in ethyl acetate and extracted with 2 M HCl. The organic phase was then dried over Na$_2$SO$_4$, filtered, concentrated in vacuo and purified by preparative HPLC. (40% A; 80% B, NH$_4$OAc)

Purification Method C

The concentrated crude material was purified by preparative HPLC.

2,6-Dimethyl-4-(4-nitronaphthalen-1-yl)morpholine (116BG35-23)

Prepared according to Method A. Major isomer: LCMS m/z 287 [M+H]$^+$. HPLC $t_R$=11.1 min (method I). Minor isomer: LCMS m/z 287 [M+H]$^+$. HPLC $t_R$=10.7 min (method I).

1-(4-Nitronaphthalen-1-yl)-4-pyrrolidin-1-yl-piperidine (116BG35-2)

Prepared according to Method A. LCMS m/z 326 [M+H]$^+$. HPLC $t_R$=1.7 min (method III). Yield: 51%.

1-(4-Nitronaphthalen-1-yl)piperidine (116BG35-6)

Prepared according to Method A. LCMS m/z 257 [M+H]$^+$. HPLC $t_R$=13.5 min (method III). Yield: 79%.

4-Methyl-4-(4-nitronaphthalen-1-yl)piperidine (116BG35-7)

Prepared according to Method A. LCMS m/z 271 [M+H]$^+$. HPLC $t_R$=14.8 min (method I). Yield: 66%.

1-(4-Nitronaphthalen-1-yl)piperidine-4-carboxylic acid ethyl ester. (116BG35-1)

Prepared according to Method A. Purified according to Purification Method C. LCMS, m/z 329 [M+H]$^+$. HPLC $t_R$=12.1 min (method III). Yield: 16%.

4-(4-Nitronaphthalen-1-yl)morpholine (116BG35-10)

Prepared according to Method A. Purified according to Purification method C. LCMS m/z 259 [M+H]$^+$. HPLC $t_R$=8.0 min (method III). Yield: 8%.

2,5-Dimethyl-4-(4-nitronaphthalen-1-yl)pyrrolidine (116BG35-24)

Prepared according to Method A. Purified according to Purification method C. LCMS m/z 271 [M+H]$^+$. HPLC $t_R$=10.4 min (method III). Yield: 7%.

4-(3-Hydroxymethylpiperidin-1-yl)naphthalene-1-carbonitrile (136BG73-1)

Prepared according to Method B. Purified according to Purification method A. LCMS m/z 267 [M+H]$^+$. HPLC $t_R$=7.9 min (method I).

4-[4-(2-Hydroxyethyl)piperidin-1-yl]naphthalene-1-carbonitrile (136BG73-9)

Prepared according to Method B. Purified according to Purification method A. LCMS m/z 281 [M+H]$^+$. HPLC $t_R$=8.3 min (method III).

4-Piperidin-1-ylnaphthalene-1-carbonitrile (136BG73-10)

Prepared according to Method B. Purified according to Purification method B. LCMS m/z 237 [M+H]$^+$. HPLC $t_R$=10.5 min (method I).

4-(4-Methylpiperidin-1-yl)naphthalene-1-carbonitrile (136BG73-11)

Prepared according to Method B. Purified according to Purification method C. LCMS m/z 251 [M+H]$^+$. HPLC $t_R$=15.9 min (method III).

4-(4-Hydroxypiperidin-1-yl)naphthalene-1-carbonitrile (136BG73-12)

Prepared according to Method B. Purified according to Purification method C. LCMS m/z 253 [M+H]$^+$. HPLC $t_R$=9.3 min (method III).

4-(4-Hydroxymethylpiperidin-1-yl)naphthalene-1-carbonitrile (136BG73-13)

Prepared according to Method B. Purified according to Purification method B. LCMS m/z 267 [M+H]$^+$. HPLC $t_R$=7.6 min (method I).

1-(4-Cyanonaphthalen-1-yl)piperidine-4-carboxylic acid amide (136BG73-17)

Prepared according to Method B. Purified according to Purification method C. LCMS m/z 280 [M+H]$^+$. HPLC $t_R$=8.4 min (method III).

N-[1-(4-Cyanonaphthalen-1-yl)pyrrolidin-3-yl]-N-methylacetamide (136BG73-18)

Prepared according to Method B. Purified according to Purification method C. LCMS m/z 294 [M+H]$^+$. HPLC $t_R$=9.5 min (method III).

4-(3-Dimethylaminopyrrolidin-1-yl)naphthalene-1-carbonitrile (136BG73-19)

Prepared according to Method B. Purified according to Purification method C. LCMS m/z 266 [M+H]$^+$. HPLC $t_R$=3.8 min (method I). $^1$H-NMR (CD$_3$OD, 400 MHz) δ 8.26-8.22 (m, 1H), 8.02-7.99 (m, 1H), 7.70 (d, J=8.4, 1H), 7.61-7.65 (m, 1H), 7.49-7.45 (m, 1H), 6.75 (d, J=8.2, 1H), 3.72-3.65 (m, 1H), 3.58-3.47 (m, 3H), 2.93-2.82 (m, 1H), 2.33 (s, 6H), 2.28-2.20 (m, 1H), 1.94-1.83 (m, 1H). $^{13}$C-NMR (CD$_3$OD, 100 MHz) δ 151.7, 134.6, 133.7, 128.0, 125.9, 125.5, 124.8, 124.8, 119.1, 108.4, 98.4, 65.4, 56.6, 51.6, 43.2, 29.8.

4-(3-Hydroxypiperidin-1-yl)naphthalene-1-carbonitrile (136BG73-25)

Prepared according to Method B. Purified according to Purification method C. LCMS m/z 253 [M+H]$^+$. HPLC $t_R$=7.2 min (method I).

4-(2,6-Dimethylmorpholin-4-yl)naphthalene-1-carbonitrile (136BG73-26)

Prepared according to Method B. Purified according to Purification method C. LCMS m/z 267 [M+H]$^+$. HPLC $t_R$=9.3 min (method III).

4-(3-Hydroxypyrrolidin-1-yl)naphthalene-1-carbonitrile (136BG85-2)

1-Cyano-4-fluoronaphthalene (86 mg, 0.5 mmol) was transferred to a Pyrex tube and 3-pyrrolidinol (162 μL, 2.0 mmol) was added followed by toluene (0.5 mL). The tube was capped and the reaction tube was exposed to microwave irradiation (180° C., 5 min). The reaction mixture was concentrated and purified by re-crystallization with EtOH. Yield: 51 mg (43%).

LCMS m/z 239 [M+H]$^+$. HPLC $t_R$=6.0 min (method I). $^1$H-NMR (CD$_3$OD, 400 MHz) δ 8.36-8.33 (m, 1H), 7.97-7.95 (m, 1H), 7.83 (d, J=8.4, 1H), 7.70-7.65 (m, 1H), 7.53-7.48 (m, 1H), 6.74 (d, J=8.4, 1H), 5.05 (d, J=3.2, 1H), 4.10 (s, 1H), 3.93-3.89 (m, 1H), 3.85-3.78 (m, 1H), 3.55-3.49 (m, 1H), 2.10-2.02 (m, 1H), 2,02-1,90 (m, 1H). $^{13}$C-NMR (CD$_3$OD, 100 MHz) δ 152.4, 135.1, 135.0, 129.3, 127.3, 125.4, 125.4, 125.1, 120.4, 108.3, 96.5, 70.1, 62.0, 51.0, 34.5.

4-((S)-2-Hydroxymethylpyrrolidin-1-yl)naphthalene-1-carbonitrile (136BG85-3-3)

1-Cyano-4-fluoronaphthalene (86 mg, 0.5 mmol) was transferred to a Pyrex tube and L-prolinol (197 μL, 2.0 mmol) was added followed by toluene (0.5 mL). The tube was capped and the reaction tube was exposed to microwave irradiation (180° C., 5 min). The reaction mixture was concentrated and purified by flash chromatography on silica gel (eluent: 0-3% methanol in dichloromethane). Yield: 23 mg (18%).

LCMS m/z 253 [M+H]$^+$. HPLC $t_R$=7.3 min (method I). $^1$H-NMR (CD$_3$OD, 400 MHz) δ 8.30 (d, J=8.6, 1H), 8.08-8.05 (m, 1H), 7.80 (d, J=8.2, 1H), 7.67-7.63 (m, 1H), 7.56-7.51 (m, 1H), 7.07 (d, J=8.2, 1H), 4.21-4.15 (m, 1H), 4.10-4.00 (m, 1H), 3.68-3.64 (m, 1H), 3.55-3.50 (m, 1H), 3.36-3.30 (m, 1H), 2.40-2.29 (m, 1H), 2.10-1.98 (m, 2H), 1.90-1.71 (m, 1H). $^{13}$C-NMR (CD$_3$OD, 100 MHz) δ 153.5, 135.7, 134.6, 129.3, 128.6, 127.4, 126.1, 125.9, 120.1, 111.5, 100.4, 63.8, 62.4, 57.6, 30.2, 26.1.

4-Pyrrolidin-1-ylnaphthalene-1-carbonitrile (136BG65-3)

1-Cyano-4-fluoronaphthalene (2.0 g, 11.7 mmol) was transferred to a 25 mL flask and pyrrolidine (4.0 mL) was added. The reaction mixture was stirred for 15 min where after the product precipitated out. The reaction mixture was concentrated in vacuo. The solid was then re-crystallized with MeOH and the crystals washed with EtOH. Yield: 1.6 g (62%).

LCMS m/z 223 [M+H]$^+$. HPLC $t_R$=9.7 min (method I). $^1$H-NMR (CD$_3$OD, 400 MHz) δ 8.38-8.35 (m, 1H), 8.05-8.02 (m, 1H), 7.75 (d, J=8.2, 1H), 7.64-7.60 (m, 1H), 7.51-7.45 (m, 1H), 6.80 (d, J=8.2, 1H), 3.65-3.61 (m, 4H), 2.07-2.03 (m, 4H). $^{13}$C-NMR (CD$_3$OD, 100 MHz) δ 152.6, 135.2, 134.1, 128.2, 126.6, 125.8, 125.0, 124.6, 119.6, 108.0, 97.4, 53.0, 25.9.

4-Pyrrolidin-1-ylnaphthalene-1-carboxylic acid ethyl ester (154BG19)

4-Fluoro-1-naphthoic acid (190 mg, 1.0 mmol) was transferred to a Pyrex tube and ethanol (0.6 mL) was added followed by conc. sulphuric acid (0.1 mL). The tube was capped and the reaction tube was exposed two times to microwave irradiation (2×120° C., 5 min). The reaction mixture was transferred to a separation funnel with ethyl acetate and washed with 2 M NaOH. The aqueous phase was acidified with 2 M HCl and extracted with ethyl acetate. The organic phases were collected, dried over Na$_2$SO$_4$, filtered and concentrated to yield 4-fluoronaphthalene-1-carboxylic acid ethyl ester (154BG85-11, 156 mg, 72%).

$^1$H-NMR (CD$_3$OD, 400 MHz) δ 8.89-8.85 (m, 1H), 8.06 (dd, J=5.7, 8.2, 1H), 7.59-7.54 (m, 1H), 7.53-7.48 (m, 1H), 7.09 (dd, J=8.2, 10.2, 1H), 4.36 (q, J=6.8, 2H), 1.38 (t, J=6.8, 3H).

154BG85-11 (156 mg, 0.7 mmol) was transferred to a Pyrex tube and pyrrolidine (1 mL) was added. The tube was capped and the reaction tube was exposed to microwave irradiation (100° C., 3 min). The microwave exposure was repeated for 5 min at 130° C. The pyrrolidine was evaporated and the reaction mixture was transferred to a separation funnel with ethyl acetate and washed with 2 M NaOH. The aqueous phase was acidified with 2 M HCl and extracted with ethyl acetate. The organic phases were collected, dried over Na$_2$SO$_4$, filtered and concentrated to yield 135 mg (70%) of the title compound.

LCMS m/z 270 [M+H]$^+$. HPLC $t_R$=7.3 min (method I). $^1$H-NMR (CDCl$_3$, 400 MHz) δ 9.11-9.09 (m, 1H), 8.25-8.22 (m, 1H), 8.17 (d, J=8.4, 1H), 7.58-7.54 (m, 1H), 7.44-7.40 (m, 1H), 6.81 (d, J=8.4, 1H), 4.43 (q, J=7.0, 2H), 3.57-3.53 (m, 4H), 2.05-2.01 (m, 4H), 1.44 (t, J=7.0, 3H). $^{13}$C-NMR (CDCl$_3$, 100 MHz) δ 167.8, 134.1, 132.1, 127.5, 126.7, 126.3, 125.5, 123.9, 108.3, 60.5, 53.2, 25.7, 14.7.

4-Pyrrolidin-1-ylnaphthalene-1-carboxylic acid (154BG23)

154BG19 (30 mg, 0.11 mmol) was transferred to a Pyrex tube and LiOH×H$_2$O (14 mg, 0.33 mmol) was added, followed by H$_2$O (0.18 mL) and THF (0.37 mL). The tube was capped and the reaction tube was exposed to microwave irradiation (160° C., 5 min). The reaction mixture was transferred to a separation funnel with ethyl acetate and washed with 2 M NaOH. The aqueous phase was acidified with 2 M HCl and extracted with ethyl acetate. The organic phases were collected, dried over Na$_2$SO$_4$, filtered and concentrated to yield 18 mg (68%) of the title compound.

LCMS m/z 240 [M-H]$^-$. LCMS m/z 242 [M+H]$^+$. HPLC $t_R$=3.2 min (method I). $^1$H-NMR (DMSO-d$_6$, 400 MHz) δ 9.09-9.07 (m, 1H), 8.26-8.23 (m, 1H), 8.09 (d, J=8.4, 1H), 7.73-7.68 (m, 1H), 7.66-7.62 (m, 1H), 6.83 (d, J=8.4, 1H), 3.53-3.49 (m, 4H), 1.99-1.95 (m, 4H). $^{13}$C-NMR (DMSO-d$_6$, 100 MHz) δ 169.1, 152.4, 134.3, 132.8, 127.7, 126.4, 126.4, 126.1, 124.1, 108.3, 53.1, 25.8.

4-(3-endo-Hydroxy-8-azabicyclo[3.2.1]oct-8-yl)naphthalene-1-carbonitrile (154BG31)

1-Cyano-4-fluoronapthalene (104 mg, 0.6 mmol), nortropanol (305 mg, 2.4 mmol) and pyridine (93 μL, 0.6 mmol) were transferred to a Pyrex tube. The tube was capped and the reaction tube was exposed to microwave irradiation (220° C., 5 min). The mixture was transferred to a separation funnel with ethyl acetate and with 2 M HCl and the organic phases were then washed with brine. The organic layer was collected, dried over Na$_2$SO$_4$, filtered and concentrated to yield 157 mg (92%) of the title compound.

LCMS m/z 279 [M+H]$^+$. HPLC $t_R$=6.8 ml (method I). $^1$H-NMR (CDCl$_3$, 400 MHz) δ 8.21-8.16 (m, 2H), 7.75 (d, J=8.0, 1H), 7.66-7.62 (m, 1H), 7.65-7.52 (m, 1H), 6.90 (d, J=8.0, 1H), 4.32 (t, J=5.1, 1H), 4.14-4.11 (m, 2H), 2.51-2.45 (m, 2H), 2.34-2.28 (m, 2H), 2.02-1.96 (m, 4H). $^{13}$C-NMR (CDCl$_3$, 100 MHz) δ 153.1, 134.5, 133.7, 128.4, 127.9, 126.0, 125.9, 125.4, 119.1, 111.0, 102.0, 65.2, 60.1, 40.7, 27.4.

Alternatively, 154BG31 was prepared by the following procedure: 1-Cyano-4-fluoronaphthalene (20.0 g, 117 mmol) was dissolved in pyridine (100 mL). A solution of nortropine (59.4 g, 467 mmol) in pyridine (100 mL) was added, and the reaction mixture was heated to reflux for 20 hours. The resulting black solution was concentrated, and water (800 mL) was added. The pH was adjusted to 1 by addition of 2 M HCl. The product was extracted into dichloromethane (2×800 mL), and the combined organic phases were washed with 0.5 M NaOH (400 mL), dried over sodium sulfate, filtered and evaporated. The crude product was dissolved in hot ethyl acetate (200 mL), and crystallization occurred upon cooling to rt. Crystallization was continued at 5° C. for 20 hours. Filtration afforded a first crop of the title compound (21.2 g, 65% yield) as a white solid. The mother liquors contained more product (as shown by LC-MS), but re-crystallization of the mother liquors was not pursued further.

4-(3-Oxo-8-azabicyclo[3.2.1]oct-8-yl)naphthalene-1-carbonitrile (156AF03-217)

A solution of oxalyl chloride (440 μL, 5.11 mmol) in anhydrous dichloromethane (3 mL) was added dropwise to a cold solution of dry dimethylsulfoxide (726 μL, 10.22 mmol) in dichloromethane (5 mL) at −60° C. under argon atmosphere. A solution of 154BG31 (647 mg, 2.32 mmol) in dry dichloromethane (7 mL) was added dropwise to the cold reaction mixture. The mixture was allowed to warm up to −40° C. over 50 min. Afterwards the mixture was cooled to −60° C. and triethylamine (1.90 mL, 13.92 mmol) was added dropwise. The mixture was allowed to warm up to rt slowly and stirring was continued overnight at rt. The mixture was partitioned between dichloromethane and water. The organic layer was dried over sodium sulfate, filtered and evaporated to dryness. Purification of the residue by silica gel column chromatography, eluting with a mixture of ethyl acetate and n-heptane (50:50), afforded the desired compound (0.55 g, 86%).

R$_f$=0.51 (Ethyl acetate/n-Heptane 50:50). LCMS m/z 277 [M+H]$^+$. HPLC $t_R$=10.9 (method III). $^1$H NMR (CDCl$_3$, 400 MHz) δ 8.27-8.21 (m, 2H, Ar—H), 7.79 (d, 1H, J=8.0, Ar—H), 7.68 (m, 1H, Ar—H), 7.61(m, 1H, Ar—H), 6.93 (d, 1H, J=8.0, Ar—H), 4.39 (m, 2H, Tr—H), 3.03 (m, 2H, Tr—H), 2.53 (m, 2H, Tr—H), 2.20 (m, 2H, Tr—H). 1.85 (m, 2H, Tr—H).

4-(3-Propylamino-8-azabicyclo[3.2.1]oct-8-yl)naphthalene-1-carbonitrile, hydrochloride (156AF01-222 & 156AF01-223)

n-Propylamine (54 µL, 0.65 mmol) and acetic acid (50 µL, 0.87 µmol) were added to a solution of 156AF03-217 (64 mg, 0.23 mmol) in THF (1 mL). After 1 h stirring at rt a solution of sodium cyanoborohydride (33 mg, 0.52 mmol) in methanol (2 mL) was added. The reaction mixture was stirred in a sealed flask for 20 min at 110° C. The solvent was removed by evaporation and the residue partitioned between dichloromethane and water. The organic layer was evaporated to dryness and the residue was purified by passage over an acidic ion-exchange cartridge. Separation of the diastereomers (endo/exo 41:59) was performed by column chromatography on silica gel eluting with a stepwise gradient of 5-10% methanol in dichloromethane. The two diastereomers were converted to the corresponding hydrochloride salt as described above.

Endo-diastereomer 156AF01-222: $R_f$=0.34 (MeOH/$CH_2Cl_2$ 10:90). LCMS m/z 320 [M+H]$^+$. HPLC $t_R$=2.8 min (method II). $^1$H NMR (CDC$_3$, 400 MHz) δ 8.21 (d, 1H, J=8.0, Ar—H), 8.15 (d, 1H, J=8.0, Ar—H), 7.72 (d, 1H, J=8.0, Ar—H), 7.62 (m, 1H, Ar—H), 7.53 (m, 1H, Ar—H), 6.86 (d, 1H, J=8.0, Ar—H), 4.09 (m, 2H, Tr—H), 3.13 (m, 1H, Tr—H), 2.61 (t, 2H, J=7.2, NCH$_2$CH$_2$CH$_3$), 2.45-2.38 (m, 2H, Tr—H), 2.18 (m, 2H, Tr—H), 1.98-1.92 (m, 2H, Tr—H), 1.78 (m, 2H, Tr—H), 1.52 (h, 2H, J=7.2, NCH$_2$CH$_2$CH$_3$), 0.96 (t, 3H, J=7.2, NCH$_2$CH$_2$CH$_3$).

Exo-diastereomer 156AF01-223: $R_f$=0.19 (MeOH/$CH_2Cl_2$ 10:90). LCMS m/z 320 [M+H]$^+$. HPLC $t_R$=4.1 min (method II). $^1$H NMR (CDCl$_3$, 400 MHz) δ 8.21 (d, 1H, J=8.0, Ar—H), 8.15 (d, 1H, J=8.0, Ar—H), 7.72 (d, 1H, J=8.0, Ar—H), 7.62 (m, 1H, Ar—H), 7.53 (m, 1H, Ar—H), 6.86 (d, 1H, J=8.0, Ar—H), 4.17 (m, 2H, Tr—H), 3.04 (m, 1H, Tr—H), 2.64 (t, 2H, J=7.2, NCH$_2$CH$_2$CH$_3$), 2.11-2.00 (m, 4H, Tr—H), 1.85-1.75 (m, 4H, Tr—H), 1.54 (h, 2H, J=7.2, NCH$_2$CH$_2$CH$_3$), 0.96 (t, 3H, J=7.2, NCH$_2$CH$_2$CH$_3$)

4-(3-Dimethylamino-8-azabicyclo[3.2.1]oct-8-yl) naphthalene-1-carbonitrile, hydrochloride (156AF05-224)

Dimethylamine (200 µL, 0.40 mmol) and acetic acid (50 µL, 0.87 µmol) were added to a solution of 156AF03-217 (56 mg, 0.20 mmol) in a mixture of THF and methanol (1:1, 2 mL). The mixture was stirred in a sealed flask for 10 min under microwave irradiation at 110° C. A solution of sodium cyanoborohydride in methanol (300 µL) was added to the reaction mixture at rt. The mixture was stirred in a sealed flask for 18 min under microwave irradiation at 110° C. The solvent was removed and the residue partitioned between dichloromethane and water. The organic layer was evaporated to dryness. Purification of the residue by silica gel column chromatography, eluting with stepwise gradient of 5-10% methanol in dichloromethane, afforded the desired product as a diastereomeric mixture—ratio 80:20 (27 mg, 44%). The product was converted to the corresponding hydrochloride salt as described above.

$R_f$=0.18 (MeOH/$CH_2Cl_2$ 10:90). LCMS m/z 306 [M+H]$^+$. HPLC $t_R$=2.5 min (method II).

4-[3-(3-Hydroxypropylamino)-8-azabicyclo[3.2.1] oct-8-yl]naphthalene-1-carbonitrile, hydrochloride (156AF07-225)

The product was synthesized from 3-amino-1-propanol (31 mg, 0.41 mmol) and 156AF03-217 (57 mg, 0.21 mmol) using the same method as for the preparation of 156AF05-224. The product was isolated as a diastereomeric mixture (11 mg, 16%). The product was converted to the corresponding hydrochloride salt as described above.

$R_f$=0.22 (MeOH/$CH_2Cl_2$ 10:90). LCMS m/z 336 [M+H]$^+$. HPLC $t_R$=2.6 min (method II).

4-[3-(2-Ethoxyethylamino)-8-azabicyclo[3.2.1]oct-8-yl]naphthalene-1-carbonitrile, hydrochloride (156AF09-226 & 156AF09-227)

The title compound was synthesized from 2-ethoxyethylamine (35 mg, 0.40 mmol) and 156AF03-217 (54 mg, 0.19 mmol) using the same method as for the preparation of 156AF05-224. Separation of the diastereomers (endo/exo 41:59) was performed by column chromatography on silica gel eluting with a stepwise gradient of 5-10% methanol in dichloromethane. The products were converted to the corresponding hydrochloride salt as described above.

Endo-diastereomer 156AF09-226: $R_f$=0.46 (MeOH/$CH_2Cl_2$ 10:90). LCMS m/z 350 [M+H]$^+$. HPLC $t_R$=4.9 min (method II). $^1$H NMR (CDCl$_3$, 400 MHz) δ 8.21 (d, 1H, J=8.0, Ar—H), 8.16 (d, 1H, J=8.0, Ar—H), 7.72 (d, 1H, J=8.0, Ar—H), 7.63 (m, 1H, Ar—H), 7.54 (m, 1H, Ar—H), 6.87 (d, 1H, J=8.0, Ar—H), 4.10 (m, 2H, Tr—H), 3.59-3.49 (m, 4H, CH$_2$O), 3.16 (m, 1H, Tr—H), 2.83 (m, 2H, NCH$_2$), 2.46-2.40 (m, 2H, Tr—H), 2.22-2.15 (m, 2H, Tr—H), 1.96 (m, 2H, Tr—H), 1.82 (m, 2H, Tr—H), 1.24 (t, 3H, J=7.2, OCH$_2$CH$_3$).

Exo-diastereomer 156AF09-227: $R_f$=0.25 (MeOH/$CH_2Cl_2$ 10:90). LCMS m/z 350 [M+H]$^+$. HPLC $t_R$=5.9 min (method II). $^1$H NMR (CDCl$_3$, 400 MHz) δ 8.16 (d, 1H, J=8.0, Ar—H), 8.08 (d, 1H, J=8.0, Ar—H), 7.65 (d, 1H, J=8.0, Ar—H), 7.55 (m, 1H, Ar—H), 7.45 (m, 1H, Ar—H), 6.80 (d, 1H, J=8.0, Ar—H), 4.11 (m, 2H, Tr—H), 3.56-3.44 (m, 4H, CH$_2$O), 3.10 (m, 1H, Tr—H), 2.84 (m, 2H, NCH$_2$), 2.09-1.69 (m, 8H, Tr—H), 1.15 (t, 3H, J=7.2, OCH$_2$CH$_3$).

4-{3-[2-(1H-Imidazol-4-yl)ethylamino]-8-azabicyclo [3.2.1]oct-8-yl}naphthalene-1-carbonitrile, dihydrochloride (156AF11-229)

A solution of histamine (16 mg, 0.14 mmol) in methanol (1 mL) was added dropwise to a solution of 156AF03-217 (20 mg, 72.4 µmmol) in THF (0.5 mL) followed by addition of acetic acid (25 µL, 0.43 mmol). After 2 hours stirring at rt a solution of sodium cyanoborohydride (10 mg, 0.16 mmol) in methanol (0.10 mL) was added. The reaction mixture was shaken overnight at 48° C. The solvent was removed and the residue was partitioned between dichloromethane and 1 M aqueous sodium hydroxide. The organic layer was evaporated to dryness to give the desired product as a diastereomeric mixture, ratio 60:40. The product was converted to the corresponding hydrochloride salt as described above.

LCMS m/z 372 [M+H]$^+$. HPLC $t_R$=3.1 & 3.9 min (method I).

4-(3-Cyclopropylamino-8-azabicyclo[3.2.1]oct-8-yl) naphthalene-1-carbonitrile, hydrochloride (156AF11-230)

The title compound (diastereomers, ratio 28:72) was synthesized from cyclopropylamine (8.3 mg, 0.14 mmol) and 156AF03-217 (20 mg, 72.4 µmol) using the same method as for the preparation of 156AF11-229. The product was converted to the corresponding hydrochloride salt as described above.

4-[3-(2-Dimethylaminoethylamino)-8-azabicyclo[3.2.1]oct-8-yl]naphthalene-1-carbonitrile, dihydrochloride (156AF11-231)

The title compound (diastereomers, ratio 45:55) was synthesized from N,N-dimethylethylene diamine (13 mg, 0.15 mmol) and 156AF03-217 (20 mg, 72.4 µmol) using the same method as for the preparation of 156AF11-229. The product was converted to the corresponding hydrochloride salt as described above.

LCMS m/z 349 [M+H]$^+$. HPLC $t_R$=4.7 & 6.0 min (method I).

4-[3-(Cyclohexylmethylamino)-8-azabicyclo[3.2.1]oct-8-yl]naphthalene-1-carbonitrile, hydrochloride (156AF11-232)

The title compound (diastereomers, ratio 47:53) was synthesized from aminomethylcyclohexane (16 mg, 0.15 mmol) and 156AF03-217 (20 mg, 72.4 µmol) using the same method as for the preparation of 156AF11-229. The product was converted to the corresponding hydrochloride salt as described above.

LCMS m/z 374 [M+H]$^+$. HPLC $t_R$=7.7 & 9.1 min (method I).

4-{3-[(Furan-2-ylmethyl)amino]-8-azabicyclo[3.2.1]oct-8-yl}naphthalene-1-carbonitrile, hydrochloride (156AF11-233)

The title compound (diastereomers, ratio 65:35) was synthesized from furfurylamine (14 mg, 0.15 mmol) and 156AF03-217 (20 mg, 72.4 µmol) using the same method as for the preparation of 156AF11-229. The product was converted to the corresponding hydrochloride salt as described above.

LCMS m/z 358 [M+H]$^+$. HPLC $t_R$=7.5 & 9.8 min (method I).

4-[3-(2-Morpholin-4-ylethylamino)-8-azabicyclo[3.2.1]oct-8-yl]naphthalene-1-carbonitrile, dihydrochloride (156AF11-234)

The title compound (diastereomers, ratio 38:62) was synthesized from 4-(2-aminoethyl)morpholine (19 mg, 0.15 mmol) and 156AF03-217 (20 mg, 72.4 µmol) using the same method as for the preparation of 156AF 11-229. The product was converted to the corresponding hydrochloride salt as described above.

LCMS m/z 391 [M+H]$^+$. HPLC $t_R$=4.2 & 5.5 min (method I).

4-{3-[(Pyridin-2-ylmethyl)amino]-8-azabicyclo[3.2.1]oct-8-yl}naphthalene-1-carbonitrile, dihydrochloride (156AF11-235)

The title compound (diastereomers, ratio 49:51) was synthesized from 2-(aminomethyl)pyridine (16 mg, 0.15 mmol) and 156AF03-217 (20 mg, 72.4 µmol) using the same method as for the preparation of 156AF 11-229. The product was converted to the corresponding hydrochloride salt as described above.

LCMS m/z 369 [M+H]$^+$. HPLC $t_R$=6.7 & 8.6 min (method I).

4-[3-(2-Isopropoxyethylamino)-8-azabicyclo[3.2.1]oct-8-yl]naphthalene-1-carbonitrile, hydrochloride (156AF11-237)

The title compound (diastereomers, ratio 42:58) was synthesized from 2-aminoethyl isopropyl ether (15 mg, 0.15 mmol) and 156AF03-217 (20 mg, 72.4 µmol) using the same method as for the preparation of 156AF11-229. The product was converted to the corresponding hydrochloride salt as described above.

LCMS m/z 364 [M+H]$^+$. HPLC $t_R$=6.7 & 7.7 min (method I).

4-(1,4-Dioxa-8-azaspiro[4.5]dec-8-yl)naphthalene-1-carbonitrile (156AF14-239)

1.4-dioxa-8-azaspiro[4.5]decane (332 mg, 2.32 mmol) was added to a solution of 1-cyano-1-fluoronaphthalene (120 mg, 0.70 mmol) in anhydrous THF (1 mL). After 48 hours stirring at rt the mixture was partitioned between ethyl acetate and water. The organic layer was dried over sodium sulfate, filtered and evaporated to dryness. The residue was washed with a mixture of ethyl acetate and n-heptane (50:50). Purification by silica gel column chromatography, eluting with 5% methanol in dichloromethane afforded the desired compound (126 mg, 43%). The compound was converted to the corresponding hydrochloride salt as described above.

$R_f$=0.45 (ethyl acetate/n-heptane 50:50). LCMS m/z 295 [M+H]$^+$. HPLC $t_R$=12.3 min (method I). $^1$H NMR (CDCl$_3$, 400 MHz) δ 8.21-8.15 (m, 2H, Ar—H), 7.82 (d, 1H, J=8.0, Ar—H), 7.65 (m, 1H, Ar—H), 7.58 (m, 1H, Ar—H), 7.04 (d, 1H, J=8.0, Ar—H), 4.03 (m, 4H, dioxolane-H), 3.27 (m, 4H, pip-H), 2.01 (m, 4H, pip-H).

4-(3-Hydroxyimino-8-azabicyclo[3.2.1]oct-8-yl)naphthalene-1-carbonitrile (156AF17-240)

A solution of sodium acetate in water (1 mL) was added to a solution of 156AF03-217 (61 mg, 0.22 mmol) and hydroxylamine hydrochloride (31 mg, 0.44 mmol) in THF (2 mL). The reaction mixture was stirred in a sealed flask for 2×10 min under microwave irradiation at 120° C. The resulting yellow organic layer was separated and evaporated to dryness. The desired product was crystallized from a mixture of ethyl acetate and n-heptane (50:50).

$R_f$=0.25 (Ethyl acetate/n-Heptane 50:50). LCMS m/z 292 [M+H]$^+$. HPLC $t_R$=10.2 min (method III). $^1$H NMR (CDCl$_3$, 400 MHz) δ 8.26-8.19 (m, 2H, Ar—H), 7.76 (d, 1H, J=8.0, Ar—H), 7.67 (m, 1H, Ar—H), 7.59 (m, 1H, Ar—H), 6.93 (d, 1H, J=8.0, Ar—H), 4.32-4.23 (m, 2H, Tr—H), 3.32 (m, 1H, Tr—H), 2.94 (m, 1H, Tr—H), 2.62-2.49 (m, 2H, Tr—H), 2.13-2.03 (m, 2H, Tr—H), 1.86-1.69 (m, 2H, Tr—H).

3-Chloropropionic acid endo-8-(4-cyanonaphthalen-1-yl)-8-azabicyclo[3.2.1] oct-3-yl ester (156AF31-245)

A solution of 3-chloropropionyl chloride (370 µL, 3.84 mmol) in dry dichloromethane (2 mL) was added dropwise to a cold solution of 154BG31 (712 mg, 2.56 mmol) and triethylamine (714 µL, 5.12 mmol) in dry dichloromethane (8 mL) at −30° C. under argon atmosphere. The mixture was allowed to warm up to rt. After 4 hours stirring at rt the LCMS m/z 318 [M+H]$^+$. HPLC $t_R$=6.4 & 8.9 min (method I).

solvent was removed and the residue was partitioned between ethyl acetate and water. The organic layer was dried over sodium sulfate, filtered and evaporated to dryness (801 mg, 85%). The compound was used without further purification.

$R_f$=0.58 (Ethyl acetate/n-Heptane 50:50). LCMS m/z 369 [M+H]$^+$. HPLC $t_R$=13.6 min (method III).

Methoxyacetic acid endo-8-(4-cyanonaphthalen-1-yl)-8-azabicyclo[3.2.1]oct-3-yl ester (88PS39)

The compound was synthesized from methoxyacetyl chloride (50 μL, 0.54 mmol) and 154BG31 (100 mg, 0.36 mmol) using the same method as for preparation of 156AF31-245. The reaction time was extended to 20 hours. Purification by silica gel column chromatography, eluting with a stepwise gradient of 50-80% ethyl acetate in n-heptane, afforded the desired compound.

LCMS m/z 351 [M+H]$^+$. HPLC $t_R$=12.2 min (method III). $^1$H NMR (CDCl$_3$, 300 MHz) δ 8.19 (m, 2H, Ar—H), 7.76 (d, 1H, J=8.0, Ar—H), 7.66 (m, 1H, Ar—H), 7.57 (m, 1H, Ar—H), 6.91 (d, 1H, J=8.0, Ar—H), 5.39 (m, 1H, Tr—H), 4.18-4.07 (m, 4H, Tr—H, COCH$_2$O), 3.51 (s, 3H, OCH$_3$), 2.61-2.51 (m, 2H, Tr—H), 2.18-2.01 (m, 6H, Tr—H).

3-Morpholin-4-ylpropionic acid endo-8-(4-cyanonaphthalen-1-yl)-8-azabicyclo[3.2.1]oct-3-yl ester, hydrochloride (156AF32-246)

Sodium iodide (129 mg, 0.86 mmol) was added to a solution of 156AF31-245 (318 mg, 0.86 mmol) in dichloromethane. Morpholine (500 μL, 5.73 mmol) was added dropwise to the mixture at rt. Stirring was continued overnight at rt. The mixture was suspended on silica gel and purified by silica gel column chromatography eluting with 5% methanol in dichloromethane. The product (236 mg, 65%) was converted to the corresponding hydrochloride salt as described above.

$R_f$=0.26 (MeOH/CH$_2$Cl$_2$ 5:95). LCMS m/z 420 [M+H]$^+$. HPLC $t_R$=4.1 min (method II). $^1$H NMR (CDCl$_3$, 400 MHz) δ 8.16 (m, 2H, Ar—H), 7.73 (d, 1H, J=8.0, Ar—H), 7.63 (m, 1H, Ar—H), 7.54 (m, 1H, Ar—H), 6.88 (d, 1H, J=8.0, Ar—H), 5.27 (m, 1H, Tr—H), 4.11 (m, 2H, Tr—H), 3.70-3.60 (m, 7H, morpholine-H, COCH$_2$CH$_2$N), 3.46 (m, 1H, COCH$_2$CH$_2$N), 2.72 (m, 2H, Tr—H), 2.55-2.48 (m, 6H, Tr—H, morpholine-H), 2.18-1.98 (m, 6H, Tr—H).

3-(4-Ethylpiperazin-1-yl)propionic acid endo-8-(4-cyanonaphthalen-1-yl)-8-azabicyclo[3.2.1]oct-3-yl ester, hydrochloride (156AF35-247)

The desired compound was prepared from 156AF31-245 (480 mg, 1.30 mmol) and 1-ethylpiperazine (742 mg, 6.50 mmol) using the same method as for the preparation of 156AF32-246. The product (584 mg, 100%) was converted to the corresponding hydrochloride salt as described above.

$R_f$=0.36 (MeOH/CH$_2$Cl$_2$ 10:90). LCMS m/z 447 [M+H]$^+$. HPLC $t_R$=3.3 min (method II). $^1$H NMR (CDCl$_3$, 400 MHz) δ 8.16 (m, 2H, Ar—H), 7.73 (d, 1H, J=8.0, Ar—H), 7.63 (m, 1H, Ar—H), 7.54 (m, 1H, Ar—H), 6.88 (d, 1H, J=8.0, Ar—H), 5.27 (m, 1H, Tr—H), 4.11 (m, 2H, Tr—H), 2.74 (m, 2H, COCH$_2$CH$_2$N), 2.55-2.40 (m, 12H, CH$_{2Et}$, COCH$_2$CH$_2$N, piperazine-H), 2.18-1.98 (m, 6H, Tr—H), 1.10 (t, 3H, J=7.2, CH$_{3Et}$).

3-Diethylaminopropionic acid endo-8-(4-cyanonaphthalen-1-yl)-8-azabicyclo[3.2.1]oct-3-yl ester, hydrochloride (88PS37)

The desired compound was prepared from 156AF31-245 (272 mg, 0.74 mmol) and diethylamine (270 mg, 3.67 mmol) using the same method as for the preparation of 156AF32-246. The product (139 mg, 46%) was converted to the corresponding hydrochloride salt as described above.

LCMS m/z 406 [M+H]$^+$. HPLC $t_R$=3.2 min (method II). $^1$H NMR (CDCl$_3$, 300 MHz) δ 8.19 (m, 2H, Ar—H), 7.76 (d, 1H, J=8.0, Ar—H), 7.66 (m, 1H, Ar—H), 7.56 (m, 1H, Ar—H), 6.91 (d, 1H, J=8.0, Ar—H), 5.29 (m, 1H, Tr—H), 4.13 (m, 2H, Tr—H), 2.93 (m, 2H, COCH$_2$CH$_2$N), 2.68-2.48 (m, 6H, CH$_{2Et}$, Tr—H), 2.16-2.00 (m, 6H, Tr—H), 1.11 (t, 6H, J=7.2, CH$_{3Et}$).

Chloroacetic acid endo-8-(4-cyanonaphthalen-1-yl)-8-azabicyclo[3.2.1]oct-3-yl ester (156AF36-248)

The compound was synthesized form 154BG31 (235 mg, 0.84 mmol) and chloroacetyl chloride (100 μL, 1.26 mmol) using the same method as for the preparation of 156AF31-245. The reaction time was extended to 20 hours. Purification by silica gel column chromatography, eluting with a mixture of ethyl acetate and n-heptane (50:50), afforded the desired compound (189 mg, 64%).

$R_f$=0.59 (Ethyl acetate/n-Heptane 50:50). LCMS m/z 355 [M+H]$^+$. HPLC $t_R$=5.1 min (method II). $^1$H NMR (CDCl$_3$, 400 MHz) δ 8.17 (m, 2H, Ar—H), 7.74 (d, 1H, J=8.0, Ar—H), 7.64 (m, 1H, Ar—H), 7.55 (m, 1H, Ar—H), 6.90 (d, 1H, J=8.0, Ar—H), 5.35 (m, 1H, Tr—H), 4.13 (m, 4H, Tr—H, COCH$_2$Cl), 2.60-2.51 (m, 2H, Tr—H), 2.18 (m, 2H, Tr—H), 2.05 (m, 4H, Tr—H).

Morpholin-4-ylacetic acid endo-8-(4-cyanonaphthalen-1-yl)-8-azabicyclo[3.2.1]oct-3-yl ester, hydrochloride (156AF37-249)

The desired compound was synthesized from 156AF36-248 (175 mg, 0.49 mmol) and morpholine (430 μL, 4.93 mmol) using the same method as for the preparation of 156AF32-246. The product (175 mg, 88%) was converted to the corresponding hydrochloride salt as described above.

$R_f$=0.24 (MeOH/CH$_2$Cl$_2$ 4:96). LCMS m/z 406 [M+H]$^+$. HPLC $t_R$=4.2 min (method II). $^1$H NMR (CDCl$_3$, 400 MHz) δ 8.16 (m, 2H, Ar—H), 7.73 (d, 1H, J=8.0, Ar—H), 7.63 (m, 1H, Ar—H), 7.54 (m, 1H, Ar—H), 6.88 (d, 1H, J=8.0, Ar—H), 5.32 (m, 1H, Tr—H), 4.12 (m, 2H, Tr—H), 3.78 (m, 4H, morpholine-H), 3.25 (s, 2H, COCH$_2$N), 2.65 (m, 4H, morpholine-H), 2.55-2.49 (m, 2H, Tr—H), 2.15-1.99 (m, 6H, Tr—H).

Imidazol-1-ylacetic acid endo-8-(4-cyanonaphthalen-1-yl)-8-azabicyclo[3.2.1]oct-3-yl ester, hydrochloride (156AF40-251)

The desired compound was synthesized from 156AF36-248 (177 mg, 0.50 mmol) and imidazole (170 mg, 2.49 mmol) using the same method as for preparation of 156AF32-246. The reaction time was extended to 3 days. The product (153 mg, 81%) was converted to the corresponding hydrochloride salt as described above.

$R_f$=0.42 (MeOH/CH$_2$Cl$_2$ 10:90). LCMS m/z 387 [M+H]$^+$. HPLC $t_R$=3.6 min (method II). $^1$H NMR (CDCl$_3$, 400 MHz) δ 8.16 (d, 1H, J=8.0, Ar—H), 8.11 (d, 1H, J=8.0, Ar—H), 7.73 (d, 1H, J=8.0, Ar—H), 7.63 (m, 1H, Ar—H), 7.54 (m, 2H, Ar—H, imidazole-H), 7.12 (m, 1H, imidazole-H), 6.98 (m, 1H, imidazole-H), 6.85 (d, 1H, J=8.0, Ar—H), 5.35 (m, 1H, Tr—H), 4.06 (m, 2H, Tr—H), 3.48 (s, 2H, COCH$_2$N), 2.55-2.49 (m, 2H, Tr—H), 1.96 (m, 4H, Tr—H), 1.79 (m, 2H, Tr—H).

(4-Ethylpiperazin-1-yl)acetic acid endo-8-(4-cyanonaphthalen-1-yl)-8-azabicyclo[3.2.1]oct-3-yl ester, dihydrochloride (156AF42-252)

The desired compound was synthesized from 156AF36-248 (222 mg, 0.63 mmol) and ethyl piperazine (357 mg, 3.13 mmol) using the same method as for the preparation of 156AF32-246. The product (181 mg, 67%) was converted to the corresponding hydrochloride salt as described above.

R$_f$=0.15 (MeOH/CH$_2$Cl$_2$ 7:93). LCMS m/z 433 [M+H]$^+$. HPLC t$_R$=6.4 min (method II). $^1$H NMR (CDCl$_3$, 400 MHz) δ 8.16 (m, 2H, Ar—H), 7.73 (d, 1H, J=8.0, Ar—H), 7.63 (m, 1H, Ar—H), 7.54 (m, 1H, Ar—H), 6.88 (d, 1H, J=8.0, Ar—H), 5.30 (m, 1H, Tr—H), 4.11 (m, 2H, Tr—H), 3.22 (s, 2H, COCH$_2$N), 2.71-2.40 (m, 12H, piperazine-H, Tr—H, CH$_{2Et}$), 2.16-1.98 (m, 6H, Tr—H), 1.08 (t, 3H, J=7.2, CH$_{3Et}$).

Diethylaminoacetic acid endo-8-(4-cyanonaphthalen-1-yl)-8-azabicyclo[3.2.1]oct-3-yl ester, hydrochloride (156AF43-253)

The desired compound was synthesized from 156AF36-248 (151 mg, 0.43 mmol) and diethylamine (155 mg, 2.12 mmol) using the same method as for the preparation of 156AF32-246. The product (136 mg, 81%) was converted to the corresponding hydrochloride salt as described above.

R$_f$=0.47 (MeOH/CH$_2$Cl$_2$ 7:93). LCMS m/z 392 [M+H]$^+$. HPLC t$_R$=7.9 min (method II). $^1$H NMR (CDCl$_3$, 400 MHz) δ 8.16 (m, 2H, Ar—H), 7.73 (d, 1H, J=8.0, Ar—H), 7.63 (m, 1H, Ar—H), 7.54 (m, 1H, Ar—H), 6.88 (d, 1H, J=8.0, Ar—H), 5.30 (m, 1H, Tr—H), 4.11 (m, 2H, Tr—H), 3.33 (s, 2H, COCH$_2$N), 2.69 (q, 4H, J=7.2, CH$_{2Et}$), 2.54-2.48 (m, 2H, Tr—H), 2.15 (m, 2H, Tr—H), 2.02 (m, 4H, Tr—H), 1.08 (t, 6H, J=7.2, CH$_{3Et}$).

Succinic acid mono endo-[8-(4-cyanonaphthalen-1-yl)-8-azabicyclo[3.2.1]oct-3-yl]ester (156AF48-254)

Succinic anhydride (368 mg, 3.68 mmol) was added to a solution of 154BG31 (129 mg, 0.46 mmol) and triethylamine (160 μL, 1.15 mmol) in ethyl acetate (10 mL) at rt. The mixture was stirred at 50° C. for a week. Purification of the reaction mixture by silica gel column chromatography, eluting with a mixture of ethyl acetate and n-heptane (55:45) afforded the desired product (69 mg, 40%).

R$_f$=0.17 (Ethyl acetate). LCMS m/z 379 [M+H]$^+$. HPLC t$_R$=2.6 min (method II). $^1$H NMR (CDCl$_3$, 300 MHz) δ 8.10 (m, 2H, Ar—H), 7.68 (d, 1H, J=8.0, Ar—H), 7.57 (m, 1H, Ar—H), 7.48 (m, 1H, Ar—H), 6.83 (d, 1H, J=8.0, Ar—H), 5.20 (m, 1H, Tr—H), 4.05 (m, 2H, Tr—H), 2.70-2.56 (m, 4H, COCH$_2$CH$_2$COOH), 2.48-2.40 (m, 2H, Tr—H), 2.12-2.00 (m, 6H, Tr—H).

Trifluoroacetic acid endo-8-(4-cyanonaphthalen-1-yl)-8-azabicyclo[3.2.1]oct-3-yl ester (156AF54-259)

Trifluoroacetic anhydride (198 μL, 1.40 mmol) was added to a solution of 154BG31 (77 mg, 0.28 mmol) in ethyl acetate at rt. The mixture was stirred overnight at 60° C. The mixture was partitioned between ethyl acetate and water. The organic layer was dried over sodium sulfate, filtered and evaporated to dryness. Purification of the residue by silica gel column chromatography, eluting with a mixture of ethyl acetate and n-heptane (55:45) afforded the desired product (20 mg, 19%).

R$_f$=0.71 (Ethyl acetate/n-heptane 55:45). LCMS m/z 375 [M+H]$^+$. HPLC t$_R$=5.8 min (method II). $^1$H NMR (CDCl$_3$, 300 MHz) δ 8.17 (m, 2H, Ar—H), 7.79 (d, 1H, J=8.0, Ar—H), 7.71 (m, 1H, Ar—H), 7.59 (m, 1H, Ar—H), 6.93 (d, 1H, J=8.0, Ar—H), 5.49 (m, 1H, Tr—H), 4.18 (m, 2H, Tr—H), 2.68-2.60 (m, 2H, Tr—H), 2.27-2.03 (m, 6H, Tr—H).

4-(3,4-Dihydroxypyrrolidin-1-yl)naphthalene-1-carbonitrile (156AF59-258)

1-Boc-3,4-pyrrolidindiol (178 mg, 0.88 mmol) was stirred in a 2 M solution of hydrochloride acid in diethyl ether (3 mL). After 2 hours stirring at rt hydrochloride form of 3,4-pyrrolidindiol was isolated from the mixture by filtration. The product was dissolved in methanol and left on standing overnight with PS-trisamine resin (3.38 mmol/g, 0.5 g). The resin was removed by filtration and the solution was concentrated in vacuo affording 3,4-pyrrolidindiol as colourless oil. This material was dissolved in DMF (3 mL) and 1-cyano-4-fluoronaphthalene (66 mg, 0.39 mmol) was added to the solution. After 48 hour stirring at rt the reaction mixture was partitioned between ethyl acetate and water. The organic layer was washed with brine, dried over sodium sulfate, filtered and evaporated to dryness. Purification of the residue by silica gel column chromatography, eluting with a stepwise gradient of 5-10% methanol in dichloromethane, afforded the desired compound (14 mg, 14%).

R$_f$=0.38 (MeOH/CH$_2$Cl$_2$ 10:90). LCMS m/z 255 [M+H]$^+$. HPLC t$_R$=2.13 min (method III). $^1$H NMR (CDCl$_3$, 300 MHz) δ 8.21-8.12 (m, 2H, Ar—H), 7.69 (d, 1H, J=8.0, Ar—H), 7.60 (m, 1H, Ar—H), 7.49 (m, 1H, Ar—H), 6.68 (d, 1H, J=8.0, Ar—H), 4.50-4.41 (m, 2H, pyrrolidine-H), 3.94-3.80 (m, 2H, pyrrolidine-H), 3.72-3.51 (m, 2H, pyrrolidine-H), 2.88 (broad s, 2H, OH).

4-(3-exo-Ethynyl-3-endo-hydroxy-8-azabicyclo[3.2.1]oct-8-yl)naphthalene-1-carbonitrile (88PS41)

Ethynyl magnesium bromide reagent (0.5 M solution in anhydrous THF, 877 μL, 0.44 mmol) was added dropwise to a cold solution of 156AF03-217 (100 mg, 0.36 mmol) in anhydrous THF (2 mL) at 0° C. The mixture was allowed to warm up to rt. After 20 h stirring at rt the reaction was quenched with water. The mixture was partitioned between water and ethyl acetate. The organic layer was dried over sodium sulfate, filtered and evaporated to dryness. Purification of the residue by silica gel column chromatography, eluting with a stepwise gradient of 40-100% ethyl acetate in n-heptane, afforded the desired compound (6.4 mg, 6%).

LCMS m/z 303 [M+H]$^+$. HPLC t$_R$=11.5 min (method III). $^1$H NMR (CDCl$_3$, 300 MHz) δ 8.13-8.08 (m, 2H, Ar—H), 7.68 (d, 1H, J=8.0, Ar—H), 7.58 (m, 1H, Ar—H), 7.48 (m, 1H, Ar—H), 6.83 (d, 1H, J=8.0, Ar—H), 4.11-4.03 (m, 2H, Tr—H), 2.67-2.57 (m, 2H, Tr—H), 2.48 (s, 1H, CC—H), 2.26-2.13 (m, 4H, Tr—H), 1.92-1.78 (m, 3H, Tr—H, OH).

4-[3-(2-[1,3]Dioxan-2-ylethyl)-3-hydroxy-8-azabicyclo[3.2.1]oct-8-yl]naphthalene-1-carbonitrile (156AF53-260)

1,3-Dioxane-2-ylethyl magnesium bromide reagent (0.5 M solution in anhydrous THF: 860 μL, 0.43 mmol) was added dropwise to a solution of 156AF03-217 (80 mg, 0.29 mmol) in anhydrous THF (2 mL) at rt. After 48 h stirring at rt the reaction was quenched with saturated ammonium chloride. The mixture was partitioned between ammonium chloride and ethyl acetate. The organic layer was dried over sodium sulfate, filtered and evaporated to dryness. Purification of the residue by silica gel column chromatography, eluting with a stepwise gradient of 40-100% ethyl acetate in n-heptane, afforded the desired compound as a diastereomeric mixture, ratio 85:15 (37 mg, 45%).

LCMS m/z 393 [M+H]$^+$. HPLC $t_R$=4.3 & 4.8 min (method II). Major diastereomer: $^1$H NMR (CDCl$_3$, 300 MHz) δ 8.10-8.05 (m, 2H, Ar—H), 7.66 (d, 1H, J=8.0, Ar—H), 7.56 (m, 1H, Ar—H), 7.45 (m, 1H, Ar—H), 6.82 (d, 1H, J=8.0, Ar—H), 4.54 (m, 1H, dioxane-H), 4.11-4.02 (m, 4H, Tr—H, dioxane-H), 3.78-3.67 (m, 2H, dioxane-H), 2.29-1.56 (m, 13H, Tr—H, CH$_2$CH$_2$COH, dioxane-H), 1.34-1.24 (m, 1H, dioxane-H).

4-(endo-3-Methoxy-8-azabicyclo[3.2.1]oct-8-yl)naphthalene-1-carbonitrile (88PS44)

Sodium hydride (50% suspension in an mineral oil, 10 mg, 0.21 mmol) was added to solution of 154BG31 (50 mg, 0.18 mmol) at rt. After 15 minutes stirring at rt methyl iodide (22 μL, 0.36 mmol) was added to the mixture and stirring was continued overnight at 60° C. The mixture was allowed to cool down to rt and partitioned between ethyl acetate and water. The organic layer was dried over sodium sulfate, filtered and evaporated to dryness. Purification by silica gel column chromatography, eluting with a mixture of ethyl acetate and n-heptane (50:50), afforded the desired compound (4.4 mg, 8%).

LCMS m/z 293 [M+H]$^+$. HPLC $t_R$=5.6 min (method II).

(1S,4S)-5-(4-Cyanonaphthalen-1-yl)-2,5-diazabicyclo[2.2.1]heptane-2-carboxylic acid tert-butyl ester (165RL03)

1-Cyano-4-fluoronaphthalene (50 mg, 0.29 mmol) and t-butyl(1S,4S)-(−)-2,5-diazabicyclo-[2.2.1]heptane-2-carboxylate (86 mg, 0.44 mmol) was dissolved in pyridine (1 mL). DBU (18 μL, 0.12 mmol) was added and the mixture was shaken in a vial at 60° C. for 40 hours. After cooling to rt hydrochloric acid (1 M, 10 mL) was added and the mixture was extracted with dichloromethane (3×5 mL). The combined organic layers was washed with sodium hydrogen carbonate, dried over sodium sulfate and evaporated to dryness. The solid was purified by column chromatography on silica gel using ethyl acetate/n-heptane (1:1) giving a white solid (42 mg, 41%).

R$_f$=0.40 (EtOAc/n-heptane 1:1). LCMS m/z 350 [M+H]$^+$. HPLC $t_R$=12.4 min (method III). $^1$H-NMR (CDCl$_3$, 300 MHz) d 8.09 (d, 1H, J=7.9 Hz, Ar—H), 8.01 (d, 1H, J=7.9 Hz, Ar—H), 7.65 (d, 1H, J=7.9 Hz, Ar—H), 7.54 (m, 1H, Ar—H), 7.39 (m, 1H, Ar—H), 6.65 (d, 1H, J=7.9 Hz, Ar—H), 4.60-4.48 (m, 2H, pip-H), 3.92-3.39 (m, 4H, pip-H), 2.01-1.82 (m, 2H, pip-H), 1.36 (s, 9H, CH$_3$ $_{t\text{-}butyl}$).

4-((1S,4S)-2,5-Diazabicyclo[2.2.1]hept-2-yl)naphthalene-1-carbonitrile hydrochloride (165RL09)

165RL03 (207 mg, 0.59 mmol) was dissolved in dichloromethane (2 mL). Trifluoroacetic acid (2 mL) was added and the mixture was shaken in a vial at rt for 3 hours. TLC showed no more starting material. Hydrochloric acid (1 M, 5 mL) was added and the mixture was washed with ethyl acetate (2×10 mL). The aqueous layer was made alkaline with sodium hydroxide (2 M) and extracted with ethyl acetate (3×20 mL). The combined organic layers were dried over sodium sulfate and evaporated to dryness to give an off-white solid (146 mg, 99%). The product was converted to the corresponding hydrochloride salt as described above.

LCMS m/z 250 [M+H]$^+$. HPLC $t_R$=1.2 min (method II). $^1$H-NMR (CDCl$_3$, 300 MHz) d 8.13 (m, 2H, Ar—H), 7.72 (d, 1H, J=8.3, Ar—H), 7.60 (m, 1H, Ar—H), 7.45 (m, 1H, Ar—H), 6.70 (d, 1H, J=8.3, Ar—H), 4.48 (s, 1H, pip-H), 4.04 (dd, 1H, J=2.3, 9.4, pip-H), 3.86 (s, 1H, pip-H), 3.45-3.37 (m, 2H, pip-H), 3.17 (dd, 1H, J=2.1, 10.2, pip-H), 2.06-1.89 (m, 2H, pip-H), 2.01 (br, 1H, NH).

4-[(1S,4S)-5-(Methoxyacetyl)-2,5-diazabicyclo[2.2.1]hept-2-yl]naphthalene-1-carbonitrile (165RL10)

165RL09 (16.5 mg, 0.066 mmol) was dissolved in dichloromethane (1 mL). N,N-Diisopropylethylamine (DIPEA) (9.4 mg, 0.073 mmol) was added followed by methoxyacetyl chloride (7.9 mg, 0.073 mmol). The mixture was shaken in a vial at rt for 18 hours. Water (3 mL) was added and the layers were separated. The aqueous layer was extracted with ethyl acetate (2×5 mL) and the combined organic layers were evaporated. The compound was further purified by column chromatography on silica gel using ethyl acetate/methanol (1:1) to give the title compound (21 mg, 97%).

R$_f$=0.66 (EtOAc/MeOH 1:1). LCMS m/z 322 [M+H]$^+$. HPLC $t_R$=2.5 min (method II). $^1$H-NMR (CD$_3$OD, 300 MHz, rotamers 0.5:0.5) d 8.17 (d, 1H, J=8.4, Ar—H), 8.03 (dd, 1H, J=0.8 and 8.4, Ar—H), 7.76 (m, 1H, Ar—H), 7.63 (m, 1H, Ar—H), 7.51 (m, 1H, Ar—H), 6.90 (d, 1H, J=8.3, Ar—H), 4.96-4.66 (m, 2H, pip-H), 4.15 and 4.01 (2s, 2H, COCH$_2$O), 4.14-4.04 (m, 1H, pip-H), 3.91-3.80 (m, 1H, pip-H), 3.71-3.48 (m, 2H, pip-H), 3.38 and 3.36 (2s, 2H, OCH$_3$), 2.23-1.97 (m, 2H, pip-H) 4-((1S,4S)-5-Acetyl-2,5-diazabicyclo[2.2.1]hept-2-yl)naphthalene-1-carbonitrile (165RL11)

165RL09 (16.3 mg, 0.065 mmol) was dissolved in dichloromethane (1 mL). DIPEA (9.3 mg, 0.072 mmol) was added followed by acetyl chloride (5.6 mg, 0.072 mmol). This was shaken in a vial at rt for 18 hours. Water (3 mL) was added and the layers were separated. The aqueous layer was extracted with ethyl acetate (2×5 mL) the combined organic layers were evaporated. The compound was further purified by column chromatography on silica gel using ethyl acetate/methanol (9/1). Yield: 10.0 mg (53%)

R$_f$=0.23 (EtOAc/MeOH 9:1). LCMS m/z 292 [M+H]$^+$. HPLC $t_R$=2.5 min (method I). $^1$H-NMR (CDCl$_3$, 300 MHz, rotamers 0.5:0.5) d 8.17 (d, 1H, J=8.3, Ar—H), 8.06 (t, 1H, J=8.0, Ar—H), 7.73 (m, 1H, Ar—H), 7.63 (m, 1H, Ar—H), 7.48 (m, 1H, Ar—H), 6.75 (m, 1H, Ar—H), 5.04-4.53 (m, 2H, pip-H), 4.06-3.81 (m, 2H, pip-H), 3.65-3.53 (m, 2H, pip-H), 2.21-1.96 (m, 2H, pip-H), 2.12 and 1.98 (2s, 3H, CH$_3$).

4-[(1S,4S)-5-(2-Hydroxyethyl)-2,5-diazabicyclo[2.2.1]hept-2-yl]naphthalene-1-carbonitrile (165RL12)

165RL09 (16.2 mg, 0.065 mmol) was dissolved in THF (1 mL). Sodium carbonate (9.3 mg, 0.130 mmol) was added followed by 2-iodoethanol (5.6 mg, 0.072 mmol). The mixture shaken in a vial at 50° C. for 18 hours. Water (3 mL) was added and the layers were separated. The aqueous layer was extracted with ethyl acetate (2×5 mL) and the combined organic layers were evaporated. The compound was purified by column chromatography on silica gel using triethylamine/methanol (1:24) followed by preparative HPLC, giving 5.0 mg (26%) of pure compound.

$R_f$=0.30 (Et$_3$N/MeOH 1:24). LCMS m/z 292 [M+H]$^+$. HPLC $t_R$=1.5 min (method II). $^1$H-NMR (CD$_3$OD, 300 MHz) d 8.23 (d, 1H, J=8.5, Ar—H), 8.06 (dd, 1H, J=0.8 and 8.4, Ar—H), 7.78 (d, 1H, J=8.3 Hz, Ar—H), 7.65 (m, 1H, Ar—H), 7.52 (m, 1H, Ar—H), 6.88 (d, 1H, J=8.3, Ar—H), 4.52 (s, 1H, pip-H), 3.89-3.72 (m, 3H, pip-H), 3.67 (t, 2H, J=5.8, CH$_2$), 3.25-2.14 (m, 2H, pip-H), 2.84 (m, 2H, CH$_2$), 1.29 (m, 2H, pip-H).

4-((1S,4S)-5-Methyl-2,5-diazabicyclo[2.2.1]hept-2-yl)naphthalene-1-carbonitrile hydrochloride (165RL15)

165RL09 (26.4 mg, 0.106 mmol) was dissolved in methanol (5 mL) and formaldehyde (37% in water, 16 μL, 0.21 mmol) was added. The mixture was acidified by adding acetic acid (10 μL). After 5 min of shaking, sodium cyanoborohydride (46.6 mg, 0.741 mmol) was added and the mixture was allowed to react for 2 hours. The mixture was hydrolyzed by adding 5 drops of sodium hydroxide (2M) followed by water (10 mL) and the mixture extracted with dichloromethane (3×10 mL). The combined organic layers were dried over sodium sulfate, filtered and evaporated to dryness. The product (23 mg, 83%) needed no further purification and was converted to the corresponding hydrochloride salt as described above.

LCMS m/z 263 [M+H]$^+$. HPLC $t_R$=1.5 min (method I). $^1$H-NMR (CDCl$_3$, 300 MHz) d 8.13 (m, 2H, Ar—H), 7.70 (d, 1H, J=8.3, Ar—H), 7.59 (m, 1H, Ar—H), 7.44 (m, 1H, Ar—H), 6.66 (d, 1H, J=8.3, Ar—H), 4.36 (s, 1H, pip-H), 3.80-3.67 (m, 2H, pip-H), 3.51 (s, 1H, pip-H), 3.06-2.79 (m, 2H, pip-H), 2.41 (s, 3H, NCH$_3$), 2.05-1.92 (m, 2H, pip-H).

4-(3-Amino-8-azabicyclo[3.2.1]oct-8-yl)naphthalene-1-carbonitrile, hydrochloride (165RL21)

156AF03-217 (252 mg, 0.912 mmol) was dissolved in methanol (25 mL). Ammonium acetate (702 mg, 9.12 mmol) and sodium cyanoborohydride (57.3 mg, 0.912 mmol) were added together with some molecular sieves (3 Å). This mixture was allowed to react at rt for 60 hours. Hydrochloric acid (2 M) was added until pH<2 and the mixture was washed with ethyl acetate (2×25 mL). The aqueous layer was made alkaline with sodium hydroxide and extracted with ethyl acetate (3×30 mL). The combined organic layers were evaporated to dryness and purified by ion-exchange (SCX) to give 90 mg (36%) of the title compound.

LCMS m/z 278 [M+H]$^+$. HPLC $t_R$=2.1 min (method II). $^1$H-NMR (CD$_3$OD, 300 MHz, diastereomers endo:exo 3:2) d 8.17 (m, 2H, Ar—H), 7.71 (d, 1H, J=8.1, Ar—H), 7.61 (m, 1H, Ar—H), 7.52 (m, 1H, Ar—H), 6.86 (d, 1H, J=8.1, Ar—H), 4.10 (br, 2H, NH$_2$), 3.53 (m, 0.6H, endo-CH), 3.24 (m, 0.4H, exo-CH), 2.53-2.44 (m, 1H, Tr—H), 2.21 (m, 1H, Tr—H), 2.10-1.62 (m, 8H, Tr—H).

2-Chloro-N-[8-(4-cyanonaphthalen-1-yl)-8-azabicyclo[3.2.1]oct-3-yl]acetamide, hydrochloride (165RL23)

DMF (1.5 mL) was cooled to −30° C. and chloroacetyl chloride (20 μL, 0.251 mmol) was added. To this mixture a solution of 165RL21 (63 mg, 0.225 mmol) and DIPEA (44 μL, 0.249 mmol) in DMF (3.5 mL) was added over a period of 5 min. After stirring for 1 hour, the mixture was allowed to react at rt overnight. Water (15 mL) was then added and the mixture extracted with ethyl acetate (2×15 mL). The combined organic layers were evaporated and purified using column chromatography on silica gel eluting with n-heptane/ethyl acetate (1:4). The product (36 mg, 45%) was converted to the corresponding hydrochloride salt as described above.

$R_f$=0.42 (EtOAc/n-heptane 4:1). LCMS m/z 432 [M+H]$^+$. $^1$H-NMR (CDCl$_3$, 300 MHz, diastereomers endo:exo 3:2) d 8.18 (m, 2H, Ar—H), 7.73 (d, 1H, J=8.0, Ar—H), 7.64 (m, 1H, Ar—H), 7.55 (m, 1H, Ar—H), 7.17 (d, 0.6H, J=7.3, CONH), 6.87 (m, 1H, Ar—H), 6.53 (d, 0.4H, J=8.2, CONH), 4.39 (m, 1H, Tr—H), 4.17 (m, 1H, Tr—H), 4.09 (s, 1.2H, CH$_2$—Cl), 4.07 (s, 0.6H, CH$_2$—Cl), 2.66-2.58 (m, 1H, Tr—H), 2.17-1.18 (m, 7H, Tr—H).

N-[8-(4-Cyanonaphthalen-1-yl)-8-azabicyclo[3.2.1]oct-3-yl]-2-(4-ethylpiperazin-1-yl)acetamide, dihydrochloride (165RL27)

165RL23 (18 mg, 0.051 mmol), 1-ethylpiperazine (13 μL, 0.10 mmol) and potassium carbonate (14.1 mg, 0.10 mmol) were added to acetonitrile (2 mL). The mixture was shaken in a vial at 50° C. for 3 hours and then at rt for 3 days. The mixture was filtered, evaporated and purified by column chromatography on silica gel using methanol/ethyl acetate (9:1) as eluent. The pure product was evaporated and dissolved in dichloromethane (1 mL). The product was converted to the corresponding dihydrochloride salt (21 mg, 83%) as described above.

$R_f$=0.21 (EtOAc/MeOH 1:9). LCMS m/z 432 [M+H]$^+$. HPLC $t_R$=2.8 and 3.0 min (method II). $^1$H-NMR (CDCl$_3$, 300 MHz, diastereomers endo:exo 3:2) d 8.19 (m, 2H, Ar—H), 7.94 (d, 0.6H, J=8.2, CONH), 7.73 (m, 1H, Ar—H), 7.65 (m, 1H, Ar—H), 7.56 (m, 1H, Ar—H), 7.08 (d, 0.4H, J=8.7, CONH), 6.88 (m, 1H, AR), 4.39 (m, 1H, Tr—H), 4.17 (m, 2H, Tr—H), 3.03 (s, 1.2H, COCH$_2$), 3.02 (s, 0.8H, COCH$_2$), 2.68-2.39 (m, 11H), 2.19-1.82 (m, 7H), 1.08 (m, 3H, CH$_3$).

N-[8-(4-Cyanonaphthalen-1-yl)-8-azabicyclo[3.2.1]oct-3-yl]-2-diethylaminoacetamide, hydrochloride (165RL28)

Synthesized according to the same procedure as 165RL27.

$R_f$=0.28 (EtOAc/MeOH 9:1). LCMS m/z 391 [M+H]$^+$. HPLC $t_R$=4.2 and 4.6 min (method II). $^1$H-NMR (CDCl$_3$, 300 MHz, diastereomers endo:exo 3:2) d 8.19 (m, 2H, Ar—H), 8.13 (br, 0.6H, CONH), 7.74 (m, 1H, Ar—H), 7.65 (m, 1H, Ar—H), 7.56 (m, 1H, Ar—H), 7.40 (br, 0.4H, CONH), 6.88 (m, 1H, AR), 4.37 (m, 1H, Tr—H), 4.17 (m, 2H, Tr—H), 3.06 (s, 2H, COCH$_2$), 2.64-2.56 (m, 5H), 2.16-1.87 (m, 7H, Tr—H), 1.07 (m, 6H, CH$_3$).

2-Cyanoethyl endo-8-(4-cyanonaphthalen-1-yl)-8-azabicyclo[3.2.1]oct-3-yl N,N-diisopropylamidosphate (165RL22)

2-cyanoethyl tetraisopropylphosphoroamidite (98.5 mg, 0.327 mmol) was dissolved in dichloromethane (10 mL) and added under argon to 154BG31 (45.5 mg, 0.163 mmol), followed by the addition of 1H-tetrazole (3% in acetonitrile, 1.5 mL, 0.49 mmol). The mixture was stirred at rt for 75 min. After cooling to 0° C., m-chloroperbenzoic acid (110 mg, 0.490 mmol) was added and the stirring was continued for another 40 min at 0° C. The reaction mixture was washed with a 10% aqueous sodium thiosulfate solution (15 mL) followed by sat. sodium hydrogen carbonate solution (15 mL). The organic layer was dried over sodium sulfate and evaporated. The compound was further purified by column chromatography on silica gel using n-heptane/ethyl acetate (1:4) as eluent, followed by preparative HPLC purification, giving the title compound (11.3 mg).

$R_f$=0.21 (n-heptane/ethyl acetate 1:4). LCMS m/z 495 [M+H]$^+$. HPLC $t_R$=5.6 min (method II).

Endo-8-(4-cyanonaphthalen-1-yl)-8-azabicyclo [3.2.1]oct-3-yl hydrogen N,N-diisopropylamidophosphate (165RL29)

165RL22 (11.3 mg, 0.023 mmol) was dissolved in acetonitrile (2 mL) and 2 M sodium hydroxide (2 mL) was added. After 2 hours of stirring at rt TLC showed full conversion. The mixture was made acidic with 4 M hydrochloric acid and extracted with dichloromethane (3×5 mL). The combined organic layers were dried over sodium sulfate, filtered and evaporated to give 9.6 mg (95%) of pure product.

LCMS m/z 442 [M+H]$^+$. HPLC $t_R$=3.2 min (method II). $^1$H-NMR (CDCl$_3$, 300 MHz) d 9.33 (br, 1H, P—OH), 8.16 (m, 2H, Ar—H), 7.74 (d, 1H, J=8.1, Ar—H), 7.63 (m, 1H, Ar—H), 7.57 (m, 1H, Ar—H), 6.88 (d, 1H, J=8.1, Ar—H), 4.76 (m, 1H, Tr—H), 4.12 (m, 2H, Tr—H), 3.63-3.47 (m, 2H, N—CH—(CH$_3$)$_2$), 2.46 (m, 2H), 2.32-2.22 (m, 4H), 2.03-1.96 (m, 2H), 1.26 (d, 12H, J=6.8, CH—(CH$_3$)$_2$).

1-(3,4-Dinitronaphthalen-1-yl)pyrrolidine, hydrochloride (159JP06)

Pyrrolidine (2.0 mL) was added to 2,4-dinitro-1-naphthyl trifluoromethanesulfonate (219 mg, 0.57 mmol, Yang and Denny, J. Org. Chem., 2002, 67, 8958-8961) which resulted in an immediate, highly exothermic reaction. Volatiles were removed in vacuo and preparative TLC (dichloromethane, 10× eluted) afforded 2.8 mg (2.0%) of 159JP06 as a yellow solid. The product was converted to the corresponding hydrochloride salt as described above.

$R_f$=0.52 (CH$_2$Cl$_2$). LCMS m/z 288 [M+H]$^+$. $^1$H-NMR (CDCl$_3$, 400 MHz) δ 9.09 (s, 1H), 8.79 (m, 1H), 8.17 (m, 1H), 7.74 (m, 1H), 7.52 (m, 1H), 3.74 (m, 4H), 2.15 (m, 4H). HPLC $t_R$=11.3 min (method III).

1-(4,5,7-Trinitronaphthalen-1-yl)pyrrolidine, hydrochloride (159JP09)

Pyrrolidine (2.5 mL) was added to 1-chloro-4,5,7-trinitronaphthalene (100 mg, 0.33 mmol, Bassilios et al, Recueil., 1962, 81, 209-214) which resulted in an immediate, highly exothermic reaction. Volatiles were removed in vacuo and purification as in 159JP06 afforded 23 mg (22%) of 159JP09 as a red solid. The product was converted to the corresponding hydrochloride salt as described above.

$R_f$=0.60 (CH$_2$Cl$_2$). LCMS not ionizable. $^1$H-NMR (CDCl$_3$, 400 MHz) δ 9.09 (d, 1H, J=2.4), 8.81 (d, 1H, J=2.4), 8.32 (d, 1H, J=9.3), 7.21 (d, 1H, J=9.3), 3.85 (m, 4H), 2.19 (m, 4H). HPLC $t_R$=11.3 min (method III).

2-Bromo-4-pyrrolidin-1-ylnaphthalene-1-carbonitrile, hydrochloride (159JP07)

4-Pyrrolidin-1-ylnaphthalene-1-carbonitrile (136BG65-3, 320 mg, 1.44 mmol) was added to bromine (2 mL) and the resulting solution was stirred at rt overnight. Quenching the reaction with 4 M NaOH (50 mL), extraction with dichloromethane (3×50 mL), drying over Na$_2$SO$_4$, filtration and evaporation to dryness gave the crude product. Purification as in 159JP06 (dichloromethane as eluent) followed by recrystallisation (ethyl acetate/n-heptane) afforded 3.5 mg (0.8%) of 159JP07 as an off-white solid. The product was converted to the corresponding hydrochloride salt as described above.

$R_f$=0.64 (CH$_2$Cl$_2$). LCMS m/z 302 [M+H]$^+$. $^1$H-NMR (CDCl$_3$, 400 MHz) δ 8.23 (m, 1H), 8.12 (m, 1H), 7.59 (m, 1H), 7.43 (m, 1H), 6.85 (s, 1H), 3.62 (m, 4H), 2.05 (m, 4H). HPLC $t_R$=5.2 min (method II).

1-(2,4-Dibromonaphthalen-1-yl)pyrrolidine (159JP19)

2,4-Dibromo-1-naphthylamine (3.77 g, 12.5 mmol, Consden & Kenyon, J. Chem. Soc., 1935, 1591-1596), 1,4-dibromobutane (2.70 g, 12.5 mmol), N,N-diisopropylethylamine (3.88 g, 30 mmol) and toluene (15 mL) were heated at 120° C. for 3 days. The reaction was then cooled to rt, filtered, evaporated to dryness and purified by vacuum flash chromatography (dichloromethane/n-heptane 1:5) to provide 159JP 19 (2.50 g, 56%) as a yellowish thick oil which solidified on standing to give an off white solid.

$R_f$=0.83 (CH$_2$Cl$_2$). LCMS m/z 354 [M+H]$^+$. $^1$H-NMR (CDCl$_3$, 300 MHz) δ 8.22-8.03 (m, 2H), 7.85 (s, 1H), 7.62-7.40 (m, 2H), 3.55-3.20 (m, 4H), 2.25-1.96 (m, 4H). HPLC $t_R$=5.4 min (method II).

4-Pyrrolidin-1-ylnaphthalene-1,3-dicarbonitrile, hydrochloride (159JP26)

Adapting a protocol by Alterman and Hallberg (J. Org. Chem., 2000, 65, 7984-7989), 159JP19 (249 mg, 0.70 mmol), Zn(CN)$_2$ (42 mg, 0.35 mmol) and Pd(PPh$_3$)$_4$ (24 mg, 21 μmol), were weighed into a dried heavy-walled Pyrex tube under Ar atmosphere. DMF (3 mL) was added, the reaction vessel was sealed and the resulting mixture was exposed to microvawe irradiation (60 W) for 7 min. The reaction was cooled to rt, partitioned between ethyl acetate and water, the organic layer dried over Na$_2$SO$_4$, filtered and evaporated to dryness. Purification as in 159JP06 using dichloromethane/n-heptane (3:1) as eluent provided 15 mg (9%) of 159JP26 as an off-white solid. The product was converted to the corresponding hydrochloride salt as described above.

$R_f$=0.59 (CH$_2$Cl$_2$). LCMS m/z 248 [M+H]$^+$. $^1$H-NMR (CDCl$_3$, 300 MHz) δ 8.18-8.02 (m, 2H), 7.73 (s, 1H), 7.68-7.60 (m, 1H), 7.50-7.42 (m, 1H), 3.98-3.88 (m, 4H), 2.09-1.98 (m, 4H). HPLC $t_R$=4.4 min (method II).

1-(4,8-Dinitronaphthalen-1-yl)pyrrolidine, hydrochloride (159JP29)

Pyrrolidine (5.0 mL) was added to 1-chloro-4,8-dinitronaphthalene (50 mg, 0.20 mmol, Bassilios et al, Recueil, 1962, 81, 209-214) which resulted in an immediate, highly exothermic reaction. The reaction was further agitated for 5 min while heating using a heatgun. Volatiles were removed in vacuo and purification as in 159JP06 (dichloromethane/ n-heptane 4:1, 5× eluted) afforded 12 mg (21%) of 159JP29 as an orange solid. The product was converted to the corresponding hydrochloride salt as described above.

$R_f$=0.58 (CH$_2$Cl$_2$). LCMS m/z 288 [M+H]$^+$. $^1$H-NMR (CDCl$_3$, 300 MHz) δ 9.05 (dd, 1H, J=8.9, 1.0), 8.40 (d, 1H,

J=9.2), 7.95 (dd, 1H, J=7.5, 1.0), 7.59 (t, 1H, J=8.8), 6.78 (d, 1H, J=9.2), 3.30 (m, 4H), 1.95 (m, 4H). HPLC $t_R$=4.8 min (method II).

4-Pyrrolidin-1-ylnaphthalene-1-sulfonic acid (139MBT58-C)

1-Naphtylamine-4-sulfonic acid (200 mg, 0.90 mmol), 1,4-dibromobutane (193 mg, 0.90 mmol), N,N-diisopropylethylamine (383 μL, 2.24 mmol) and DMF (10 mL) were heated at 120° C. for 24 hours. The mixture was then cooled to rt and evaporated to dryness. The resulting oil was purified by preparative TLC, eluting with 8% methanol in dichloromethane, followed by cationic ion-exchange to provide 139MBT58-C (15 mg, 6%) as a green solid.

$R_f$=0.05 ($CH_2Cl_2$/methanol 9:1). LCMS m/z 277 $[M+H]^+$. HPLC $t_R$=1.2 min (method II). $^1$H-NMR (DMSO-$d_6$, 300 MHz) δ 8.96-8.88 (m, 1H), 8.24-8.15 (m, 1H), 7.98-7.89 (m, 1H), 7.67-7.52 (m, 2H), 7.42-7.30 (m, 1H), 3.76-3.45 (m, 4H), 2.18-2.00 (m, 4H).

[4-(Pyrrolidin-1-yl)naphthalen-1-yl]phosphonic acid diethyl ester (139MBT64-B)

A solution of 1-bromo-4-fluoronaphthalene (500 mg, 2.22 mmol) in tetrahydrofuran (5 mL) was added dropwise to stirred solution of t-BuLi (1.4 M in pentane, 3.17 mL, 4.44 mmol) in tetrahydrofuran (5 mL) at −78° C. The reaction mixture was stirred for 1 hour at −78° C., after which diethyl chlorophosphate (0.96 mL, 6.66 mmol) was added dropwise. The reaction mixture was left to warm to rt and concentrated. The residue was suspended in 2 M NaOH (50 mL) and extracted with dichloromethane (2×50 mL). The combined organic phases were dried over sodium sulfate, filtered and evaporated to give crude (4-fluoronaphthalen-1-yl)phosphonic acid diethyl ester (139MBT60-8C, 512 mg, 60% pure by NMR) as a yellow oil. 139MBT60-8C (200 mg, 0.425 mmol) was dissolved in pyrrolidine (0.5 mL) and stirred 2 hours at rt. The reaction mixture was concentrated and re-dissolved in dichloromethane (20 mL). The organic phase was washed with 2 M NaOH (20 mL) and dried over sodium sulfate, filtered and evaporated. The residue was purified by preparative TLC (0-5% methanol in dichloromethane) to give the title compound (89 mg, 30%) as a white solid.

LCMS m/z 334 $[M+H]^+$. $^1$H-NMR (CDCl$_3$) δ 8.47-8.42 (m, 1H), 8.28-8.24 (m, 1H), 8.17-8.07 (m, 1H), 8.08-7.52 (m, 1H), 7.47-7.40 (m, 1H), 6.86-6.80 (m, 1H), 4.26-4.12 (m, 2H), 4.12-3.97 (m, 2H), 3.60-3.53 (m, 4H), 2.08-2.02 (m, 4H), 1.35-1.27 (m, 6H).

[4-(Pyrrolidin-1-yl)naphthalen-1-yl]phosphonic acid monoethyl ester (139MBT64-2C)

(4-Pyrrolidin-1-ylnaphthalen-1-yl)phosphonic acid diethyl ester 139MBT64-B (40 mg, 0.11 mmol) was dissolved in pyrrolidine (0.5 mL) and the mixture was heated to 80° C. for 20 hours. The mixture was concentrated and the crude product was purified by preparative TLC (0-10% methanol in dichloromethane) to give the title compound (20 mg, 55%) as a white solid.

LCMS m/z 306 $[M+H]^+$. $^1$H-NMR (CDCl$_3$) δ 10.6-10.3 (bs, 1H), 8.35-8.29 (m, 1H), 8.05-8.00 (m, 1H), 7.95-7.82 (m, 1H), 7.53-7.40 (m, 2H), 7.19-7.12 (m, 1H), 4.01-3.82 (m, 6H), 2.34-2.22 (m, 4H), 1.25-1.15 (m, 3H).

1-(4-Methanesulfonylnaphthalen-1-yl)pyrrolidine (139MBT70-B)

A solution of 1-bromo-4-fluoronaphthalene (500 mg, 2.22 mmol) in tetrahydrofuran (1.5 mL) was added dropwise to stirred solution of t-BuLi (1.4 M in pentane, 3.17 mL, 4.44 mmol) in tetrahydrofuran (10 mL) at −78° C. The reaction mixture was stirred for 20 minutes at −78° C., after which the temperature was raised to −40° C., and sulfur dioxide was bubbled through the mixture for 5 minutes. The resulting clear solution was left to warm to rt and concentrated. Dry ether (20 mL) was added and the resulting white solid was collected by filtration to give the crude sulfinate salt (139MBT66-A, 280 mg) as a white solid. 139MBT66-A (100 mg) was suspended in DMF (3 mL), and potassium carbonate (192 mg, 1.39 mmol) was added followed by methyl iodide (0.09 mL, 1.39 mmol). The reaction mixture was stirred at rt for 20 hours, then concentrated and re-dissolved in dichloromethane (20 mL). The organic phase was washed with 2 M NaOH (20 mL) and dried over sodium sulfate, filtered and evaporated to give crude 1-fluoro-4-methanesulfonylnaphthalene (139MBT66-B, 89 mg, 86% yield). 139MBT66-B (89 mg, 0.397 mmol) was dissolved in pyrrolidine (0.5 mL) and stirred for 20 hours at rt. The reaction mixture was concentrated and the residue was re-dissolved in dichloromethane (20 mL). The organic phase was washed with 2 M NaOH (20 mL) and dried over sodium sulfate, filtered and evaporated. The residue was purified by preparative TLC (0-5% methanol in dichloromethane) to give the title compound (34 mg, 31% yield) as white solid.

LCMS m/z 276 $[M+H]^+$. $^1$H-NMR (CDCl$_3$) δ 8.69-8.63 (m, 1H), 8.34-8.28 (m, 1H), 8.18-8.13 (m, 1H), 7.68-7.60 (m, 1H), 7.51-7.44 (m, 1H), 6.80-6.74 (m, 1H), 3.66-3.59 (m, 4H), 3.18 (s, 3H), 2.10-2.03 (m, 4H).

[4-(Pyrrolidin-1-yl)naphthalen-1-yl]sulfonic acid amide (139MBT76-C)

The sulfinate salt 139MBT66-A (100 mg, 0.46 mmol) was dissolved in tetrahydrofuran (3 mL). Sulfuryl chloride (62 mg, 0.46 mmol) was added at 0° C. and the mixture was left to warm to rt. The mixture was again cooled to 0° C., and 25% aqueous ammonia (1 mL) was added. The mixture was left to warm to rt. Water (50 mL) was added, and the product was extracted with dichloromethane (2×50 mL). The combined organic phases were dried over sodium sulfate, filtered and evaporated to give crude [4-fluoronaphthalen-1-yl]sulfonic acid amide (139MBT68-B, 60 mg). 139MBT68-B (60 mg, 0.27 mmol) was dissolved in pyrrolidine (0.5 mL) and stirred for 20 hours at rt. The reaction mixture was concentrated and the residue was re-dissolved in dichloromethane (40 mL). The organic phase was washed with 2 M NaOH (40 mL) and dried over sodium sulfate, filtered and evaporated. The residue was purified by preparative TLC (0-5% methanol in dichloromethane) to give the title compound (8 mg, 6% yield from 139MBT66-A) as white solid.

LCMS m/z 277 $[M+H]^+$. $^1$H-NMR (CDCl$_3$) δ 8.58-8.53 (m, 1H), 8.31-8.26 (m, 1H), 8.16-8.11 (m, 1H), 7.65-7.58 (m, 1H), 7.50-7.42 (m, 1H), 6.75-6.70 (m, 1H), 3.61-3.54 (m, 4H), 2.07-2.01 (m, 4H).

[8-(4-Cyanonaphthalen-1-yl)-8-azabicyclo[3.2.1]oct-3-yl]urea (139MBT94-C)

The amine 165RL21 (40 mg, 0.144 mmol) was dissolved in tetrahydrofuran (1 mL) and cooled to 0° C. Trichloroacetyl isocyanate (0.019 mL) was added and the solution was left to warm to rt and stirring was continued for 30 minutes. The mixture was concentrated and the residue was dissolved in methanol (1 mL). 2 M NaOH (1 mL) was added, and the mixture was heated to 70° C. for 1 hour. Then, water (20 mL) was added and methanol was removed by evaporation in vacuo. The aqueous phase was extracted with dichloromethane (2×20 mL), and the combined organic phases were dried over sodium sulfate, filtered and evaporated. The residue was purified by preparative TLC (0-5% methanol in dichloromethane) to give the title compound (24 mg, 52% yield) as a white solid.

LCMS m/z 321 [M+H]$^+$. $^1$H-NMR (CDCl$_3$, exo/endo: 0.5:0.5) δ 8.20-8.15 (m, 2H), 7.76-7.72 (m, 1H), 7.67-7.61 (m, 1H), 7.58-7.51 (m, 1H), 6.90-6.84 (m, 1H), 4.86-4.82 (m, 0.5H), 4.37-4.11 (m, 5.5H), 2.66-2.58 (m, 1H), 2.20-1.80 (m, 8H).

Dimethylcarbamic acid endo-8-(4-cyanonaphthalen-1-yl)-8-azabicyclo[3.2.1]oct-3-yl ester (139MBT84-1E)

The alcohol 154BG31 (150 mg, 0.54 mmol) was dissolved in toluene (1 mL). Triethylamine (0.150 mL, 1.08 mmol) was added followed by dimethylcarbamoyl chloride (0.074 mL, 0.81 mmol). The reaction mixture was stirred at 90° C. for 3 days, and then concentrated. The crude product was purified by preparative TLC (0-5% methanol in dichloromethane) to give the title compound (32 mg, 17% yield) as a white solid.

LCMS m/z 350 [M+H]$^+$. $^1$H-NMR (CDCl$_3$) δ 8.21-8.15 (m, 2H), 7.77-7.73 (m, 1H), 7.68-7.61 (m, 1H), 7.59-7.52 (m, 1H), 6.92-6.88 (m, 1H), 5.20-5.515 (m, 1H), 4.16-4.10 (m, 2H), 2.97 (s, 6H), 2.57-2.46 (m, 2H), 2.20-2.00 (m, 6H).

4-(4-Hydroxy-4-phenylpiperidin-1-yl)naphthalene-1-carbonitrile (196MBT2-4)

1-Cyano-4-fluoronaphthalene (20 mg, 0.117 mmol) was dissolved in pyridine (1 mL). 4-Hydroxy-4-phenylpiperidine (83 mg, 0.467 mmol) was added and the reaction mixture was shaken at 110° C. for 3 days in a sealed vial. The reaction mixture was concentrated and re-suspended in 2 M HCl (1 mL). The product mixture was extracted with ethyl acetate (2×1 mL), and the combined organic phases were concentrated. The residue was purified by preparative reversed phase HPLC to give the title compound (14 mg, 36% yield) as a white solid.

LCMS m/z 329 [M+H]$^+$.

4-Azepan-1-ylnaphthalene-1-carbonitrile (196MBT2-6)

The title compound (7 mg, 24% yield) was prepared as described for 196MBT2-4 from 1-cyano-4-fluoronaphthalene (20 mg, 0.117 mmol) and hexamethyleneimine (46 mg, 0.468 mmol).

LCMS m/z 251 [M+H]$^+$.

4-(2,5-Dimethyl-2,5-dihydropyrrol-1-yl)naphthalene-1-carbonitrile (196MBT2-7)

The title compound (1 mg, 3% yield) was prepared as described for 196MBT2-4 from 1-cyano-4-fluoronaphthalene (20 mg, 0.117 mmol) and 2,5-dimethyl-2,5-dihydro-1H-pyrrole (45 mg, 0.468 mmol).

LCMS m/z 249 [M+H]$^+$.

4-(3,6-Dihydro-2H-pyridin-1-yl)naphthalene-1-carbonitrile (196MBT2-9)

The title compound (7 mg, 26% yield) was prepared as described for 196MBT2-4 from 1-cyano-4-fluoronaphthalene (20 mg, 0.117 mmol) and 1,2,3,6-tetrahydropyridine (39 mg, 0.468 mmol).

LCMS m/z 235 [M+H]$^+$.

4-(8-Oxo-1,5,6,8-tetrahydro-2H,4H-1,5-methanopyrido[1,2-a][1,5]diazocin-3-yl)naphthalene-1-carbonitrile (196MBT2-10)

The title compound (3 mg, 8% yield) was prepared as described for 196MBT2-4 from 1-cyano-4-fluoronaphthalene (20 mg, 0.117 mmol) and 8-oxo-1,5,6,8-tetrahydro-2H,4H-1,5-methanopyrido[1,2-a][1,5]diazocine (89 mg, 0.468 mmol).

LCMS m/z 342 [M+H]$^+$.

4-Thiomorpholin-4-ylnaphthalene-1-carbonitrile (196MBT2-11)

The title compound (6 mg, 20% yield) was prepared as described for 196MBT2-4 from 1-cyano-4-fluoronaphthalene (20 mg, 0.117 mmol) and thiomorpholine (48 mg, 0.468 mmol).

LCMS m/z 255 [M+H]$^+$.

4-(4-Benzyl-4-hydroxypiperidin-1-yl)naphthalene-1-carbonitrile (196MBT2-16)

The title compound (12 mg, 30% yield) was prepared as described for 196MBT2-4 from 1-cyano-4-fluoronaphthalene (20 mg, 0.117 mmol) and 4-benzyl-4-hydroxypiperidine (89 mg, 0.468 mmol).

LCMS m/z 343 [M+H]$^+$.

4-(4-Oxo-1-phenyl-1,3,8-triaza-spiro[4.5]dec-8-yl)naphthalene-1-carbonitrile (196MBT2-17)

The title compound (7 mg, 16% yield) was prepared as described for 196MBT2-4 from 1-cyano-4-fluoronaphthalene (20 mg, 0.117 mmol) and 1-phenyl-1,3,8-triazaspiro[4,5]decan-4-one (108 mg, 0.468 mmol).

LCMS m/z 383 [M+H]$^+$.

4-(4-Benzoylpiperidin-1-yl)naphthalene-1-carbonitrile (196MBT2-19)

The title compound (3 mg, 8% yield) was prepared as described for 196MBT2-4 from 1-cyano-4-fluoronaphthalene (20 mg, 0.117 mmol) and 4-benzoylpiperidine (89 mg, 0.468 mmol).

LCMS m/z 341 [M+H]$^+$.

1-(4-Cyanonaphthalen-1-yl)4-phenylpiperidine-4-carbonitrile (196MBT2-20)

The title compound (1 mg, 3% yield) was prepared as described for 196MBT2-4 from 1-cyano-4-fluoronaphthalene (20 mg, 0.117 mmol) and 4-cyano-4-phenylpiperidine (87 mg, 0.468 mmol).

LCMS m/z 338 [M+H]$^+$.

4-((S)-4a-Hydroxyoctahydroisoquinolin-2-yl)naphthalene-1-carbonitrile (196MBT2-24)

The title compound (8 mg, 22% yield) was prepared as described for 196MBT2-4 from 1-cyano-4-fluoronaphthalene (20 mg, 0.117 mmol) and (S)-4a-hydroxyoctahydroisoquinoline (73 mg, 0.468 mmol).
LCMS m/z 307 [M+H]$^+$.

4-(6-Methoxy-3,4-dihydro-1H-isoquinolin-2-yl)naphthalene-1-carbonitrile (196MBT2-26)

The title compound (7 mg, 19% yield) was prepared as described for 196MBT2-4 from 1-cyano-4-fluoronaphthalene (20 mg, 0.117 mmol) and 6-methoxy-3,4-dihydro-1H-isoquinoline (76 mg, 0.468 mmol).
LCMS m/z 315 [M+H]$^+$.

4-((R)-2-Phenylaminomethylpyrrolidin-1-yl)naphthalene-1-carbonitrile (196MBT2-2)

The title compound (7 mg, 18% yield) was prepared as described for 196MBT2-4 from 1-cyano-4-fluoronaphthalene (20 mg, 0.117 mmol) and (R)-(−)-2-phenylaminomethylpyrrolidine (82 mg, 0.468 mmol).
LCMS m/z 328 [M+H]$^+$.

4-(9-Hydroxy-1,5,7-trimethyl-3,7-diazabicyclo[3.3.1]non-3-yl)naphthalene-1-carbonitrile (196MBT2-13)

The title compound (3 mg, 8% yield) was prepared as described for 196MBT2-4 from 1-cyano-4-fluoronaphthalene (20 mg, 0.117 mmol) and 9-hydroxy-1,5,7-trimethyl-3,7-diazabicyclo[3.3.1]nonane (86 mg, 0.468 mmol).
LCMS m/z 336 [M+H]$^+$.

4-(3-Endo-hydroxy-3-exo-methyl-8-azabicyclo[3.2.1]oct-8-yl)naphthalene-1-carbonitrile (156AF70-267)

A solution of methyl magnesium bromide in diethyl ether (3 M, 3.7 mL, 11.09 mmol) was diluted with anhydrous THF (5 mL). Lithium bromide (1.93 g, 22.1 mmol) was slowly added to the solution at rt, followed by addition of a solution of Boc-nortropinone (500 mg, 2.21 mmol) in anhydrous THF (5 mL). The reaction mixture was stirred at 50° C. for 2 hours and stirring was continued overnight at rt. The reaction was quenched with water and the mixture partitioned between ethyl acetate and water. The organic layer was dried over sodium sulfate, filtered and evaporated to dryness. Purification of the residue by silica gel column chromatography, eluting with a mixture of ethyl acetate and n-heptane (50:50), afforded 3-hydroxy-3-methyl-8-azabicyclo[3.2.1]octane-8-carboxylic acid tert-butyl ester (168 mg, 31%). The obtained product was dissolved in 2 M HCl in diethyl ether (5 mL). After 4 hours stirring at rt the mixture was left on standing overnight. The formed participate, 3-methyl-8-azabicyclo[3.2.1]octan-3-ol hydrochloride, was isolated by filtration and dissolved in a mixture of dichloromethane and methanol (90:10). PS-Trisamine was added to the solution and it was left standing overnight. The resin was removed by filtration and washed with dichloromethane. The filtrate was evaporated to dryness affording pure 3-methyl-8-azabicyclo[3.2.1]octan-3-ol. 1-Cyano-4-fluoronaphthalene (37.1 mg, 0.22 mmol) was added to a solution of 3-methyl-8-azabicyclo[3.2.1]octan-3-ol (91 mg, 0.64 mmol) in DMF (1 mL), followed by addition of pyridine (1 mL). The reaction mixture was stirred overnight at 100° C., cooled down to rt and partitioned between ethyl acetate and water. The organic layer was dried over sodium sulfate, filtered and evaporated to dryness. Purification of the residue by silica gel column chromatography, eluting with a mixture of ethyl acetate and n-heptane (50:50), and by reverse phase preparative HPLC afforded the title compound (58 mg, 90%).

R$_f$=0.31 (Ethyl acetate/n-Heptane 50:50). $^1$H NMR (CDCl$_3$, 300 MHz) δ 8.26-8.15 (m, 2H, Ar—H), 7.78 (d, 1H, J=8.0, Ar—H), 7.71-7.51 (m, 2H, Ar—H), 6.91 (d, 1H, J=8.0, Ar—H), 4.21-4.10 (m, 2H, Tr—H), 2.39-2.28 (m, 4H, Tr—H), 2.02-1.89 (m, 4H, Tr—H), 1.39 (m, 3H, CH$_3$). LCMS m/z 293 [M+H]$^+$. HPLC t$_R$=4.1 (method A).

Alternatively, the title compound was obtained using the following procedure: To a solution of 197FBA20a (2.375 g, 13.42 mmol) in DMSO (35 mL) was added 1-cyano-4-fluonaphthalene (1.767 g, 10.32 mmol) and potassium carbonate (4.636 g, 33.54 mmol) and the reaction was allowed to stir at 100° C. for 18 h. The mixture was cooled, diluted with ethyl acetate (200 mL) and washed with water (3×35 mL). The organic phase was dried over sodium sulfate, filtered and evaporated to give a crude product which was purified by filtration over silica gel. Elution with a stepwise gradient of 30-50% ethyl acetate in heptane afforded the title compound as a white solid (2.539 g, 84%).

LCMS m/z 293 [M+H]$^+$. $^1$H-NMR (CDCl$_3$, 300 MHz) δ 8.19 (d, J=8.5, 2H), 7.76 (d, J=8.1, 1H), 7.70-7.60 (m, 1H), 7.60-7.50 (m, 1H), 6.92 (d, J=8.1, 1H), 4.27-4.08 (m, 2H), 2.43-2.26 (m, 4H), 2.06-1.86 (m, 4H), 1.37 (s, 3H). $^{13}$C-NMR (CDCl$_3$, 75 MHz) 153.0, 134.6, 133.8, 128.5, 128.0, 126.2, 126.1, 125.6, 119.3, 111.2, 102.2, 69.9, 60.6, 46.2, 34.7, 26.9.

Alternatively, the title compound was obtained using the following procedure: To a suspension of lithium chloride (26 mg, 0.621 mmol) and sodium borohydride (23 mg, 0.621 mmol) in diglyme (0.5 mL) was added a solution of 183AF16-294 (120 mg, 0.414 mmol) in diglyme (0.5 mL), and the reaction mixture was stirred at 90° C. After 13 h the mixture was diluted with diethylether and washed with water. The organic phase was dried over sodium sulfate, filtered and evaporated. The crude product (98 mg, 76%) was purified by recrystallization from ethyl acetate or by filtration over silica gel as described above to give pure title compound.

4-(3-endo-Hydroxy-3-exo-propyl-8-azabicyclo[3.2.1]oct-8-yl)naphthalene-1-carbonitrile (156AF96-284)

The title compound was prepared from 3-propyl-8-azabicyclo[3.2.1]octan-3-ol and 1-cyano-4-fluoronaphthalene using the same method as for preparation of 156AF70-267. R$_f$=0.43 (ethyl acetate/n-heptane 50:50). $^1$H NMR (CDCl$_3$, 300 MHz) δ 8.20 (m, 2H, Ar—H), 7.77 (d, 1H, J=8.0, Ar—H), 7.70-7.51 (m, 2H, Ar—H), 6.91 (d, 1H, J=8.0, Ar—H), 4.21-4.10 (m, 2H, Tr—H), 2.39-2.22 (m, 4H, Tr—H), 2.01-1.84 (m, 4H, Tr—H), 1.63-1.40 (m, 4H, CH$_2$pr), 1.00 (m, 3H, CH$_3$pr). LCMS m/z 321 [M+H]$^+$. HPLC t$_R$=5.1 min (method A).

4-(endo-Spiro[8-azabicyclo[3.2.1]octane-3,2'-oxiran]-8-yl)naphthalene-1-carbonitrile (183AF16-294)

Trimethylsulfoxonium iodide (359 mg, 1.63 mmol) was added to a suspension of sodium hydride (55%, 71 mg, 1.63 mmol) in dry DMSO (1.5 mL) at rt under argon atmosphere. After 1 hour stirring at rt, a solution of 4-(3-oxo-8-azabicyclo[3.2.1]oct-8-yl)naphthalene-1-carbonitrile (156AF03-217) in DMSO (2.0 mL) was added to the reaction mixture at rt. Stirring was continued overnight at rt. The reaction mixture was partitioned between ethyl acetate and water. The organic layer was washed with 4% (w/v) aqueous magnesium sulfate, dried over sodium sulfate, filtered and evaporated to dryness. Purification of the residue by silica gel column chromatography, eluting with a stepwise gradient of 30 to 45% of ethyl acetate in n-heptane, afforded the title compound (194 mg, 61%).

$R_f$=0.26 (Ethyl acetate/n-Heptane 45:55). LCMS m/z 291 [M+H]$^+$. $^1$H-NMR (CDCl$_3$, 300 MHz) δ 8.24 (d, J=8.4, 1H), 8.20 (d, J=8.3, 1H), 7.77 (d, J=8.0, 1H), 7.71-7.62 (m, 1H), 7.61-7.52 (m, 1H), 6.94 (d, J=8.0, 1H), 4.33-4.16 (m, 2H) 2.85-2.71 (m, 2H), 2.58 (s, 2H), 2.36-2.17 (m, 2H), 2.15-1.97 (m, 2H), 1.55-1.41 (m, 2H). $^{13}$C-NMR (CDCl$_3$, 75 MHz) 152.9, 134.6, 133.8, 128.6, 128.1, 126.5, 126.1, 125.5, 119.2, 111.6, 102.7, 61.0, 55.1, 48.7, 40.9, 27.3.

4-[3-exo-(4-ethylpiperazin-1-ylmethyl)-3-endo-hydroxy-8-azabicyclo[3.2.1]oct-8-yl]naphthalene-1-carbonitrile (183AF18-295)

N-Ethyl piperazine (2.0 mL, 15.8 mmol) was added to a solution of 183AF16-294 (74 mg, 0.25 mmol) in methanol (0.5 mL) at rt. The reaction mixture was shaken overnight at 70° C., allowed to cool down to rt and partitioned between ethyl acetate and water. The organic layer was washed with brine, dried over sodium sulfate, filtered and evaporated to dryness. Purification of the residue by silica gel column chromatography, eluting with 10% methanol in dichloromethane, afforded the title compound (85 mg, 84%).

$R_f$=0.22 (MeOH/CH$_2$Cl$_2$ 15:85). LCMS m/z 405 [M+H]$^+$. HPLC $t_R$=2.6 min (method A). $^1$H NMR (CDCl$_3$, 300 MHz) δ 8.22-8.11 (m, 2H), 7.76 (d, 1H, J=8.0), 7.69-7.50 (m, 2H), 6.90 (d, 1H, J=8.0), 4.21-4.10 (m, 2H), 2.84-2.30 (m, 14H), 2.19-2.09 (m, 2H), 2.01-1.84 (m, 4H), 1.18-1.08 (m, 3H).

4-(3-endo-hydroxy-3-exo-hydroxymethyl-8-azabicyclo[3.2.1]oct-8-yl)naphthalene-1-carbonitrile (183AF19-296)

Aqueous sulfuric acid (0.2 M, 2.5 mL) was added dropwise to a solution of 183AF16-294 (60 mg, 0.21 mmol) in THF (2.5 mL) at rt. After 3 hours stirring at rt the reaction mixture was neutralized with saturated sodium bicarbonate. THF was removed and the residue passed over an acidic ion-exchange SPE cartridge. The obtained product was purified by silica gel column chromatography using ethyl acetate as eluent. Yield: 20 mg, 31%.

$R_f$=0.13 (MeOH/CH$_2$Cl$_2$ 05:95). LCMS m/z 309 [M+H]$^+$. HPLC $t_R$=2.5 min (method A). $^1$H NMR (CDCl$_3$, 300 MHz) δ 8.31 (d, 1H, J=8.0, Ar—H), 8.21 (d, 1H, J=8.0, Ar—H), 7.79 (d, 1H, J=8.0, Ar—H), 7.73-7.60 (m, 2H, Ar—H), 6.94 (d, 1H J=8.0, Ar—H), 4.31-4.20 (m, 2H, Tr—H), 3.61 (s, 2H, CH$_2$OH), 2.59-2.48 (m, 2H, Tr—H), 2.20-1.69 (m, 6H, Tr—H).

4-(3-exo-Cyanomethyl-3-endo-hydroxy-8-azabicyclo[3.2.1]oct-8-yl)naphthalene-1-carbonitrile (183AF21-297)

Potassium cyanide (45 mg, 0.69 mmol) and lithium perchlorate (12 mg, 0.11 mmol) were added to a solution of 183AF16-294 (29 mg, 0.10 mmol) in acetonitrile (2 mL) at rt. The reaction mixture was stirred at 70° C. for 3 days. The reaction mixture was allowed to cool to rt and partitioned between ethyl acetate and water. The organic layer was dried over sodium sulfate, filtered and evaporated to dryness. Purification of the residue by silica gel column chromatography, eluting with a mixture of ethyl acetate and n-heptane (45:55), afforded the title compound (13 mg, 41%).

$R_f$=0.11 (ethyl acetate/n-heptane 45:55). LCMS m/z 318 [M+H]$^+$. HPLC $t_R$=3.6 min (method A). $^1$H NMR (CDCl$_3$, 300 MHz) δ 8.21 (d, 1H, J=8.0, Ar—H), 8.14 (d, 1H, J=8.0, Ar—H), 7.78 (d, 1H, J=8.0, Ar—H), 7.70-7.55 (m, 2H, Ar—H), 6.92 (d, 1H, J=8.0, Ar—H), 4.28-4.16 (m, 2H, Tr—H), 2.62 (s, 2H, CH$_2$CN), 2.48-2.01 (m, 8H, Tr—H).

4-(3-endo-Hydroxy-3-exo-{[2-(1H-imidazol-4yl)ethylamino]methyl}-8-azabicyclo[3.2.1]oct-8-yl)naphthalene-1-carbonitrile (183AF23-298)

A solution of histamine (192 mg, 1.72 mmol) in methanol (1 mL) was added to a solution of 183AF16-294 (50 mg, 0.17 mmol) in THF (1 mL). After 20 hours stirring at 60° C., the reaction mixture was allowed to cool to rt and partitioned between ethyl acetate and water. The organic layer was dried over sodium sulfate, filtered and evaporated to dryness. Purification of the residue by silica gel column chromatography, eluting with a stepwise gradient of 15-50% methanol in dichloromethane, afforded the title compound (32 mg, 47%).

$R_f$=0.11 (MeOH/CH$_2$Cl$_2$ 50:50). LCMS m/z 402 [M+H]$^+$. HPLC $t_R$=1.9 min (method A).

4-(3-endo-Hydroxy-3-exo-methoxymethyl-8-azabicyclo[3.2.1]oct-8-yl)naphthalene-1-carbonitrile (183AF24-299)

A solution of concentrated sulfuric acid (14 μL) in methanol (1 mL) was added dropwise to solution of 183AF16-294 (53 mg, 0.18 mmol) in THF (1 mL) at rt. After 1 hour stirring at rt, the reaction mixture was neutralized with saturated sodium bicarbonate and concentrated in vacuo. The residue was partitioned between ethyl acetate and water. The organic layer was washed with brine, dried over sodium sulfate, filtered and evaporated to dryness. Purification of the residue by silica gel column chromatography, eluting with a stepwise gradient of 45-80% ethyl acetate in n-heptane, afforded the title compound (17 mg, 29%).

$R_f$=0.28 (ethyl acetate/n-heptane 80:20). LCMS m/z 323 [M+H]$^+$. HPLC $t_R$=3.2 min (method A). $^1$H NMR (CDCl$_3$, 300 MHz) δ 8.18 (d, 1H, J=8.0, Ar—H), 8.12 (d, 1H, J=8.0, Ar—H), 7.67 (d, 1H, J=8.0, Ar—H), 7.61-7.53 (m, 2H, Ar—H), 6.81 (d, 1H, J=8.0, Ar—H), 4.21-4.10 (m, 2H, Tr—H), 3.62 (s, 2H, CH$_2$OCH$_3$), 3.20 (s, 3H, CH$_2$OCH$_3$), 2.36-2.23 (m, 2H, Tr—H), 2.03-1.96 (m, 4H, Tr—H), 1.71-1.63 (m, 2Tr—H).

7-Bromo-4-pyrrolidin-1-ylnaphthalene-1-carbonitrile, hydrochloride and 6-bromo-4-pyrrolidin-1-ylnaphthalene-1-carbonitrile, hydrochloride (159JP02-X3)

1-Cyano-4-fluoronaphthalene (360 mg, 2.1 mmol) and bromine (1.5 mL) were heated to 60° C. for 1 h in a sealed vial. After cooling to rt, the reaction mixture was quenched with 4 M NaOH (50 mL), extracted with dichloromethane (3×50 mL), dried over sodium sulfate, filtered and concentrated in vacuo. The residue was passed through a pad of silica (n-heptane/dichloromethane 1:1), and the collected fractions concentrated in vacuo. Pyrrolidine (1.5 mL) was added to the off-white residue thus obtained (90 mg) and the resulting mixture was heated under microwave irradiation at 100° C. for 10 min and the reaction mixture concentrated in vacuo. Purification by preparative TLC (n-heptane/dichloromethane, 1:1, 5× eluted) afforded the title compounds (8.0 mg, 1.1%) as an off-white solid. The product was converted to the corresponding hydrochloride salt as described above.

$R_f$=0.71 (CH$_2$Cl$_2$). LCMS m/z 302 [M+H]$^+$. $^1$H-NMR (CDCl$_3$, 300 MHz, 3:1 mixture of two regioisomers) δ 8.42 (d, 0.75H, J=3.2), 8.29 (d, 0.25H, J=3.2), 8.10 (d, 0.25H, J=10.0), 8.01 (d, 0.75H, J=10.0), 7.72 (d, 0.75H, J=10.0), 7.69 (d, 0.25H, J=10.0), 7.65 (dd, 0.75H, J=10.5, 2.0), 7.48 (dd, 0.25H, J=10.5, 2.0), 672 (d, 0.75H, J=8.8), 6.67 (d, 0.25H, J=8.8), 3.61 (m, 4H), 2.04 (m, 4H). HPLC $t_R$=5.5 min (method III).

4-(8-Azaspiro[4.5]dec-8-yl)naphthalene-1-carbonitrile (159JP61AA).

4-Amino-1-naphthalenecarbonitrile (168.20 mg), 3,3-tetramethylene-1,5-dibromopentane (284 mg, 1.0 mmol, Klitgaard, N. et al., Acta Chem. Scand. 1970, 24, 33-42), N,N-diisopropylethylamine (323 mg, 2.5 mmol) and toluene (15 mL) were heated to 120° C. for 16 h. The crude product was poured in water (100 mL), extracted with ethyl acetate (3×100 mL), the combined organic layers dried over sodium sulfate, filtered and concentrated in vacuo. Purification by preparative TLC (dichloromethane, 3× eluted) afforded the title compound (14 mg, 5.0%) as an off-white solid.

$R_f$=0.57 (CH$_2$Cl$_2$). LCMS m/z 291 [M+H]$^+$. $^1$H-NMR (CDCl$_3$, 300 MHz) δ 8.11 (d, 2H, J=11.0), 7.72 (d, 1H, J=11.0), 7.61-7.43 (m, 2H), 6.92 (d, 1H J=11.0), 3.05 (m, 4H), 1.75-1.22 (m, 12H). HPLC $t_R$=7.0 min (method III).

4-Nitrobenzoic acid exo-8-(4-cyanonaphthalen-1-yl)-8-azabicyclo[3.2.1]oct-3-yl ester (159JP66C)

Diisopropylazodicarboxylate (1.62 g, 8.0 mmol) was added over 10 min to a solution of 154BG31 (556.7 mg, 2.0 mmol), triphenylphosphine (2.098 g, 8.0 mmol) and 4-nitrobenzoic acid (1.34 g, 8.0 mmol) in THF (15 mL) under argon atmosphere at 0° C. The reaction was stirred overnight at rt, then additional 3 h at 40° C. before partitioning the mixture between diethylether (150 mL) and sat. aq. NaHCO$_3$ (150 mL). The aqueous phase was extracted with additional diethylether (100 mL), n-heptane (300 mL) was added to the combined ether extracts and the resulting solution was passed through a pad of silica. The title compound crystallized upon standing as long yellow needles which were collected by filtration and then dried in vacuo to afford the desired product (425 mg, 50%).

$R_f$=0.42 (CH$_2$Cl$_2$). LCMS m/z 428 [M+H]$^+$. $^1$H-NMR (CDCl$_3$, 300 MHz) δ 8.35-8.25 (m, 6H), 7.78 (d, 1H, J=7.5), 7.70-7.55 (m, 2H), 6.82 (d, 1H J=7.5), 5.53 (m, 1H), 4.12 (br s, 2H), 2.41-1.88 (m, 8H). HPLC $t_R$=6.0 min (method III).

4-(3-exo-Hydroxy-8-azabicyclo[3.2.1]oct-8-yl)naphthalene-1-carbonitrile (159JP68F6)

159JP66C (280 mg, 0.65 mmol), 2 M LiOH (30 mL) and tetrahydrofuran (30 mL) were stirred overnight at rt, extracted with dichloromethane (3×100 mL), dried over Na$_2$SO$_4$, filtered and concentrated in vacuo. The residue was purified by vacuum flash chromatography, eluting with a gradient of 0-50% ethyl acetate in n-heptane, to give the title compound (162 mg, 89%) as an off-white solid.

$R_f$=0.21 (ethyl acetate/n-heptane 1:1). LCMS m/z 279 [M+H]$^+$. $^1$H-NMR (CDCl$_3$, 300 MHz) δ 8.28-8.16 (m, 2H), 7.77 (d, 1H, J=8.1), 7.71-7.53 (m, 2H), 6.82 (d, 1H, J=8.1), 4.21 (m, 3H), 2.22-1.79 (m, 6H), 1.38-0.89 (m, 2H). HPLC $t_R$=3.2 min (method III).

4-(3-exo-Methoxy-8-azabicyclo[3.2.1]oct-8-yl)naphthalene-1-carbonitrile (159JP72A)

159JP68F6 (34 mg, 0.12 mmol), sodium hydride (50%, 9 mg, 0.18 mmol) and iodomethane (35 mg, 0.24 mmol) were shaken in tetrahydrofuran (5 mL) under argon atmosphere at 50° C. for 24 h. The crude product was quenched by methanol (10 mL), concentrated in vacuo. Purification by preparative TLC (ethyl acetate/n-heptane 1:4, 3× eluted) afforded the title compound (26 mg, 73%) as an off-white solid.

$R_f$=0.34 (ethyl acetate/n-heptane 1:1). LCMS m/z 293 [M+H]$^+$. $^1$H-NMR (CDCl$_3$, 300 MHz) δ 8.28-8.09 (m, 2H), 7.66 (d, 1H, J=8.8), 7.61-7.42 (m, 2H), 6.82 (d, 1H, J=8.8), 4.12 (m, 2H), 3.63 (m, 1H), 3.32 (s, 3H), 2.17-1.64 (m, 8H). HPLC $t_R$=4.6 min (method III).

(S)-1-(4-Cyanonaphthalen-1-yl)pyrrolidine-2-carboxylic acid methyl ester (159JP74A)

1-Cyano-4-fluoronaphthalene (109 mg, 0.64 mmol) and L-proline methyl ester (380 mg, 2.95 mmol) were heated to 60° C. for 2 days in a sealed vial. The crude product was concentrated in vacuo and purified by preparative TLC (ethyl acetate/n-heptane 1:3, 3× eluted) to afford the title compound (2.9 mg, 1.7%) as an off-white solid.

$R_f$=0.42 (ethyl acetate/n-heptane 1:1). LCMS m/z 281 [M+H]$^+$. $^1$H-NMR (CDCl$_3$, 300 MHz) δ 8.18-8.08 (m, 2H), 7.68 (d, 1H, J=8.2), 7.60-7.41 (m, 2H), 6.78 (d, 1H, J=8.2), 4.58 (t, 1H, J=5.8), 4.05 (m, 1H), 3.55 (s, 3H), 3.22 (m, 1H), 2.42-1.88 (m, 4H). HPLC $t_R$=4.0 min (method III).

4-(8-Azabicyclo[3.2.1]oct-2-en-8-yl)naphthalene-1-carbonitrile (159JP80XX)

Oxalyl chloride (6.84 mL, 79.4 mmol) in dichloromethane (300 mL) was added under argon to dimethylsulfoxide (11.28 mL) in dichloromethane (100 mL) at −60° C. To the resulting solution, 154BG31 (10.02 g, 36 mmol) in dichloromethane (100 mL) was added at a rate so that temperature did not exceed −60° C. The reaction was then kept at −50° C. for 1 h before cooling to −60° C., adding triethylamine (29.53 mL, 216.3 mmol) slowly and allowing the reaction to warm to rt overnight. The volatiles were removed in vacuo, the residue extracted with ethyl acetate (3×300 mL), the combined ethyl acetate layers washed with water (500 mL), and the organic phases were dried over sodium sulfate, filtered and concentrated in vacuo. Crystallization from ethyl acetate gave an off-white solid which was filtered off, the mother liquor was concentrated in vacuo and preparative TLC (ethyl acetate/n-heptane, 1:4, 5× eluted) afforded the title compound (3.6 mg, 0.04%) as an off-white solid.

$R_f$=0.57 (dichloromethane). LCMS m/z 261 [M+H]$^+$. $^1$H-NMR (CDCl$_3$, 300 MHz) δ 8.15 (d, 1H, J=7.0), 7.70-7.42 (m, 4H), 6.92 (d, 1H, J=7.0), 6.05 (m, 1H), 5.52 (m, 1H), 4.43 (m, 1H), 4.02 (m, 1H), 2.40-1.90 (m, 6H). HPLC $t_R$=5.4 min (method III).

4(8-Azabicyclo[3.2.1]oct-8-yl)naphthalene-1-carbonitrile (173FBA64b)

To a solution of 173FBA60a (400 mg, 0.9 mmol) in DMF/sulfolane 1:1 (5 mL) and cyclohexane (5 mL) was added sodium cyanoborohydride (226 mg, 3.6 mmol) and p-toluenesulfonic acid monohydrate (45 mg), and the reaction was stirred at 110° C. for 7 h. The reaction was then diluted with water and extracted three times with cyclohexane. The cyclohexane solution was washed twice with water, dried over sodium sulfate, filtered and evaporated to give a crude product, which was purified by silica gel column chromatography using heptane/ethyl acetate (8:2) as the eluent, to give 173FBA64b as a white solid (94 mg, 40%).

LCMS m/z 263 [M+H]$^+$. $^1$H-NMR (CDCl$_3$, 300 MHz) δ 8.28 (d, J=8.3, 1H), 8.18 (d, J=8.9, 1H), 7.75 (d, J=8.1, 1H), 7.71-7.61 (m, 1H), 7.61-7.51 (m, 1H), 6.90 (d, J=8.1, 1H), 4.28-4.02 (m, 2H), 2.28-1.92 (m, 4H), 1.92-1.58 (m, 6H). $^{13}$C-NMR (CDCl$_3$, 75 MHz) 153.6, 134.7, 133.9, 128.5, 128.0, 126.1, 126.0, 125.9, 119.4, 111.0, 101.9, 61.6, 32.6, 27.5, 17.5.

Alternatively, the title compound was also obtained using the following procedure: 8-Azabicyclo[3,2,1]octane (20 mg, 0.18 mmol), 1-cyano-4-fluoronaphthalene (46 mg, 0.27 mmol) and pyridine (0.5 mL) were heated overnight at 100° C., concentrated in vacuo and the residue purified by preparative TLC (dichloromethane, 3× eluted) to afford the title compound (1.8 mg, 4.0%) as a yellow oil.

Acrylic acid endo-8-(4-cyanonaphthalen-1-yl)-8-azabicyclo[3.2.1]oct-3-yl ester (159JP79)

154BG31 (2.0 g, 7.2 mmol) and triethylamine (1.45 g, 14.4 mmol) in dichloromethane (40 mL) were cooled to −20° C. and 3-chloropropionyl chloride (1.37 g, 10.8 mmol) in dichloromethane (5 mL) was added over 15 min and the reaction was allowed to warm to rt overnight. Partitioning of the reaction mixture between ethyl acetate (3×300 mL) and water (300 mL), drying of the combined organic phases over Na$_2$SO$_4$, filtration and removing of volatiles in vacuo afforded the title compound (920 mg, 40%) as a yellow solid.

1H-NMR (CDCl$_3$, 300 MHz) δ 8.20 (d, 2H, J=9.4), 7.81 (d, 1H, 9.4), 7.72-7.55 (m, 2H), 6.92 (d, 1H, J=9.4), 6.45 (m, 1H), 6.18 (m, 1H), 5.81 (m, 1H), 5.38 (m, 1H), 4.18 (br s, 2H), 2.62-2.07 (m, 8H).

3-Pyrrolidin-1-yl-propionic acid endo-8-(4-cyanonaphthalen-1-yl)-8-azabicyclo[3.2.1]oct-3-yl ester, fumarate (159JP82F6)

159JP79 (65 mg, 0.2 mmol) and pyrrolidine (2 mL) were heated to 100° C. overnight. Volatiles were concentrated in vacuo and the residue purified by vacuum flash chromatography, eluting with a gradient of 0-100% methanol in dichloromethane, to give of title compound (24 mg, 30%) as a white solid. The product was converted to the corresponding fumarate salt as described above.

R$_f$=0.42 (dichloromethane/MeOH, 10:1). LCMS m/z 404 [M+H]$^+$. $^1$H-NMR (CDCl$_3$, 300 MHz) δ 8.12 (d, 2H, J=8.8), 7.65 (d, 1H, J=8.1), 7.60-7.47 (m, 2H), 6.81 (d, 1H, J=8.1), 5.20 (t, 1H, J=5.2), 4.05 (br s, 2H), 3.38 (m, 1H), 2.80 (m, 1H), 2.65-2.40 (m, 8H), 2.20-1.82 (m, 9H). HPLC t$_R$=3.2 min (method III).

3-Imidazol-1-yl-propionic acid endo-8-(4-cyanonaphthalen-1-yl)-8-azabicyclo[3.2.1]oct-3-yl ester, fumarate (159JP83A)

159JP79 (70 mg, 0.22 mmol), imidazole (200 mg, 2.94 mmol) and 1-methyl-2-pyrrolidinone (0.5 mL) were placed in a sealed Pyrex vial and heated under microwave irradiation at 180° C. for 15 min. The reaction mixture was partitioned between ethyl acetate (2×100 mL) and water, the combined organic phases dried over Na$_2$SO$_4$, filtered and the solvent removed in vacuo. The residue was purified by preparative TLC (MeOH/dichloromethane 1:4, 5× eluted) to afford the title compound (48 mg, 55%) as a thick oil. The product was converted to the corresponding fumarate salt as described above.

R$_f$=0.32 (dichloromethane/MeOH 10:1). LCMS m/z 401 [M+H]$^+$. $^1$H-NMR (CDCl$_3$, 300 MHz) δ 8.18 (t, 2H, J=8.4), 7.67 (d, 1H, J=8.0), 7.60-7.42 (m, 2H), 7.02-6.88 (m, 2H), 6.79 (d, 1H, J=8.0), 5.22 (t, 1H, J=5.2), 4.22 (t, 2H, J=6.4), 4.00 (br s, 2H), 3.31 (t, 1H, J=7.0), 2.78-2.70 (m, 3H), 2.45-2.38 (m, 2H), 2.29 (t, 1H, J=8.0), 1.95-1.80 (m, 3H). HPLC t$_R$=3.8 min (method III).

3-Pyrazol-1-yl-propionic acid endo-8-(4-cyanonaphthalen-1-yl)-8-azabicyclo[3.2.1]oct-3-yl ester, fumarate (159JP85A)

This reaction was carried out as in 159JP83, starting with 159JP79 (184 mg, 0.57 mmol) and using pyrazole instead of imidazole to afford the title compound (88 mg, 39%) as a colorless oil. The product was converted to the corresponding fumarate salt as described above.

R$_f$=0.41 (dichloromethane/MeOH, 10:1). LCMS m/z 401 [M+H]$^+$.

$^1$H-NMR (CDCl$_3$, 300 MHz) δ 8.20 (m, 2H), 7.72 (d, 1H, J=8.1), 7.69-7.45 (m, 4H), 6.88 (d, 1H, J=8.0), 6.21 (t, 1H, J=2.1), 5.31 (t, 1H, J=5.0), 4.49 (t, 2H, J=6.6), 4.09 (br s, 2H), 2.95 (t, 1H, J=6.6), 2.48 (m, 2H), 2.11-1.90 (m, 6H). HPLC t$_R$=4.6 min (method III).

4-(2-Methyl-3-oxo-8-azabicyclo[3.2.1]oct-8-yl)naphthalene-1-carbonitrile (159JP84)

To 156AF03-217 (552 mg, 2 mmol) in THF (20 mL) under argon atmosphere at −78° C. was added dropwise lithium bis(trimethylsilyl)amide (2.6 mL, 2.6 mmol, 1 M in THF). After 30 min at −78° C., iodomethane (2.0 mL) was added over 1 min and the reaction was allowed to warm to rt overnight. Partitioning of the reaction mixture between ethyl acetate (2×500 mL) and water (500 mL), drying of the combined organic phases over Na$_2$SO$_4$, filtration, removing of volatiles in vacuo and purification by preparative TLC (ethyl acetate/n-heptane 1:4, 5× eluted) afforded the title compound (115 mg, 20%) as a thick oil.

R$_f$=0.55 (ethyl acetate/n-heptane 1:1). LCMS m/z 291 [M+H]$^+$. $^1$H-NMR (CDCl$_3$, 300 MHz) δ 8.25-8.10 (m, 2H), 7.71 (d, 1H, J=8.0), 7.65-7.50 (m, 2H), 6.92 (d, 1H, J=8), 4.32 (m, 1H), 4.12 (m, 1H), 2.98 (m, 2H), 2.43 & 2.37 (2d, 1H, J=2.2), 2.11-1.65 (m, 4H), 1.05 (d, 3H, J=6.8). HPLC t$_R$=4.3 min (method III).

4-(2-Methyl-8-azabicyclo[3.2.1]oct-8-yl)naphthalene-1-carbonitrile (159JP87A)

159JP84 (115 mg, 0.40 mmol) and p-toluenesulfonhydrazide (90 mg, 0.48 mmol) in absolute ethanol (1.0 mL) were refluxed overnight and the resulting white precipitate was filtered off, dried in vacuo and added to a vial containing sodium cyanoborohydride (101 mg, 1.60 mmol), N,N-dimethylformamide (2.0 mL), sulfolane (2.0 mL), p-toluenesulfonic acid (25 mg) and cyclohexane (2.0 mL). The resulting solution was heated at 110° C. for 2 days, poured into water (200 mL), extracted with ethyl acetate (2×200 mL), dried over $Na_2SO_4$, filtered, concentrated in vacuo and purified by preparative TLC (ethyl acetate/n-heptane 1:5, 5× eluted) to afford the title compound (25.3 mg, 22%) as thick oil.

$R_f$=0.70 (ethyl acetate/n-heptane, 1:1). LCMS m/z 277 [M+H]$^+$. $^1$H-NMR (CDCl$_3$, 300 MHz) δ 8.16 (d, 1H, J=8.0), 8.09 (d, 1H, J=8.2), 7.67 (d, 1H, J=8.0), 7.62-7.45 (m, 2H), 6.82 (d, 1H, J=8.1), 4.02 (m, 1H), 3.88 (m, 1H), 2.12 (m, 1H), 2.05-1.92 (m, 2H), 1.89-1.60 (m, 5H), 1.21 (m, 1H), 0.83 (d, 1H, J=6.8). HPLC $t_R$=6.2 min (method III).

4-(3-exo-Benzyl-3-endo-hydroxy-8-azabicyclo[3.2.1]oct-8-yl)naphthalene-1-carbonitrile (159JP92A)

To 183AF16-294 (188 mg, 0.65 mmol) in THF (10 mL) under argon atmosphere at −78° C. was dropwise added phenyllithium (0.56 mL, 0.85 mmol, 1.5 M in hexanes) and the reaction was allowed to warm to rt overnight. The reaction was quenched with sat. aq. NH$_4$Cl (100 mL), extracted with dichloromethane (3×200 mL), dried over $Na_2SO_4$, filtered and concentrated in vacuo. Purification by preparative TLC (ethyl acetate/n-heptane 1:4, 4× eluted) afforded the title compound (132 mg, 56%) as a yellow solid.

$R_f$=0.48 (ethyl acetate/n-heptane 1:1). LCMS m/z 369 [M+H]$^+$. $^1$H-NMR (CDCl$_3$, 300 MHz) δ 8.32 (d, 1H, J=8.6), 7.81 (m, 3H), 7.52-7.28 (m, 6H), 697 (d, 1H, J=7.8), 4.21 (m, 2H) 2.81 (m, 2H), 2.64 (br s, 2H), 2.30-2.11 (m, 4H), 1.52 (d, 2H, J=9.7). HPLC $t_R$=4.4 min (method III).

8-(4-Cyanonaphthalen-1-yl)-8-azabicyclo[3.2.1]oct-2-ene-2-carboxylic acid methyl ester (159JP95C)

8-Azabicyclo[3.2.1]oct-2-ene-2-carboxylic acid methyl ester (225 mg, 1.35 mmol, Davies H. M. L. et al., *J. Org. Chem.* 1991, 56, 5696-5700), 1-cyano-4-fluoronaphthalene (230 mg, 1.35 mmol) and pyridine (1.0 mL) were heated to 110° C. for 2 days and concentrated in vacuo. The residue was purified by preparative TLC (ethyl acetate/n-heptane 1:4, 5× eluted) to afford the title compound (25 mg, 6%) as a colorless oil.

$R_f$=0.49 (ethyl acetate/n-heptane, 1:1). LCMS m/z 319 [M+H]$^+$. $^1$H-NMR (CDCl$_3$, 300 MHz) 8.13-8.05 (m, 2H), 7.66 (d, 1H, J=8.0), 7.61-7.48 (m, 2H), 6.78 (d, 1H, J=8.0), 4.58 (d, 1H, J=5.8), 4.43 (t, 1H, J=6.0), 3.78 (s, 3H), 2.39 (m, 2H), 2.22 (m, 1H), 2.05-1.91 (m, 2H), 1.72 (m, 1H), 1.51 (m, 1H). HPLC $t_R$=4.8 min (method III).

8-(4-Cyanonaphthalen-1-yl)-8-azabicyclo[3.2.1]octane-2-carboxylic acid methyl ester (159JP97A)

159JP95C (12 mg, 0.038 mmol) and palladium (10 mg, 10 wt. % on activated carbon) in methanol (10 mL) were stirred for 3 days at rt under hydrogen atmosphere (balloon). The suspension was filtered through a pad of Celite, concentrated in vacuo and purification by preparative TLC (ethyl acetate/n-heptane, 1:4, 2× eluted) afforded the title compound (5.0 mg, 42%) as a colorless oil.

$R_f$=0.57 (ethyl acetate/n-heptane 1:1). LCMS m/z 321 [M+H]$^+$. $^1$H-NMR (CDCl$_3$, 300 MHz) δ 8.12 (m, 2H), 7.69 (d, 1H, J=8.0), 7.62-7.45 (m, 2H), 6.88 (d, 1H, J=8.1), 4.32 (m, 1H), 4.05 (m, 1H), 3.67 (s, 3H), 3.09 (m, 1H), 2.11-1.65 (m, 7H). HPLC $t_R$=5.2 min (method III).

4-(2-Hydroxymethyl-8-azabicyclo[3.2.1]oct-2-en-8-yl)naphthalene-1-carbonitrile (159JP98C)

To lithium aluminum hydride (1.3 mg, 0.034 mmol) in diethylether (1.0 mL) under argon atmosphere at 0° C. was added dropwise 159JP95C (7.2 mg, 0.023 mmol) in diethylether (1.0 mL). After stirring at 0° C. for 0.5 h, the reaction mixture was quenched with 2 M aq. NaOH (10 mL), acidified to pH 5 by adding 2 M hydrochloric acid, extracted with ethyl acetate (2×100 mL), dried over $Na_2SO_4$, filtered and concentrated in vacuo. Purification by preparative TLC (ethyl acetate/n-heptane 1:3, 3× eluted) afforded the title compound (2.8 mg, 43%) as a thick oil.

$R_f$=0.38 (ethyl acetate/n-heptane, 1:1). LCMS m/z 291 [M+H]$^+$. $^1$H-NMR (CDCl$_3$, 300 MHz) δ 8.11 (m, 2H), 7.64 (d, 1H, J=7.9), 7.60-7.44 (m, 2H), 693 (d, 1H, J=8.0), 5.22 (br s, 1H), 4.21 (m, 1H), 4.10 (br s, 2H), 4.04 (d, 1H, J=6.2), 3.21 (s, 1H), 2.20-1.78 (m, 5H). HPLC $t_R$=3.8 min (method III).

(1R,2R,3S,5S)-3-Benzoyloxy-8-(4-cyanonaphthalen-1-yl)-8-azabicyclo[3.2.1]octane-2-carboxylic acid methyl ester (195JP02A)

Adapting a protocol by Wolfe and Buchwald (*Tetrahedron Lett.*, 1997, 37, 6359-6362), 1-bromo-4-cyanonaphthalene (124 mg, 0.53 mmol, Cakmak O. et al., *Collect. Czech. Chem. Commun.* 2000, 65, 1791-1804), norcocaine (185 mg, 0.64 mmol), Pd$_2$(dba)$_3$ (23.8 mg, 0.026 mmol), rac-BINAP (24.7 mg, 0.040 mmol) and caesium carbonate (242 mg, 0.74 mmol) were placed in an argon flushed vial, toluene (1.0 mL) was added and the resulting mixture was stirred under argon atmosphere at 110° C. overnight. The crude was then concentrated in vacuo and purification by preparative TLC (ethyl acetate/n-heptane 1:4, 4× eluted) afforded the title compound (68 mg, 29%) as an oil.

$R_f$=0.21 (ethyl acetate/n-heptane 1:1). LCMS m/z 441 [M+H]$^+$. $^1$H-NMR (CDCl$_3$, 300 MHz) δ 8.32 (d, 1H, J=8.2), 8.19 (d, 1H, J=7.7), 8.11 (m, 2H), 7.77 (d, 1H, J=7.9), 7.72-7.45 (m, 5H), 6.91 (d, 1H, J=8.0), 5.58 (m, 1H), 4.64 (d, 1H, J=6.8), 4.20 (br s, 1H), 3.61 (s, 3H), 3.39 (m, 1H), 3.15 (dt, 1H, J=11.8, 2.0), 2.42 (m, 1H), 2.24-1.89 (m, 4H). HPLC $t_R$=5.5 min (method III).

(1R,2R,3S,5S)-4-(3-Hydroxy-2-hydroxymethyl-8-azabicyclo[3.2.1]oct-8-yl)naphthalene-1-carbonitrile (195JP05BX)

195JP02A (10 mg, 0.023 mmol) in dry diethylether (1.0 mL) was added to lithium aluminum hydride (1.8 mg, 0.046 mmol) in dry diethylether (5.0 mL) at 0° C. under argon atmosphere. After 10 min at 0° C., the reaction was quenched with 2 M NaOH (5.0 mL), pH was adjusted to pH 7 by addition of 2 M HCl, extracted with dichloromethane (3×100 mL), dried over $Na_2SO_4$, filtered and concentrated in vacuo. Purification by preparative TLC (dichloromethane/MeOH 10:1, 3× eluted) afforded the title compound (3.4 mg, 48%) as a thick oil.

$R_f$=0.31 (dichloromethane/MeOH 10:1). LCMS m/z 309 [M+H]$^+$. $^1$H-NMR (CDCl$_3$, 300 MHz) δ 8.12 (m, 2H), 7.69 (d, 1H, J=8.0), 7.65-7.48 (m, 2H), 6.83 (d, 1H, J=8.0), 4.32 (m, 1H), 4.25 (m, 1H), 4.13 (d, 1H, J=6.4), 3.98 (br s, 1H), 3.87 (dd, 1H, J=11.4, 3.9), 2.45-2.07 (m, 5H), 1.90-1.69 (m, 2H). HPLC $t_R$=2.5 min (method III).

2-Cyanoethyl endo-8-(4-cyanonaphthalen-1-yl)-8-azabicyclo[3.2.1]oct-3-yl N,N-diisopropylamidophosphite (165RL31)

88PS33 (34.0 mg, 0.122 mmol) was co-evaporated three times with toluene (5 mL) evaporated to dryness and dissolved in dichloromethane (2 mL) under argon atmosphere. 2-Cyanoethyl tetraisopropylphosphoroamidite (55.2 mg, 0.183 mmol) was dissolved in dichloromethane (2 mL) and added to the solution. N,N-Diisopropylamine (34 µL, 0.24 mmol) was added and the mixture cooled to 0° C. 1H-Tetrazole (3% in acetonitrile, 550 µL, 0.24 mmol) was added and the cooling was removed. The reaction mixture was stirred at rt for 2.5 hours and diluted with ethyl acetate (10 mL). The solution was washed with sat. sodium hydrogen carbonate solution (10 mL) followed by the addition of 2 drops of triethylamine to make sure the mixture was kept alkaline. The solution was dried over $Na_2SO_4$, filtered and evaporated to dryness. The residue was purified by column chromatography on silica gel eluting with a mixture of n-heptane/ethyl acetate/triethylamine (59/39/2), to give the title compound (24.9 mg, 46%) as a clear oil.

$R_f$=0.61 (n-heptane/ethyl acetate/TEA 59:39:2). $^1$H-NMR (CDCl$_3$, 300 MHz) δ 8.16 (m, 2H, Ar—H), 7.74 (d, 1H, J=8.1, Ar—H), 7.63 (m, 1H, Ar—H), 7.57 (m, 1H, Ar—H), 6.88 (d, 1H, J=8.1, Ar—H), 4.34 (m, 1H, Tr—H), 4.12 (m, 2H, Tr—H), 3.94-3.55 (m, 4H), 2.65 (t, 2H, J=6.2, CH$_2$), 2.48-1.93 (m, 8H), 1.21 (dd, 12H, J=6.8 and 4.4, CH—(CH$_3$)$_2$).

2-Cyanoethyl endo-8-(4-cyanonaphthalen-1-yl)-8-azabicyclo[3.2.1]oct-3-yl diisopropylamidophosphate (165RL37)

165RL31 (59 mg, 0.12 mmol) was dissolved in dichloromethane (5 mL), the solution cooled to −25° C. and tert-butyl hydroperoxide (70% in water, 88 µL, 0.62 mmol) was added. The reaction mixture was allowed to stir for 5 min, then the cooling bath was removed. After 1 hour stirring the mixture was diluted with dichloromethane (15 mL), washed with saturated sodium hydrogen carbonate (10 mL), dried over sodium sulfate, filtered and evaporated. The crude product was purified by column chromatography on silica gel eluting with ethyl acetate, to give the desired product (41.6 mg, 68%).

$R_f$=0.64 (ethyl acetate). LCMS m/z 495 [M+H]$^+$. $^1$H-NMR (CDCl$_3$, 300 MHz) δ 8.16 (m, 2H), 7.74 (d, 1H, J=8.1), 7.64 (m, 1H), 7.54 (m, 1H), 6.88 (d, 1H) J=8.1), 4.83 (m, 1H), 4.26-4.00 (m, 4H), 3.59-3.35 (m, 2H), 2.90-2.64 (m, 2H), 2.65-2.40 (m, 2H), 2.33-2.12 (m, 4H), 2.02 (m, 2H), 1.27 (dd, 12H, J=6.8 and 4.4).

2-Cyanoethyl ethyl endo-8-(4-cyanonaphthalen-1-yl)-8-azabicyclo[3.2.1]oct-3-yl phosphate (165RL38)

165RL31 (101 mg, 0.211 mmol) was co-evaporated three times with toluene (5 mL), evaporated to dryness and dissolved in dichloromethane (5 mL) under argon atmosphere. Abs. ethanol (11 µL. 0.19 mmol) was added, the reaction mixture cooled to −45° C. and 1H-tetrazole (3% in acetonitrile, 1.7 mL, 0.77 mmol) added. After 5 min the mixture was warmed to rt and stirred for 1 hour. It was then cooled to −25° C. and tert-butylhydroperoxide (70% in water, 0.14 mL, 0.96 mmol) was added. After 5 min the mixture was brought to rt and stirring was continued for another 1 hour. The mixture was diluted with dichloromethane (15 mL), washed with sodium hydrogen carbonate (10 mL), dried over sodium sulfate, filtered and evaporated. The crude product was purified by column chromatography on silica gel using methanol/ethyl acetate (1:9) followed by prep. HPLC. This gave 34.8 mg (38%) pure product.

$R_f$=0.48 (MeOH/ethyl acetate 1:9). LCMS m/z 440 [M+H]$^+$. $^1$H-NMR (CDCl$_3$, 300 MHz) δ 8.16 (m, 2H), 7.74 (d, 1H, J=8.1), 7.64 (m, 1H), 7.54 (m, 1H), 6.88 (d, 1H, J=8.1), 4.94 (m, 1H), 4.35-4.16 (m, 4H), 4.12 (m, 2H), 2.79 (t, 2H, J=6.0), 2.56-2.44 (m, 2H), 2.28-2.14 (m, 4H), 2.07-1.93 (m, 2H), 1.39 (t, 3H, J=7.0).

Ethyl endo-8-(4-cyanonaphthalen-1-yl)-8-azabicyclo[3.2.1]oct-3-yl hydrogen phosphate (165RL41)

165RL38 (34.8 mg, 0.103 mmol) and DBU (18.5 µL, 0.123 mmol) in THF (2 mL) was stirred at rt for 5 hours. The reaction mixture was diluted with dichloromethane (10 mL) and washed with water (10 mL). The pH of the water layer was adjusted to 3-4 with diluted hydrochloric acid and was extracted with ethyl acetate (5×10 mL). The combined organic layers were dried and evaporated. The product was further purified by preparative HPLC, giving the title compound (20 mg, 50%) as a white solid.

LCMS m/z 387 [M+H]$^+$. $^1$H-NMR (CD$_3$OD, 300 MHz) δ 8.23 (d, 1H, J=8.2), 8.05 (d, 1H, J=8.8), 7.79 (d, 1H, J=8.1), 7.66 (m, 1H), 7.57 (m, 1H), 7.03 (d, 1H, J=8.1), 4.63 (m, 1H), 4.12 (m, 2H), 3.69 (m, 2H), 2.48-2.34 (m, 4H), 2.25 (m, 1H), 2.20 (m, 1H), 2.02-1.90 (m, 2H), 1.28 (t, 3H, J=7.0).

Bis(2-cyanoethyl) endo-8-(4-cyanonaphthalen-1-yl)-8-azabicyclo[3.2.1]oct-3-yl phosphate (165RL42)

165RL31 (92 mg, 0.19 mmol) was co-evaporated three times with toluene (5 mL), evaporated to dryness and dissolved in dichloromethane (5 mL) under argon atmosphere. 3-Hydroxypropionnitrile (12 µL, 0.18 mmol) was added, the reaction mixture was cooled to −45° C. and 1H-tetrazole (3% in acetonitrile, 2.1 mL, 0.70 mmol) was added. After 5 min the mixture was brought to rt, stirred for 1 hour, cooled to −25° C. and tert-butylhydroperoxide (70% in water, 0.13 mL, 0.88 mmol) was added. After 5 min the mixture was brought to rt and stirring was continued for another 1 hour. The mixture was diluted with dichloromethane (15 mL), washed with sodium hydrogen carbonate (10 mL), dried over sodium sulfate, filtered and evaporated. The crude product was purified by preparative HPLC, giving the title compound (44.3 mg, 50%).

LCMS m/z 465 [M+H]$^+$.

Endo-8-(4-cyanonaphthalen-1-yl)-8-azabicyclo[3.2.1]oct-3-yl dihydrogen phosphate (165RL43)

165RL42 (44 mg, 0,095 mmol) was dissolved in THF (2 mL). Sodium hydroxide (0.5 M, 2 mL) was added and the reaction mixture was stirred for 3 hours at rt. The mixture was evaporated to dryness, the residue purified by preparative HPLC under buffer free conditions, giving the desired compound (16.2 mg, 48%).

LCMS m/z 359 [M+H]$^+$. $^1$H-NMR (CD$_3$OD, 300 MHz) δ 8.26 (d, 1H, J=8.2), 8.05 (d, 1H, J=8.8), 7.79 (d, 1H, J=8.1), 7.66 (m, 1H), 7.57 (m, 1H), 7.04 (d, 1H, J=8.1), 4.61 (m, 1H), 4.12 (m, 2H), 2.58-2.48 (m, 2H), 2.43-2.25 (m, 4H), 1.98-1.86 (m, 2H).

2-Cyanoethyl endo-8-(4-cyanonaphthalen-1-yl)-8-azabicyclo[3.2.1]oct-3-yl phenyl phosphate (165RL44)

165RL31 (94 mg, 0.20 mmol) was co-evaporated three times with toluene (4 mL), evaporated to dryness and dissolved in dichloromethane (5 mL) under argon atmosphere. A solution of phenol (17 mg. 0.18 mmol) in toluene (1 mL) was added, the reaction mixture cooled to −45° C. and 1H-tetrazole (3% in acetonitrile, 2.1 mL, 0.70 mmol) was added. After 5 min the mixture was warmed to rt and stirred for 1 hour. It was then cooled to −25° C. and tert-butylhydroperoxide (70% in water, 0.13 mL, 0.89 mmol) was added. After 5 min the mixture was brought to rt and stirring was continued for another 1 hour. The mixture was diluted with dichloromethane (15 mL), washed with sat. sodium hydrogen carbonate (10 mL), dried over sodium sulfate, filtered and evaporated. The crude product was purified by column chromatography on silica gel using n-heptane/ethyl acetate (1:9), giving the desired product (55.1 mg, 57%).

$R_f$=0.41 (n-heptane/ethyl acetate 1:9). LCMS m/z 488 [M+H]$^+$. $^1$H-NMR (CDCl$_3$, 300 MHz) δ 8.19 (m, 2H), 7.74 (d, 1H, J=8.1), 7.64 (m, 1H), 7.54 (m, 1H), 7.39 (m, 2H), 7.28 (m, 3H) 6.88 (d, 1H, J=8.1), 5.07 (m, 1H), 4.47-4.29 (m, 2H), 4.12 (m, 2H), 2.88-2.69 (m, 2H), 2.61-2.44 (m, 2H), 2.32-1.92 (m, 6H).

Endo-8-(4-cyanonaphthalen-1-yl)-8-azabicyclo[3.2.1]oct-3-yl phenyl hydrogen phosphate (165RL45)

165RL44 (55.1 mg, 0.11 mmol) and DBU (20 μL, 0.13 mmol) were stirred in THF (2 mL) at 50° C. for 3 hours. The reaction mixture was diluted with ethyl acetate (10 mL) and washed with sat. sodium hydrogen carbonate (5 mL). The organic layer was dried over sodium sulfate, filtered, evaporated and the residue purified by preparative HPLC to give the title compound (47 mg, 98%).

LCMS m/z 435 [M+H]$^+$. $^1$H-NMR (CD$_3$OD, 300 MHz) δ 8.19 (d, 1H, J=8.3), 8.03 (d, 1H, J=8.2), 7.75 (d, 1H, J=8.1), 7.63 (m, 1H), 7.54 (m, 1H), 7.33-7.25 (m, 4H), 7.04 (m, 1H), 6.97 (d, 1H, J=8.1), 4.74 (m, 1H), 4.06 (m, 2H), 2.46-2.30 (m, 4H), 2.18-2.13 (m, 2H), 1.93-1.86 (m, 2H).

N-[8-(4-cyanonaphthalen-1-yl)-8-azabicyclo[3.2.1]oct-3-yl]acetamide (165RL51)

To a −30° C. solution of acetyl chloride (15 μL, 0.21 mmol) in DMF (1.5 mL) was added dropwise a solution of 165RL21 (54 mg, 0.20 mmol) and DIPEA (37 μL, 0.21 mmol) in DMF (3.5 mL). After 1 hour of stirring the reaction mixture was brought to rt and allowed to react overnight. Water (20 mL) was then added and the mixture extracted with ethyl acetate (3×20 mL). The combined organic layers were dried over sodium sulfate, filtered and evaporated. The crude product was purified by column chromatography on silica gel using ethyl acetate/MeOH (9:1) to give the desired compound (35 mg, 56%).

$R_f$=0.32 (ethyl acetate/MeOH 9:1). LCMS m/z 320 [M+H]$^+$. $^1$H-NMR (CDCl$_3$, 300 MHz, diastereomers endo:exo 3:2) δ 8.19 (m, 2H, Ar—H), 7.72 (d, 1H, J=8.0, Ar—H), 7.63 (m, 1H, Ar—H), 7.54 (m, 1H, Ar—H), 6.86 (m, 1H, Ar—H), 5.95 (m, 0.6H, CONH), 5.53 (m, 0.4H, CONH), 4.47-4.30 (m, 1H, Tr—H), 4.15 (m, 2H, Tr—H), 2.66-2.53 (m, 1H, Tr—H), 2.20-1.79 (m, 7H, Tr—H), 2.02 and 2.00 (2s, 3H, COCH$_3$).

3-Chloro-N-[8-(4-cyanonaphthalen-1-yl)-8-azabicyclo[3.2.1]oct-3-yl]propanamide (165RL50)

This compound was synthesized in the same way as 165RL23 using 165RL21 (320 mg, 1.15 mmol), 3-chloropropionyl chloride (120 μL, 1.27 mmol), DIPEA (220 μL, 1.27 mmol) and DMF (10 mL). The crude product was purified by column chromatography using ethyl acetate/MeOH (95:5) to give the title compound (318 mg, 75

$R_f$=0.54 (ethyl acetate/MeOH 95:5). LCMS m/z 368 [M+H]$^+$. $^1$H-NMR (CDCl$_3$, 300 MHz, diastereomers endo:exo 3:2) δ 8.17 (m, 2H, Ar—H), 7.73 (d, 1H, J=8.0, Ar—H), 7.65 (m, 1H, Ar—H), 7.56 (m, 1H, Ar—H), 6.87 (m, 1H, Ar—H), 6.09 (m, 0.6H, CONH), 5.57 (m, 0.4H, CONH), 4.52-4.34 (m, 1H, Tr—H), 4.17 (m, 2H, Tr—H), 3.86-3.83 (m, 2H), 2.64 (m, 2H), 2.65-2.58 (m, 1H, Tr—H), 2.22-1.85 (m, 7H, Tr—H).

N-[8-(4-cyanonaphthalen-1-yl)-8-azabicyclo[3.2.1]oct-3-yl]-3-(4-ethylpiperazin-1-yl)propanamide, dihydrochloride (165RL52)

165RL50 (65 mg, 0.18 mmol), 1-ethylpiperazine (45 μL, 0.35 mmol) and potassium carbonate (49 mg, 0.35 mmol) were stirred in acetonitrile (6 mL) at 50° C. for 2 days. The reaction mixture was diluted with ethyl acetate (15 mL) and washed with water (2×10 mL). The organic solution was dried over sodium sulfate, filtered and evaporated. The product was purified by column chromatography using ethyl acetate/MeOH (9:1) to give the title compound (37 mg, 46%) pure product.

$R_f$=0.13 (ethyl acetate/MeOH 9:1). LCMS m/z 446 [M+H]$^+$. $^1$H-NMR (CDCl$_3$, 300 MHz, diastereomers endo:exo 3:2) δ 8.78 (m, 0.6H), 8.57 (m, 0.4H), 8.17 (m, 2H), 7.72 (d, 1H, J=8.0), 7.64 (m, 1H), 7.54 (m, 1H), 6.88 (m, 1H), 4.52-4.34 (m, 1H), 4.15 (m, 2H), 2.78-2.32 (m, 14H), 2.20-1.75 (m, 8H), 1.08 and 1.07 (2t, 3H, J=7.2).

N-[8-(4-Cyanonaphthalen-1-yl)-8-azabicyclo[3.2.1]oct-3-yl]-3-diethylaminopropionamide, hydrochloride (165RL53)

The title compound (16 mg, 19%) was synthesized in the same way as 165RL52 using 165RL50 (80 mg, 0.21 mmol), diethylamine (45 μL, 0.44 mmol), potassium carbonate (60 mg, 0.44 mmol) and acetonitrile (6 mL).

$R_f$=0.15 (ethyl acetate/MeOH 9:1). LCMS m/z 405 [M+H]$^+$. $^1$H-NMR (CDCl$_3$, 300 MHz, diastereomers endo:exo 3:2) δ 9.07 (m, 0.6H), 8.76 (m, 0.4H), 8.17 (m, 2H), 7.72 (d, 1H, J=8.0), 7.64 (m, 1H), 7.54 (m, 1H), 6.88 (m, 1H), 4.52-4.34 (m, 1H), 4.15 (m, 2H), 2.92-2.48 (m, 7H), 2.46-2.33 (m, 2H), 1.98-1.76 (m, 7H), 1.08 and 1.06 (2t, 6H, J=7.2).

N-[8-(4-cyanonaphthalen-1-yl)-8-azabicyclo[3.2.1]oct-3-yl]-3-(1H-imidazol-1-yl)propanamide hydrochloride (165RL55)

165RL50 (61 mg, 0.17 mmol), imidazole (53 mg, 0.83 mmol), sodium iodide (10 mg, 0.07 mmol) and dichloromethane (6 mL) were shaken in a vial at 80° C. for 2 days. The reaction mixture was diluted with ethyl acetate (15 mL) and washed with water (2×10 mL). The organic solution was dried over sodium sulfate, filtered and evaporated. The residue was purified by column chromatography using a stepwise gradient of 10-100% methanol in ethyl acetate to give the title compound (32 mg, 47%).

$R_f$=0.08 (ethyl acetate/MeOH 9:1). LCMS m/z 400 [M+H]$^+$. $^1$H-NMR (CDCl$_3$, 300 MHz, diastereomers endo: exo 3:2) δ 8.12 (m, 2H), 7.72 (d, 1H, J=8.0), 7.63 (m, 1H), 7.53 (m, 1H), 7.45 (s, 1H), 7.02 (s, 1H), 6.94 (s, 1H), 6.82 (m, 1H), 6.34 (m, 0.6H), 6.24 (m, 0.4H), 4.41-4.22 (m, 3H), 4.08 (m, 2H), 2.68-2.48 (m, 3H), 2.11-1.69 (m, 7H).

(2-Ethoxyethoxy)acetic acid (165RL54)

2-Ethoxyethanol (0.88 mL, 11 mmol) and sodium hydride (60% in oil, 1.08 g, 27 mmol) were stirred in DMF (20 mL) for 5 min. Iodoacetic acid (2.02 g, 10.9 mmol) was dissolved in DMF (20 mL) and added dropwise to the suspension. The thick orange suspension was stirred at rt for 3 hours. The reaction was quenched by slowly adding water (10 mL), followed by hydrochloric acid (4 M, 5 mL). The reaction mixture was extracted with dichloromethane (3×50 mL) and the combined organic layers dried over sodium sulfate, filtered and evaporated yielding a clear oil. The residue was purified by distillation under reduced pressure to give the product (1.1 g, 68%) as an oil.

$^1$H-NMR (CDCl$_3$, 300 MHz) δ 10.61 (br, 1H), 4.16 (s, 2H), 3.74 (m, 2H), 3.56 (m, 4H), 1.21 (t, 3H, J=7.0).

N-[8-(4-Cyanonaphthalen-1-yl)-8-azabicyclo[3.2.1]oct-3-yl]-2-(ethoxyethoxy)acetamide (165RL57)

165RL54 (19 mg, 0.13 mmol), O-benzotriazol-1-yl-N,N,N,N-tetramethyluronium tetrafluorophosphate (HBTU, 49 mg, 0.13 mmol), 1-hydroxybenzotriazole (18 mg, 0.13 mmol) and triethylamine (37 PL, 0.26 mmol) were dissolved in DMF (4 mL). 165RL21 (36 mg, 0.13 mmol)) was added and the mixture was shaken at rt for 30 min. The solvent was removed in vacuo and the product was purified by flash chromatography on silica gel using ethyl acetate/methanol (9:1) as eluent, giving the desired compound (38.1 mg, 72%).

$R_f$=0.46 (ethyl acetate/MeOH 9:1). LCMS m/z 408 [M+H]$^+$. $^1$H-NMR (CDCl$_3$, 300 MHz, diastereomers endo: exo 3:2) δ 8.17 (m, 2H), 7.72 (d, 1H, J=8.0), 7.63 (m, 1H), 7.54 (m, 1H), 7.29 (m, 0.6H), 7.05 (m, 0.4H), 6.88 (m, 1H), 4.52-4.33 (m, 1H), 4.16 (m, 2H), 4.00 and 4.01 (2s, 2H), 3.76-3.51 (m, 6H), 2.63-2.52 (m, 1H), 2.18-1.85 (m, 7H), 1.26 and 1.20 (2t, 3H, J=7.0).

1-(4-Cyanonaphthalen-1-yl)piperidine-3-carboxylic acid ethyl ester (165RL60)

1-Cyano-4-fluoronaphthalene(1.0 g, 5.84 mmol) and ethyl nipecotate (3.63 mL, 23.4 mmol) were dissolved in pyridine (5 mL) and stirred at 115° C. for 20 hours. After cooling to rt ethyl acetate (50 mL) was added and the solution washed with HCl (0.4 M, 2×30 mL). The combined aqueous layers were extracted with ethyl acetate (30 mL). The combined organic layers were washed with sat. sodium hydrogen carbonate (30 mL), brine (30 mL), dried and evaporated. The crude product was purified by silica gel column chromatography eluted with a stepwise gradient of 0-70% ethyl acetate in n-heptane to give the title compound (1.23 g, 68%) as a yellowish oil.

LCMS m/z 309 [M+H]$^+$. $^1$H-NMR (CDCl$_3$, 300 MHz) δ 8.20 (m, 2H), 7.83 (d, 1H, J=7.9), 7.63 (m, 2H), 7.06 (d, 1H, J=7.9), 4.18 (q, 2H, J=7.1), 3.59 (m, 1H), 3.38 (m, 1H), 3.07 (m, 1H), 2.89 (m, 2H), 2.17 (m, 1H), 2.02 (m, 2H), 1.71 (m, 1H), 1.25 (t, 3H, J=7.1).

4-(2-Methylpiperidin-1-yl)naphthalene-1-carbonitrile (165RL62)

1-Cyano-4-fluoronaphthalene (100 mg, 0.58 mmol), 2-methylpiperidine (0.28 mL, 2.3 mmol) and DBU (0.01 mL, 59 μmol) were dissolved in pyridine (2 mL) and stirred at 60° C. for 3 days. The temperature was raised to 110° C. and the stirring was continued for 10 days. The reaction was worked up in the same way as for 198RL60. The crude compound was purified by preparative TLC followed by preparative HPLC to give the title compound (27.4 mg, 19%) as a colourless oil, which was stored under argon atmosphere.

LCMS m/z 251 [M+H]$^+$. $^1$H-NMR (CDCl$_3$, 300 MHz) δ 8.33 (d, 1H, J=8.2), 8.19 (d, 1H, J=8.2), 7.84 (d, 1H, J=7.8), 7.59 (m, 2H), 7.10 (d, 1H, J=7.8), 3.53 (m, 1H), 3.28 (m, 1H), 2.75 (m, 1H), 2.01 (m, 1H), 1.88-1.53 (m, 5H), 0.92 (d, 3H, J=6.3).

1-(4-Cyanonaphthalen-1-yl)piperidine-3-carboxylic acid (165RL63)

198RL60 (862 mg, 2.80 mmol) was dissolved in THF (5.6 mL) and sodium hydroxide (1 M, 5.6 mL). The reaction mixture was not homogenous and ethanol (1 mL) was added to get a clear solution which was stirred at rt overnight. The solution was made acidic by addition of 4 M HCl, followed by extraction with ethyl acetate (3×50 mL). The combined organic layers were dried over sodium sulfate, filtered and evaporated to give the title compound (746 mg, 95%) as a pure white solid.

LCMS m/z 281 [M+H]$^+$. $^1$H-NMR (CDCl$_3$, 300 MHz) δ 8.18 (m, 2H), 7.83 (d, 1H, J=7.9), 7.63 (m, 2H), 7.08 (d, 1H, J=7.9), 3.60 (m, 1H), 3.36 (m, 1H), 3.12 (m, 1H), 3.03-2.83 (m, 2H), 2.19 (m, 1H), 2.13 (m, 2H), 1.70 (m, 1H).

[1-(4-Cyanonaphthalen-1-yl)piperidin-3-ylmethyl]carbamic acid tert-butyl ester (165RL65)

1-Cyano-4-fluoronaphthalene (273 mg, 1.60 mmol), tert-butyl (piperidin-3-ylmethyl)carbamate (411 mg, 1.92 mmol) and DBU (25 μl, 0.16 mmol) were dissolved in pyridine (4 mL) and stirred at 60° C. for 4 days. The reaction was worked up in the same way as for 198RL60 followed by purification using silica gel column chromatography eluted with a stepwise gradient of 0-70% ethyl acetate in n-heptane, giving the desired compound (416 mg, 71%) as a white solid.

$^1$H-NMR (CDCl$_3$, 300 MHz) δ 8.18 (m, 2H, Ar—H), 7.81 (d, 1H, J=7.9, Ar—H), 7.61 (m, 2H, Ar—H), 7.00 (d, 1H, J=7.9, Ar—H), 4.62 (m, 1H), 3.45 (m, 2H) 3.14 (m, 2H), 2.81 (m, 1H), 2.59 (m, 1H), 2.14 (m, 1H), 1.93 (m, 3H), 1.42 (s 9H), 1.24 (m, 1H).

4-(3-Aminomethylpiperidin-1-yl)naphthalene-1-carbonitrile(165RL66)

165RL65 (416 mg, 1.14 μmol) was dissolved in dichloromethane (20 mL) followed by the addition of TFA (5 mL). The mixture was stirred at rt for 3 h and the solvents removed in vacuo. Sodium hydroxide (0.2 M, 10 mL) was added and the mixture extracted with ethyl acetate (3×10 mL). The combined organic layers were dried over sodium sulfate, filtered and evaporated to give the title compound (292 mg, 97%) as a yellow oil.

LCMS m/z 266 [M+H]$^+$. $^1$H-NMR (CDCl$_3$, 300 MHz) δ 8.15 (m, 2H), 7.79 (d, 1H, J=7.9), 7.59 (m, 2H), 7.00 (d, 1H,

J=7.9), 3.51 (m, 1H), 3.40 (m, 1H) 2.85-2.61 (m, 3H), 2.53 (m, 1H), 2.03-1.74 (m, 6H), 1.18 (m, 1H).

N-[1-(4-Cyanonaphthalen-1-yl)piperidin-3-ylmethyl]acetamide (165RL70)

To a solution of 165RL66 (40 mg, 151 μmol) and triethylamine (23 μL, 17 μmol) in dichloromethane (1 mL) was added acetyl chloride (12 μL, 17 μmol). The mixture was stirred at rt overnight, diluted with ethyl acetate (10 mL) and washed with HCl (0.5 M, 10 mL). The aqueous phase was re-extracted with ethyl acetate (2×20 mL). The combined organic layers were washed with sat. sodium hydrogen carbonate (10 mL) and brine (10 mL), dried over sodium sulfate, filtered and evaporated. The remaining solid was purified by silica gel column chromatography eluted with a stepwise gradient of 0-70% ethyl acetate in n-heptane to give the title compound (26 mg, 56%) as a solid.

$R_f$=0.65 (ethyl acetate/MeOH 9:1). LCMS m/z 308 [M+H]$^+$. $^1$H-NMR (CDCl$_3$, 300 MHz) δ 8.15 (m, 2H), 7.76 (d, 1H, J=7.9), 7.58 (m, 2H), 7.00 (d, 1H, J=7.9), 5.74 (m, 1H), 3.42 (m, 2H), 3.27 (m, 2H), 2.78 (m, 1H), 2.59 (m, 1H), 2.14 (m, 1H), 2.01-1.86 (m, 3H), 1.97 (s, 3H), 1.25 (m, 1H).

4-(3-Ethylaminomethylpiperidin-1-yl)naphthalene-1-carbonitrile hydrochloride (165RL72sec) and 4-(3-Diethylaminomethylpiperidin-1-yl)naphthalene-1-carbonitrile hydrochloride (165RL72tert)

165RL66 (106 mg, 0.40 mmol) was dissolved in methanol (20 mL). The pH was adjusted to ~5 by addition of acetic acid (~0.5 mL). Acetaldehyde (45 μL, 0.80 mmol) was added and the reaction mixture was stirred for 5 min before the addition of sodium cyanoborohydride (175 mg, 2.80 mmol). The mixture was stirred at rt for 3 hours, sodium hydroxide (2 M, 1 mL) was added followed by water (10 mL) and stirring maintained for 5 min. Sodium hydroxide (1 M, 25 mL) was added and the mixture extracted with ethyl acetate (3×40 mL). The combined organic layers were dried over sodium sulfate, filtered and evaporated to give a solid. Purification by silica gel column chromatography eluted with a stepwise gradient of 0-60% of methanol in ethyl acetate (1:9) in n-heptane and pooling of the appropriate fractions gave the monoethylated compound 165RL72sec and the diethylated compound 165RL72tert. Both products were further purified by preparative. HPLC, giving 22.3 mg (19%) of 165RL72sec and 9.8 mg (8%) of 165RL72tert.

165RL72sec: LCMS m/z 294 [M+H]$^+$. $^1$H-NMR (CDCl$_3$, 300 MHz) δ 8.17 (m, 2H), 7.50 (d, 1H, J=7.9), 7.59 (m, 2H), 7.01 (d, 1H, J=7.9), 3.52 (m, 1H), 3.41 (m, 1H), 2.81 (m, 1H), 2.75-2.51 (m, 4H), 2.13 (m, 1H), 2.06-1.70 (m, 5H), 1.25 (m, 1H), 1.11 (t, 3H, J=7.1).

165RL72tert: LCMS m/z 322 [M+H]$^+$. $^1$H-NMR (CDCl$_3$, 300 MHz) δ 8.17 (m, 2H), 7.80 (d, 1H, J=7.9), 7.64 (m, 1H), 7.56 (m, 1H), 7.11 (d, 1H, J=7.9), 3.63 (m, 1H), 3.42 (m, 1H), 2.81 (m, 1H), 2.64-2.42 (m, 5H), 2.33 (m, 2H), 2.13 (m, 1H) 1.90 (m, 3H), 1.18 (m, 1H), 1.00 (t, 6H, J=7.1).

1-(4-Cyanonaphthalen-1-yl)piperidine-3-carbonitrile (165RL73-3) and 1-(4-Cyanonaphthalen-1-yl)piperidine-3-carboxamide (165RL73-5)

165RL63 (314 mg, 1.12 mmol), DMF (3 drops) and dichloromethane (4 mL) was put in a flask under argon atmosphere and the solution cooled to 0° C. in an ice bath. Oxalyl chloride (147 μL, 1.68 mmol) was slowly added. The ice bath was removed and the mixture was stirred for 4 hours. Solvents and the excess of oxalyl chloride was then removed in vacuo. The remaining acid chloride was taken up in dichloromethane (10 mL) under argon atmosphere. Ammonium hydroxide solution (28% in water) (0.16 mL, 2.24 mmol) was slowly added and the mixture was stirred at rt over night. The reaction mixture was diluted with ethyl acetate (50 mL) and washed with sodium hydroxide (1 M, 30 mL). The organic layer was dried over sodium sulfate, filtered and evaporated. The solid was purified by silica gel column chromatography eluted with a stepwise gradient of 0-80% ethyl acetate in n-heptane to give the nitrile 165RL73-3 (9.5 mg, 3%) and the amide 165RL73-5 (66 mg, 21%).

165RL73-3: LCMS m/z 262 [M+H]$^+$. $^1$H-NMR (CDCl$_3$, 300 MHz) δ 8.30 (m, 1H), 8.21 (m, 1H), 7.84 (d, 1H, J=7.9), 7.66 (m, 2H), 7.05 (d, 1H, J=7.9, Ar—H), 3.48-3.06 (m, 5H), 2.26-1.88 (m, 4H).

165RL73-5: LCMS m/z 280 [M+H]$^+$. $^1$H-NMR (CDCl$_3$, 300 MHz) δ 8.19 (m, 1H), 8.11 (m, 1H), 7.82 (d, 1H, J=7.9), 7.61 (m, 2H), 7.06 (d, 1H, J=7.9), 6.10 and 5.86 (2s, 2H, CO—NH$_2$), 3.53 (1H, m), 3.28 (m, 1H), 3.15 (m, 1H), 2.96 (m, 1H) 2.80 (m, 1H), 2.14-1.82 (m, 4H).

4-(3-Fluoropiperidin-1-yl)naphthalene-1-carbonitrile (165RL74)

3-Fluoropiperidine hydrochloride (106 mg, 0.76 mol) was dissolved in sodium hydroxide (1 M, 10 mL) and extracted with dichloromethane (4×10 mL), the combined extracts were dried over sodium sulfate, filtered and evaporated. Pyridine (2 mL) was added, followed by 1-cyano-4-fluoronaphthalene (108 mg, 0.63 mmol) and the vial was shaken at 110° C. overnight. GC-MS and TLC showed only very little conversion. DBU (10 μL) was added and the shaking was continued for 2 weeks at 110° C., after which GC-MS showed ~50% conversion. The reaction was worked up in the same way as 165RL60 and purified by silica gel column chromatography eluted with a stepwise gradient of 0-60% ethyl acetate in n-heptane to give the title compound (29.3 mg, 12%) as a solid.

LCMS m/z 255 [M+H]$^+$. $^1$H-NMR (CDCl$_3$, 300 MHz) δ 8.22 (m, 2H), 7.83 (d, 1H, J=7.9), 7.63 (m, 2H), 7.03 (d, 1H, J=7.9), 4.92 (dm, 1H, $J_{H-F}$=48), 3.45-3.04 (m, 4H), 2.23-1.79 (m, 4H).

trans-4-(4-Hydroxycyclohexylaniino)naphthalene-1-carbonitrile (165RL96)

1-Cyano-4-fluoronaphthalene (1.00 g, 5.84 mmol), trans-4-amino cyclohexanol hydrochloride (1.33 g, 8.76 mmol) and potassium carbonate (4.0 g, 29 mmol) were stirred in DMSO (20 mL) at 120° C. overnight. The reaction mixture was then diluted with dichloromethane (100 mL) and washed with water (3×50 mL). The solution was dried over sodium sulfate, filtered and evaporated. The residue was purified by silica gel column chromatography eluted with a stepwise gradient of 0-70% ethyl acetate in n-heptane, giving the title compound (1.187 g, 92%) as a colorless solid.

$R_f$=0.74 (ethyl acetate). LCMS m/z 267 [M+H]$^+$. $^1$H-NMR (CDCl$_3$, 300 MHz) δ 8.16 (m, 1H), 7.75 (m, 2H), 7.64 (m, 1H), 7.52 (m, 1H), 6.58 (m, 1H), 3.76 (m, 1H), 3.54 (m, 1H), 2.27 (m, 2H), 2.10 (m, 2H), 1.70-1.30 (m, 5H), 2.26 (m, 1H).

Methanesulfonic acid trans-4-(4-cyanonaphthalen-1-ylamino)cyclohexyl ester (165RL97)

165RL96 (300 mg, 1.13 mmol) and triethylamine (188 µL, 1.35 mmol) was dissolved in dichloromethane (10 mL). The solution was cooled to 0° C. and methanesulfonylchloride (105 µL, 1.35 mmol) was added. After 10 min the ice bath was removed and the mixture allowed to react at rt overnight. The reaction mixture was diluted with dichloromethane (20 mL), washed with water (20 mL) followed by sat. $NaHCO_3$ (20 mL). The organic layer was dried over sodium sulfate, filtered and evaporated to give the mesylated product (353 mg) which was used without further purification.

4-(7-Azabicyclo[2.2.1]hept-7-yl)naphthalene-1-carbonitrile hydrochloride (198RL01)

165RL97 (129 mg, 374 µmol) was stirred in DMF/toluene (1:1, 20 mL) at −40° C. and potassium tert-butoxide (42 mg, 374 µmol) was added. The stirring was continued for 30 min before the reaction mixture was brought to rt. After 2 hours, more potassium tert-butoxide (20 mg, 0.18 mol) was added and the reaction was stirred overnight. The mixture was diluted with dichloromethane (50 mL) and washed with water (3×30 mL). The organic layer was dried over sodium sulfate, filtered and evaporated and the residue purified by column chromatography on silica gel using dichloromethane as eluent, yielding the desired compound (67.8 mg, 73%).

$R_f$=0.75 (dichloromethane). LCMS m/z 249 [M+H]$^+$. $^1$H-NMR (CDCl$_3$, 300 MHz) δ 8.19 (m, 2H, Ar—H), 7.72 (d, 1H, J=8.0, Ar—H), 7.63 (m, 1H, Ar—H), 7.53 (m, 1H, Ar—H), 6.88 (d, 1H, J=8.0, Ar—H), 4.31 (m, 2H), 1.98 (m, 4H), 1.54 (m, 4H).

N'-[8-(4-cyanonaphthalen-1-yl)-8-azabicyclo[3.2.1]oct-3-yl]-4-methylbenzenesulfonylhydrazone (173FBA60a)

To a mixture of ketone 156AF03-217 (500 mg, 1.811 mmol) in abs. ethanol (6 mL) was added p-toluenesulfonylhydrazine (405 mg, 2.173 mmol) and the reaction was stirred and refluxed for 1 h. The mixture was then cooled and the precipitated white solid filtered and washed with abs. ethanol to give 173FBA60a (738 mg, 92%).

LCMS m/z 445 [M+H]$^+$. $^1$H-NMR (CDCl$_3$, 300 MHz) δ 8.25-8.15 (m, 2H), 7.88 (d, J=8.3, 2H), 7.77 (d, J=8.0, 1H), 7.73-7.63 (m, 1H), 7.63-7.53 (m, 1H), 7.35 (d, J=8.0, 2H), 6.91 (d, J=8.0, 1H), 4.32-4.19 (m, 2H), 3.01-2.88 (m, 1H), 2.82-2.69 (m, 1H), 2.69-2.49 (m, 2H), 2.46 (s, 3H), 2.11-1.96 (m, 2H), 1.79-1.66 (m, 1H), 1.62-1.48 (m, 1H).

4-[2-(Hydroxymethyl)piperidin-1-yl]naphthalene-1-carbonitrile, tri (173FBA70e)

A solution of 1-cyano-4-fluoronaphthalene (200 mg, 1.168 mmol) in pyridine (0.5 mL) was transferred to a Pyrex tube and 2-piperidinemethanol (538 mg, 4.67 mmol) was added. The tube was capped and exposed to microwave irradiation (200° C., 60 min). The reaction mixture was diluted with ethyl acetate, washed with 0.4 N HCl and saturated aqueous $NaHCO_3$. The organic phase was dried and evaporated to give a crude product which was purified by preparative TLC (65:35 n-heptane/ethyl acetate), followed by further purification by preparative HPLC to give 173FBA70e (15 mg, 5%).

LCMS m/z 267 [M+H]$^+$. $^1$H-NMR (CDCl$_3$, 300 MHz) δ 8.30 (d, J=8.1, 1H), 8.20 (d, J=7.8, 1H), 7.83 (d, J=7.8, 1H), 7.72-7.53 (m, 2H), 7.22 (d, J=8.0, 1H), 3.67-3.48 (m, 3H), 3.41-3.26 (m, 1H), 3.00-2.82 (m, 1H), 2.10-1.55 (m, 6H).

3-exo-[8-(4-Cyanonaphthalen-1-yl)-3-endo-hydroxy-8-azabicyclo[3.2.1]oct-3-yl]-N,N-dimethylpropanamide (173FBA51bH)

To a solution of N,N-diisopropylamine (69.6 mg, 0.688 mmol) in dry THF (0.5 mL) at 0° C. was added dropwise n-butyl lithium (1.6 M in n-hexane, 0.688 mmol, 0.43 mL) and the mixture allowed to stir for 10 min. Then a solution of N,N-dimethylacetamide in dry THF (0.5 mL) was added (30 mg, 0.344 mmol) and the mixture stirred at rt. After 10 min a solution of epoxide 183AF16-294 (50 mg, 0.172 mmol) in dry THF (0.5 mL) was added at rt and the solution stirred at reflux for 4 h. The reaction was quenched by sat. aqueous $NH_4Cl$ and water and extracted with diethylether. The organic phase was dried over sodium sulfate, filtered and evaporated to give a crude product which was purified by preparative TLC using dichloromethane/acetone 8:2 as eluent and a second one using ethyl acetate/heptane/MeOH 8:1.5:0.5 as eluent to give 173FBA51bH as a white solid (4.0 mg, 6%).

LCMS m/z 378 [M+H]$^+$. $^1$H-NMR (CDCl$_3$, 300 MHz) δ 8.18 (d, J=8.8, 2H), 7.76 (d, J=8.1, 1H), 7.69-7.60 (m, 1H), 7.60-7.48 (m, 1H), 6.92 (d, J=8.1, 1H), 4.22-4.10 (m, 2H), 3.08 (s, 3H), 3.00 (s, 3H), 2.55 (t, J=6.3, 2H), 2.42-2.32 (m, 2H), 2.23-2.15 (m, 2H), 2.07-1.85 (m, 6H).

2-exo-[8-(4-Cyanonaphthalen-1-yl)-3-endo-hydroxy-8-azabicyclo[3.2.1]oct-3-yl]-N,N-dimethylethanesulfonamide (173FBA56b3)

To a solution of N,N-diisopropylamine (64.3 mg, 0.636 mmol) in dry THF (0.5 mL) at 0° C. was added dropwise n-butyl lithium (1.6 M in hexane, 0.636 mmol, 0.4 mL) and the mixture allowed to stir for 10 min. A solution of N,N-dimethylmethanesulfonamide (39 mg, 0.318 mmol) in dry THF (0.5 mL) was added and the mixture stirred at rt. After 10 min a solution of epoxide 183AF16-294 (46 mg, 0.159 mmol) in dry THF (0.5 mL) was added at rt and the solution stirred for 3 h. The reaction mixture was then quenched by sat. aqueous $NH_4Cl$ and water and extracted with diethylether. The organic phase was dried over sodium sulfate, filtered and evaporated to give a crude product, which was purified by preparative TLC using a 1:1 ethyl acetate/heptane mixture as eluent. to give pure 173FBA56b3 as a white solid (6.2 mg, 9%).

LCMS m/z 414 [M+H]$^+$. $^1$H-NMR (CDCl$_3$, 300 MHz) δ 8.25-8.17 (m, 1H), 8.16-8.08 (m, 1H), 7.52-7.40 (m, 2H), 7.33 (d, J=7.8, 1H), 6.85 (d, J=7.8, 1H), 4.12-3.96 (m, 2H), 2.77 (s, 6H), 2.76-2.63 (m, 2H), 2.49 (s, 2H), 2.20-2.10 (m, 2H), 2.06-1.94 (m, 2H), 1.55-1.42 (m, 2H), 1.42-1.32 (m, 2H).

3-Endo-hydroxy-3-exo-methyl-8-azabicyclo[3.2.1]octane-8-carboxylic acid tert-butyl ester (197FBA17d)

To a suspension of NaH (55-65% dispersion in mineral oil, 1.45 g, 33.3 mmol) in DMSO (20 mL) was slowly added trimethylsulfoxonium iodide (7.33 g, 33.3 mmol) and the reaction mixture was allowed to stir during 1 h. A solution of Boc-tropinone (5.0 g, 22.2 mmol) was added and the mixture was stirred at rt during 20 h. Partitioning of the mixture between ethyl acetate and water, drying of the organic layer over sodium sulfate, filtration and evaporation gave the crude epoxide spiro[8-azabicyclo[3.2.1]octane-3,2'-oxirane]-8-carboxylic acid tert-butyl ester (197FBA10a), which was used in the next step without further purification. To a solution of 197FBA10a (5.3 g, 22.2 mmol) in dry THF (10 mL), cooled with a water bath, was added Super-Hydride® (1.0 M THF solution, 29.0 mmol, 29.0 mL) and the reaction mixture was allowed to stir at rt. After 1 h the mixture was cooled again (ice bath), slowly quenched with water (10 mL), the aqueous phase was saturated with $K_2CO_3$ and the reaction mixture was extracted with diethylether. The organic phase was dried over sodium sulfate, filtered and evaporated to give a crude product, which was taken up in ethyl acetate (200 mL) and filtered through a silica pad to give 197FBA17d as a colorless oil (4.11 g, 77%).

$^1$H-NMR (CDCl$_3$, 300 MHz) 4.19 (m, 2H), 2.18-2.12 (m, 2H), 1.95-1.89 (m, 4H), 1.66 (d, J=14.3, 2H), 1.46 (s, 9H), 1.17 (s, 3H).

Endo-3-exo-methyl-8-azabicyclo[3.2.1]octan-3-ol hydrochloride (197FBA20a)

To solution of 197FBA17d (3.81 g, 15.8 mmol) in diethylether (40 mL) was added a solution of HCl in dioxane (4 M, 40 mL). The reaction mixture was stirred during 2 h, then evaporated to give a white solid, which was filtered, washed with heptane (70 mL), and dried in vacuo to give 197FBA20a as a white solid (2.17 g, 77%).

$^1$H-NMR (DMSO-d$_6$, 300 MHz) δ 3.87 (br s, 2H), 2.27 (d, J=7.3, 2H), 2.00 (dd, J=14.9, 3.2, 2H), 1.87-1.83 (m, 2H), 1.74 (d, J=14.6, 2H), 1.07 (s, 3H).

4-(3-Endo-hydroxy-3-exo-methyl-8-azabicyclo[3.2.1]oct-8-yl)naphthalene-1-carbonitrile, hydrochloride (197FBA23a)

To a solution of 156AF70-267 (35 mg, 0.120 mmol) in dichloromethane (0.5 mL) was added a solution of HCl in dioxane (4 M, 0.15 mL), the mixture stirred during 30 min and then evaporated to give the title compound (38 mg, 100%) as a white solid.

LCMS m/z 293 [M+H]$^+$. $^1$H-NMR (DMSO-d$_6$, 300 MHz) δ 8.18 (d, J=8.0, 1H), 8.00 (d, J=8.3, 1H), 7.90 (d, J=8.1, 1H), 7.76-7.68 (m, 1H), 7.68-7.58 (m, 1H), 7.05 (d, J=8.2, 1H), 4.18-4.03 (m, 2H), 2.34-2.19 (m, 2H), 2.17-2.04 (m, 2H), 1.91-1.72 (m, 4H), 1.18 (s, 3H). $^{13}$C-NMR (DMSO-d$_6$, 75 MHz) 153.0, 134.3, 133.8, 128.9, 127.1, 126.4, 125.9, 125.0, 119.0, 111.4, 100.0, 67.7, 60.2, 45.3, 34.2, 26.4.

4-(3-Methyl-8-azabicyclo[3.2.1]oct-2-en-8-yl)naphthalene-1-carbonitrile (197FBA24c)

To a solution of 156AF70-267 (43 mg, 0.147 mmol) in dichloromethane (0.5 mL) was added aq. sulfuric acid (2 M, 0.15 mL), the reaction mixture stirred during 30 min. The solvent was removed to give a solid, which was washed several times with heptane and dichloromethane and dried. The crude was taken up in sat. aqueous NaHCO$_3$ and the water phase extracted twice with ethyl acetate. The combined organic phases were dried over sodium sulfate, filtered and evaporated to give a crude product which was purified by silica gel column chromatography using heptane/ethyl acetate (8:2) as the eluent, to give 197FBA24c (11 mg, 37%).

LCMS m/z 275 [M+H]$^+$. $^1$H-NMR (CDCl$_3$, 300 MHz) δ 8.14-8.05 (m, 2H), 7.65 (d, J=8.0, 1H), 7.58-7.51 (m, 1H), 7.49-7.40 (m, 1H), 6.91 (d, J=8.0, 1H), 5.80-5.70 (m, 1H), 4.43-4.33 (m, 1H), 3.97 (t, J=5.2, 1H), 2.39-2.14 (m, 2H), 2.11-1.87 (m, 2H), 1.78-1.56 (m, 2H), 1.53 (s, 3H). $^{13}$C-NMR (CDCl$_3$, 75 MHz) 162.7, 150.7, 134.4, 133.7, 131.9, 128.4, 127.6, 126.1, 125.5, 125.1, 119.4, 113.6, 102.2, 59.2, 58.5, 39.8, 34.7, 29.9, 22.7.

In Vitro Determination of Receptor Activity

Receptor Selection and Amplification (R-SAT) Assays. The functional receptor assay, Receptor Selection and Amplification Technology (R-SAT™), was used with minor modifications from the procedure described previously (Brann, M. R. U.S. Pat. No. 5,707,798, 1998) to screen compounds for efficacy at the Androgen AR receptor. Briefly, NIH3T3 cells were grown in roller bottles to 70-80% confluence. Cells were then transfected for 12-16 h with plasmid DNAs using Polyfect (Qiagen Inc.) as per the manufacturer's protocol. R-SAT assays were typically performed by transfecting 30 ug/bottle of receptor and 50 ug/bottle of β-galactosidase plasmid DNA. All receptor and helper constructs used were in mammalian expression vectors. Helpers are defined as signaling molecules that modulate both ligand-dependent and/or ligand-independent function of the AR receptor, typically co-activators. NIH3T3 cells were transfected for 12-16 h, then trypsinized and frozen in DMSO. Frozen cells were later thawed, plated at 10,000-40,000 cells per well of a 96 well plate containing drug. Cells were then grown in a humidified atmosphere with 5% ambient CO$_2$ for five days. Media was then removed from the plates and marker gene activity was measured by the addition of the β-galactosidase substrate o-nitrophenyl β-D-galactopyranoside (ONPG, in PBS with 5% NP-40). The resulting colorimetric reaction was measured in a spectrophotometric plate reader (Titertek Inc.) at 420 nM. All data were analyzed using the computer program XLFit (IDBSm).

Androgen Receptor Agonist Activity

TABLE 1

| compound | % Efficacy | pEC50 |
| --- | --- | --- |
| 196MBT2-7 | 85 | 8.1 |
| 116BG35-24 | 94 | 8.1 |
| 136BG73-10 | 66 | 8.1 |
| 136BG85-2 | 41 | 7.1 |
| 156AF70-267 | 88 | 8.7 |
| 156AF11-229 | 44 | 6.8 |
| 156AF32-246 | 57 | 7.4 |

Determination of In Vivo Activity of Test Compounds as Androgen Receptor Agonists 116BG33 Results Androgen Receptor agonist 116BG33 was administered s.c. daily for two weeks to castrated male Sprague Dawley rats (n=3). The effects of 116BG33 (3, 10, 30 mg/kg) were compared to testosterone propionate (0.1 and 1 mg/kg; positive control) and vehicle (10% Tween80; negative control). Blood and wet weights of prostate gland and seminal vesicle were measured after sacrifice that occurred 24 hours after the last dose. Blood was collected in heparin collection tubes after sacrifice that occurred 24 hours after the last dose. Blood was centrifuged and plasma collected and plasma samples frozen.

Rat luteinizing hormone (LH) plasma levels were determined using an enzyme linked immunoabsorbent assay (ELISA) from Amersham as per manufacturer's instructions. The solid phase assay is based on the competition between unlabeled rLH and a fixed quantity of biotin labelled rLH for a limited amount of rLH specific antibody. A conjugate streptavidin/peroxidase allows for signal amplification and detection in presence of the substrate.

Results

Figure 2:
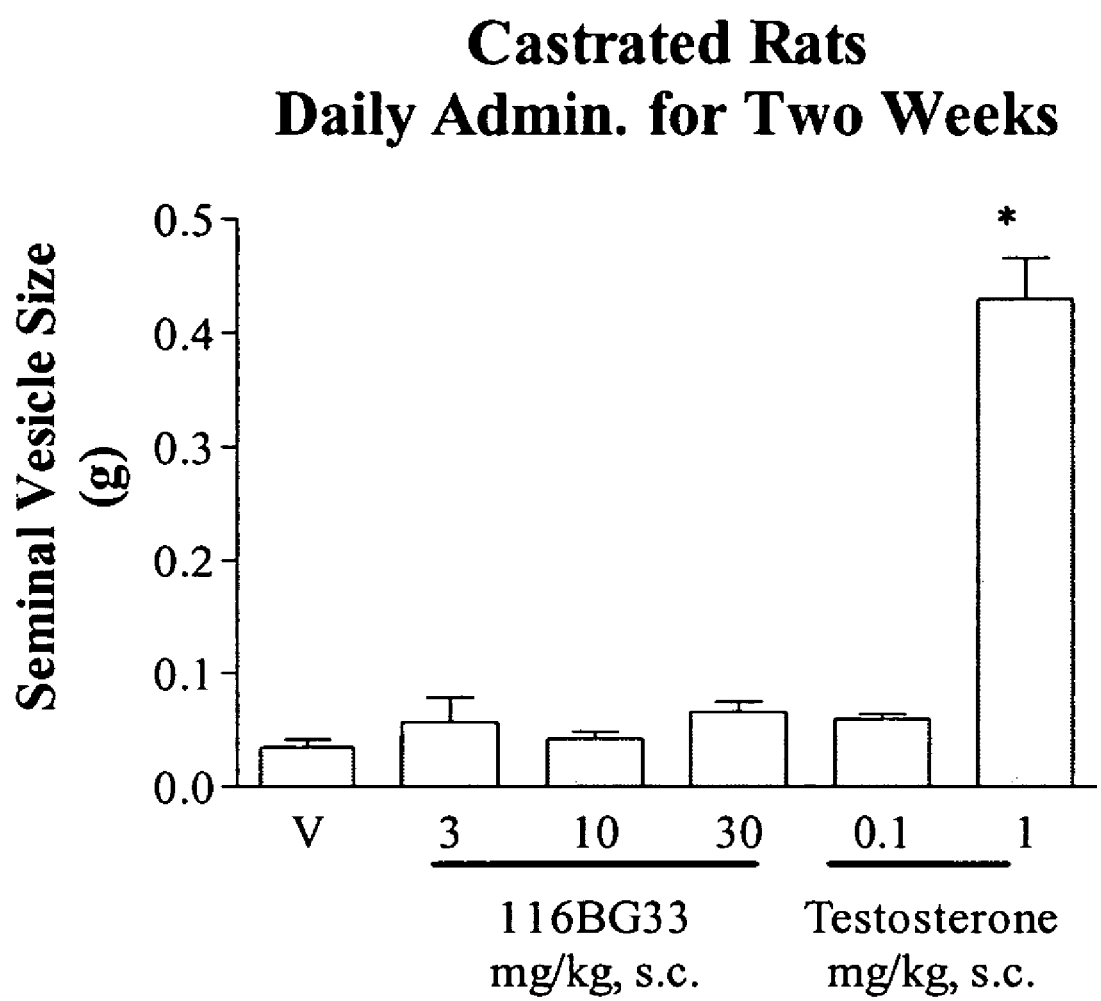
FIG. 2 shows the effect of daily subcutaneous administration for two weeks of 3, 10 or 30 mg/kg 116BG33 or 0.1 mg/kg testosterone propionate (TP) on wet weight of seminal vesicle.

Daily s.c. administration for two weeks of 3, 10 or 30 mg/kg 116BG33 or 0.1 mg/kg testosterone propionate (TP) did not have any effect on wet weight of prostate (FIG. 1) or seminal vesicle (FIG. 2) after sacrifice compared to vehicle. In contrast, daily s.c. administration for two weeks of 1 mg/kg testosterone propionate (TP) resulted in a significant increase in wet weight of prostate (FIG. 1) and seminal vesicle (FIG. 2) compared to vehicle. These results suggest that 116BG33 will not exhibit the potential side effect of increased seminal vesicle and prostate size that is common after treatment with testosterone.

Figure 3:
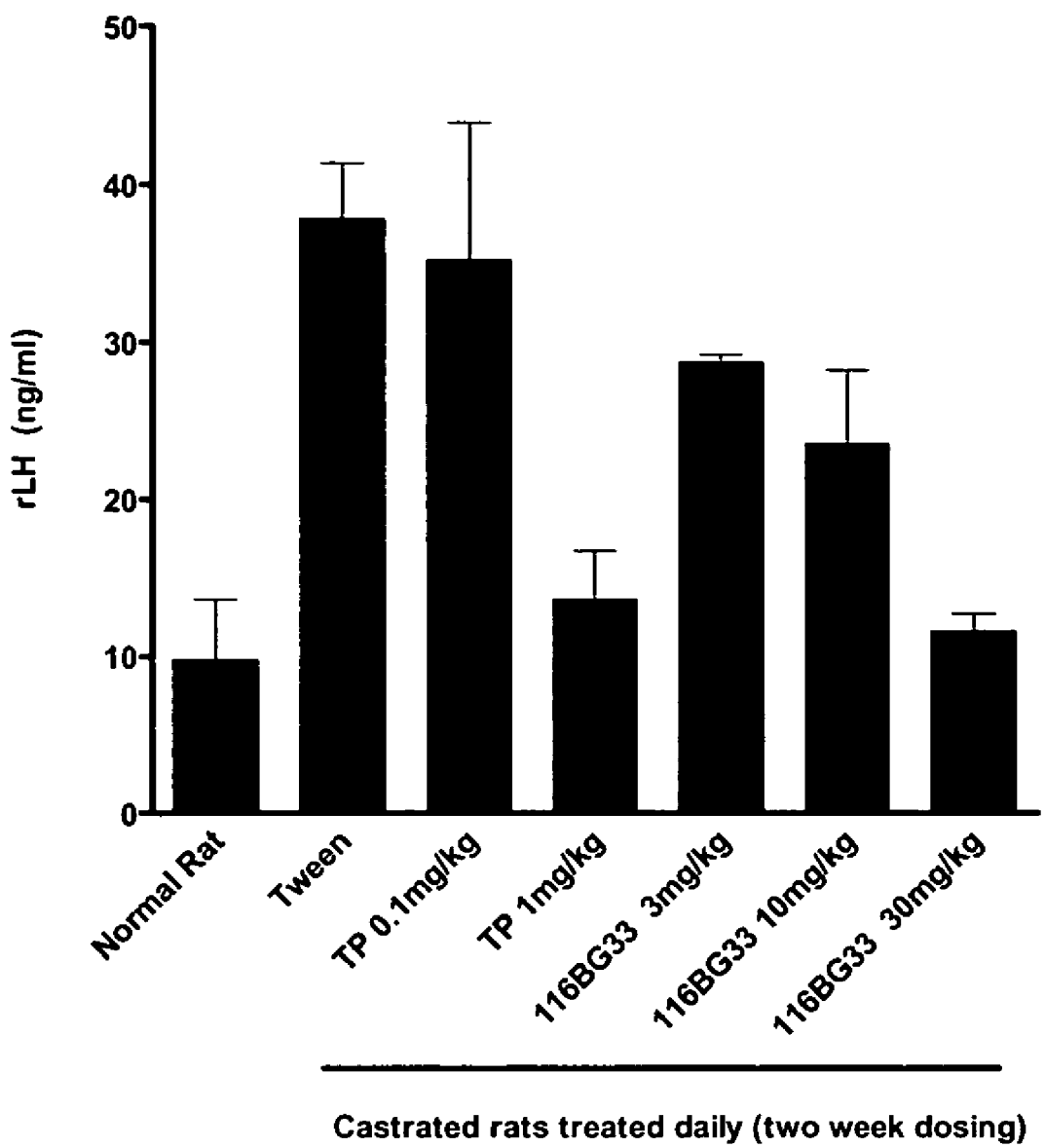
FIG. 3 shows that plasma levels of luteinizing hormone are increased by about 4-5 fold upon castration.

As shown in FIG. 3, upon castration, plasma levels of luteinizing hormone are increased by about 4-5 fold. Chronic exogeneous administration (14 days) of an AR agonist such as the testosterone propionate analog results in a dose dependent reversal of the LH levels to levels similat to naive (non-castrated animals). Sub-cutaneous administration of 116BG33, a potent and selective AR agonist, similarly reduces LH levels to physiological norms. Complete reversal is evident at 30 mg/kg.

154BG31 Results

Figure 4:
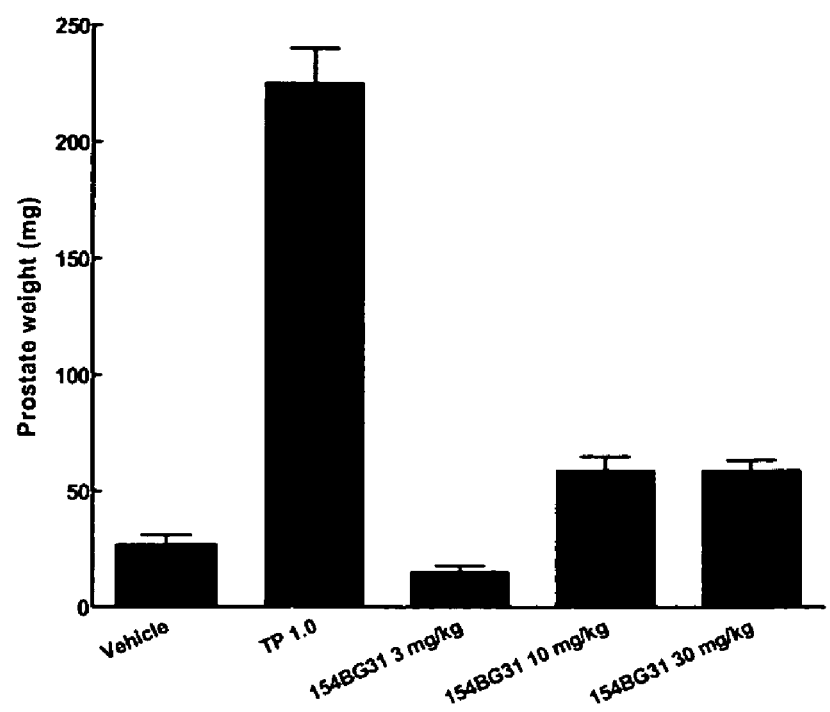
FIG. 4 shows the effect of daily subcutaneous administration of testosterone propionate (TP), at a dose of 1 mg/kg for a period of two weeks on wet tissue weights of prostate as compared to vehicle.
Figure 5:
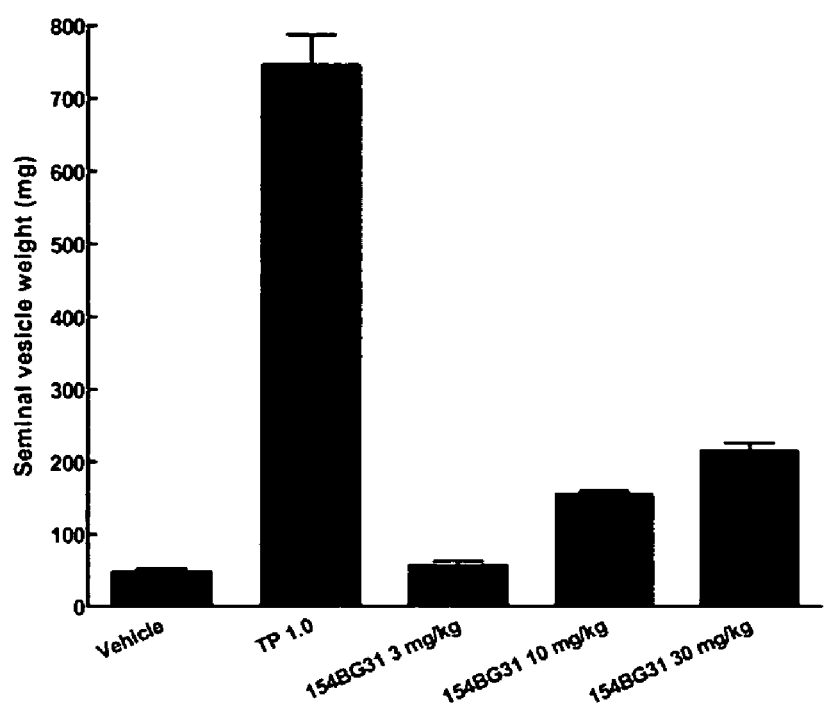
FIG. 5 shows the effect of daily subcutaneous administration of testosterone propionate (TP), at a dose of 1 mg/kg for a period of two weeks on wet tissue weights of seminal vesicle as compared to vehicle.
Figure 6:
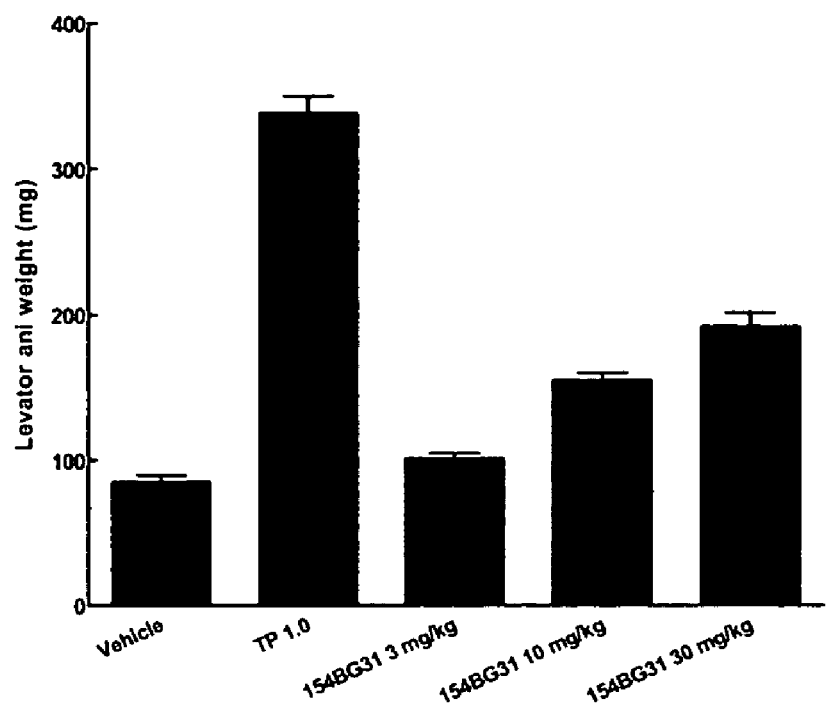
FIG. 6 shows the effect of daily subcutaneous administration of testosterone propionate (TP), at a dose of 1 mg/kg for a period of two weeks on wet tissue weights of levator ani muscle as compared to vehicle.
Figure 7:
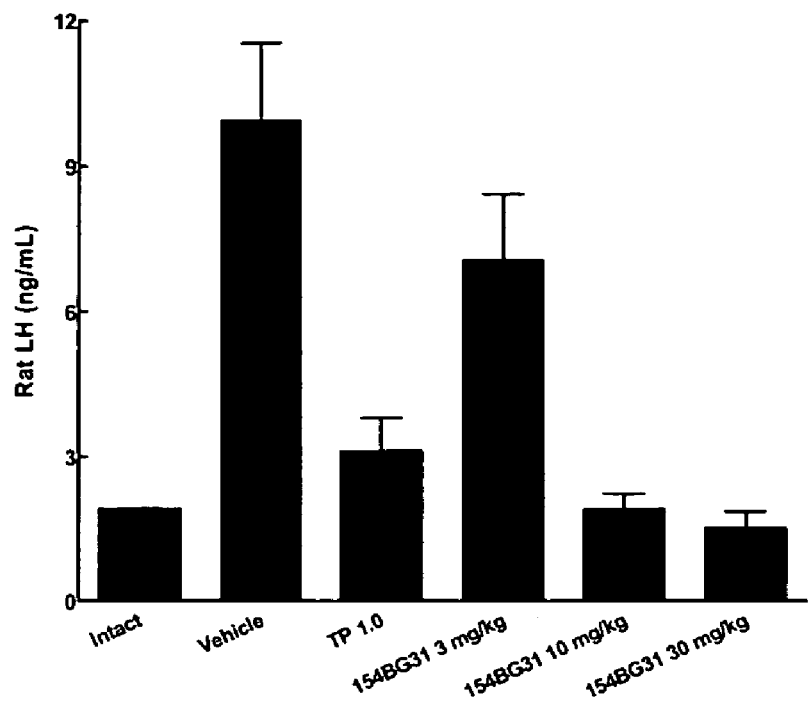
FIG. 7 shows that upon castration, plasma levels of luteinizing hormone (LH) increased by approximately 3-4 fold.

Daily subcutaneous (s.c.) administration of testosterone propionate (TP), at a dose of 1 mg/kg for a period of two weeks, produced significant increases in prostate (FIG. 4), seminal vesicle (FIG. 5), and levator ani muscle (FIG. 6) wet tissue weights as compared to vehicle treatment. In contrast, daily s.c. administration of 3 mg/kg 154BG31 for a period of two weeks did not appear to significantly alter wet tissue weights. Daily administration of higher doses (3 and 10 mg/kg) of 154BG31 appeared to significantly increase wet tissue weights, however, not to the extent of TP. These data suggest, as compared TP, the potential for negative side effects (i.e, increased seminal vesicle and prostate size) with 154BG31 may not be evident until doses of at least 100× of TP are reached. Upon castration, plasma levels of luteinizing hormone (LH) increased by approximately 3-4 fold. (FIG. 7) Chronic administration of TP (1 mg/kg, s.c. for 14 days), an AR agonist, restored LH levels to those obtained in naive rats (non-castrated animals). Daily administration of 154BG31 (various doses, s.c. for 14 days), a potent and selective AR agonist, produced a dose-dependent suppression of plasma LH levels, such that a complete reversal was evident at 10 mg/kg.

What is claimed is:

1. A compound represented by the Formula (I):

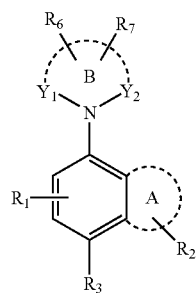

(I)

wherein $R_1$ and $R_2$ are each independently selected from the group consisting of hydrogen, lower alkyl, alkenyl, alkynyl, halo, nitro, cyano, hydroxy, amino, lower aminoalkyl, lower alkoxy, aryl, heteroaryl, $COOR_4$, $CONR_4R_5$, $NHCOR_4$, $NHSO_2R_4$, $OCOR_4$, $COR_4$, $SR_4$, $S(O)_nR_8$, $SO_2NR_8R_9$;

$R_3$ is selected from the group consisting of cyano, nitro, $S(O)_nR_8$, $SO_2NR_8R_9$, $OSO_2R_4$, $P(O)(OR_4)(OR_5)$, $P(O)(OH)(NR_4R_5)$, $PO(NR_4R_5)_2$, $COOR_4$;

ring A is a 6-membered, optionally aromatic, partially saturated or completely saturated carbocycle or heterocycle, containing up to two heteroatoms, selected from the group consisting of $NR_6R_7$, O, $SO_2$, S, C=O and C=S;

ring B is an optionally substituted tropane;

$Y_1$ and $Y_2$ are $CR_6R_7$;

$R_4$ and $R_5$ are each independently selected from the group consisting of hydrogen, cyano, optionally substituted alkyl, optionally substituted alkenyl, optionally substituted alkynyl, optionally substituted cycloalkyl, optionally substituted heterocyclylalkyl, optionally substituted arylalkyl, optionally substituted aryl, optionally substituted heteroarylalkyl, optionally substituted heteroaryl;

$R_6$ and $R_7$ are each independently selected from the group consisting of hydrogen, halo, cyano, hydroxy, optionally substituted alkyl, optionally substituted alkenyl, optionally substituted alkynyl, optionally substituted cycloalkyl, optionally substituted heterocyclylalkyl, optionally substituted arylalkyl, optionally substituted aryl, optionally substituted heteroarylalkyl, optionally substituted heteroaryl, $OR_4$, $NR_4R_5$, $SR_4$, $COR_4$, $COOR_4$, $CONR_4R_5$, $NHCOR_4$, $OCOR_4$, $CSR_4$, $CSOR_4$, $CSNR_4R_5$, $NHCSR_4$, $OCSR_4$, $S(O)_nR_4$, $SO_2NR_4R_5$, $OSO_2R_4$, $NHSO_2R_4$;

$R_8$ and $R_9$ are each independently selected from the group consisting of hydrogen, optionally substituted alkyl, optionally substituted alkenyl, optionally substituted alkynyl, optionally substituted cycloalkyl, optionally substituted heterocyclylalkyl, optionally substituted arylalkyl, optionally substituted heteroarylalkyl; and n is an integer from 1 to 3;

or pharmaceutically acceptable salts, amides, or stereoisomers thereof.

2. The compound of claim 1 wherein ring A is benzene, cyclohexyl or pyridine.

3. The compound of claim 1 wherein $R_3$ is cyano, nitro, $S(O)_nR_8$ or $SO_2NR_8R_9$.

4. The compound of claim 1 wherein $R_3$ is cyano or nitro.

5. The compound of claim 1, wherein ring B is optionally substituted with one or more groups selected from the group consisting of hydrogen, halogen, hydroxy, optionally substituted alkoxy, optionally substituted alkyl, optionally substituted alkenyl, optionally substituted alkynyl, optionally substituted aminoalkyl, and $NHCOR_4$.

6. The compound of claim 1, wherein ring B is optionally substituted with one or more hydroxy groups.

7. The compound of claim 1, wherein $R_6$ or $R_7$ is hydroxy or alkyl.

8. A compound selected from the group consisting of:
4-(3-endo-Hydroxy-8-azabicyclo[3.2.1]oct-8-yl)naphthalene-1-carbonitrile,
4-(3-Oxo-8-azabicyclo[3.2.1]oct-8-yl)naphthalene-1-carbonitrile,
4-{3-[2-(1H-Imidazol-4-yl)ethylamino]-8-azabicyclo[3.2.1]oct-8-yl}naphthalene-1-carbonitrile, dihydrochioride,
4-[3-(Cyclohexylmethylamino)-8-azabicyclo[3.2.1]oct-8-yl]naphthalene-1-carbonitrile, hydrochloride, 4-[3-(2-Morpholin-4-ylethylamino)-8-azabicyclo[3.2.1]oct-8-yl]naphthalene-1-carbonitrile, dihydrochloride, Methoxyacetic acid endo-8-(4-cyanonaphthalen-1-yl)-8-azabicyclo[3.2.1]oct-3-yl ester, 3-Morpholin-4-ylpropionic acid endo-8-(4-cyanonaphthalen-1-yl)-8-azabicyclo[3.2.1]oct-3-yl ester, hydrochloride, 3-(4-Ethylpiperazin-1-yl)propionic acid endo-8-(4-cyanonaphthalen-1-yl)-8-azabicyclo[3.2.1]oct-3-yl ester, hydrochloride, 3-Diethylaminopropionic acid endo-8-(4-cyanonaphthalen-1-yl)-8-azabicyclo[3.2.1]oct-3-yl ester, hydrochloride, Chloroacetic acid endo-8-(4-cyanonaphthalen-1-yl)-8-azabicyclo[3.2.1]oct-3-yl ester, Morpholin-4-ylacetic acid endo-8-(4-cyanonaphthalen-1-yl)-8-azabicyclo[3.2.1]oct-3-yl ester, hydrochloride, Imidazol-1-ylacetic acid endo-8-(4-cyanonaphthalen-1-yl)-8-azabicyclo[3.2.1]oct-3-yl ester, hydrochloride, (4-Ethylpiperazin-1-yl)acetic acid endo-8-(4-cyanonaphthalen-1-yl)-8-azabicyclo[3.2.1]oct-3-yl ester, dihydrochloride, Diethylaminoacetic acid endo-8-(4-cyanonaphthalen-1-yl)-8-azabicyclo[3.2.1]oct-3-yl ester, hydrochloride, Succinic acid mono endo-[8-(4-cyanonaphthalen-1-yl)-8-azabicyclo[3.2.1]oct-3-yl]ester, Trifluoroacetic acid endo-8-(4-cyanonaphthalen-1-yl)-8-azabicyclo[3.2.1]oct-3-yl ester, 4-(endo-3-Methoxy-8-azabicyclo[3.2.1]oct-8-yl)naphthalene-1-carbonitrile, N-[8-(4-Cyanonaphthalen-1-yl)-8-azabicyclo[3.2.1]oct-3-yl]-2-(4-ethylpiperazin-1-yl)acetamide, dihydrochloride, 4-(3-Endo-hydroxy-3-exo-methyl-8-azabicyclo[3.2.1]oct-8-yl)naphthalene-1-carbonitrile, 4-(3-endo-hydroxy-3-exo-propyl-8-azabicyclo[3.2.1]oct-8-yl)naphthalene-1-carbonitrile, 4-(endo-Spiro[8-azabicyclo[3.2.1]octane-3,2'-oxiran]-8-yl)naphthalene-1-carbonitrile, 4-(3-exo-Cyanomethyl-3-endo-hydroxy-8-azabicyclo[3.2.1]oct-8-yl)naphthalene-1-carbonitrile, 4-Nitrobenzoic acid exo-8-(4-cyanonaphthalen-1-yl)-8-azabicyclo[3.2.1]oct-3-yl ester, 4-(3-exo-Hydroxy-8-azabicyclo[3.2.1]oct-8-yl)naphthalene-1-carbonitrile, 4-(3-exo-Methoxy-8-azabicyclo[3.2.1]oct-8-yl)naphthalene-1-carbonitrile, 4-(8-Azabicyclo[3.2.1]oct-2-en-8-yl)naphthalene-1-carbonitrile, 4-(8-Azabicyclo[3.2.1]oct-8-yl)naphthalene-1-carbonitrile, 3-Pyrrolidin-1-yl-propionic acid endo-8-(4-cyanonaphthalen-1-yl)-8-azabicyclo[3.2.1]oct-3-yl ester, fumarate, 3-Imidazol-1-yl-propionic acid endo-8-(4-cyanonaphthalen-1-yl)-8-azabicyclo[3.2.1]oct-3-yl ester, fumarate, 3-Pyrazol-1-yl-propionic acid endo-8-(4-cyano-naphthalen-1-yl)-8-azabicyclo[3.2.1]oct-3-yl ester, fumarate, 4-(2-Methyl-8-azabicyclo[3.2.1]oct-8-yl)naphthalene-1-carbonitrile, Endo-8-(4-cyanonaphthalen-1-yl)-8-azabicyclo[3.2.1]oct-3-yl dihydrogen phosphate, 4-(7-Azabicyclo[2.2.1]hept-7-yl)naphthalene-1-carbonitrile hydrochloride, 2-exo-[8-(4-Cyanonaphthalen-1-yl)-3-endo-hydroxy-8-azabicyclo[3.2.1]oct-3-yl]-N,N-dimethylethanesulfonamide, 4-(3-Endo-hydroxy-3-exo-methyl-8-azabicyclo[3.2.1]oct-8-yl)naphthalene-1-carbonitrile, hydrochloride, 4-(3-Methyl-8-azabicyclo[3.2.1]oct-2-en-8-yl)naphthalene-1-carbonitrile, 3-Piperazin-1-ylpropionic acid endo-8-(4-cyanonaphthalen-1-yl)-8-azabicyclo[3.2.1]oct-3-yl ester, dihydrochloride, 3-[Bis(2-hydroxyethyl)amino]propionic acid endo-8-(4-cyanonaphthalen-1-yl)-8-azabicyclo[3.2.1]oct-3-yl ester, fumarate, 3-(3-Dimethylaminopyrrolidin-1-yl)propionic acid endo-8-(4-cyanonaphthalen-1-yl)-8-azabicyclo[3.2.1]oct-3-yl ester, difumarate, 3-(4-Methylpiperazin-1-yl)propionic acid endo-8-(4-cyanonaphthalen-1-yl)-8-aza-bicyclo[3.2.1]oct-3-yl ester, difumarate, and 4-(3-Diethylaminomethyl-3-hydroxy-8-azabicyclo[3.2.1]oct-8-yl)naphthalene-1-carbonitrile, hydrochloride.

9. A compound selected from the group consisting of:

4-(3-endo-Hydroxy-8-azabicyclol[3.2.1]oct-8-yl)naphthalene-1-carbonitrile, 3-(4-Ethylpiperazin-1-yl)propionic acid endo-8-(4-cyanonaphthalen-1-yl)-8-azabicyclo[3.2.1]oct-3-yl ester, hydrochloride, 3-Diethylaminopropionic acid endo-8-(4-cyanonaphthalen-1-yl)-8-azabicyclo[3.2.1]oct-3-yl ester, hydrochloride, 4-(3-Endo-hydroxy-3-exo-methyl-8-azabicyclo[3.2.1]oct-8-yl)naphthalene-1-carbonitrile, 4-(3-endo-hydroxy-3-exo-propyl-8-azabicyclo[3.2.1]oct-8-yl)naphthalene-1-carbonitrile, 4-(endo-Spiro[8-azabicyclo[3.2.1]octane-3,2'-oxiran]-8-yl)naphthalene-1-carbonitrile, 4-(8-Azabicyclo[3.2.1]oct-2-en-8-yl)naphthalene-1-carbonitrile, 4-(8-Azabicyclo[3.2.1]oct-8-yl)naphthalene-1-carbonitrile, 4-(2-Methyl-8-azabicyclo[3.2.1]oct-8-yl)naphthalene-1-carbonitrile, 4-(3-Endo-hydroxy-3-exo-methyl-8-azabicyclo[3.2.1]oct-8-yl)naphthalene-1-carbonitrile, hydrochloride, and 4-(3-Methyl-8-azabicyclo[3.2.1]oct-2-en-8-yl)naphthalene-1-carbonitrile.

10. A compound selected from the group consisting of:

4-(3-Propylamino-8-azabicyclo[3.2.1]oct-8-yl)naphthalene-1-carbonitrile, hydrochloride, 4-(3-Dimethylamino-8-azabicyclo[3.2.1]oct-8-yl)naphthalene-1-carbonitrile, hydrochloride, 4-[3-(3-Hydroxypropylamino)-8-azabicyclo[3.2.1]oct-8-yl]naphthalene-1-carbonitrile, hydrochloride, 4-[3-(2-Ethoxyethylamino)-8-azabicyclo[3.2.1]oct-8-yl]naphthalene-1-carbonitrile, hydrochloride, 4-(3-Cyclopropylamino-8-azabicyclo[3.2.1]oct-8-yl)naphthalene-1-carbonitrile, hydrochloride, 4-[3-(2-Dimethylaminoethylamino)-8-azabicyclo[3.2.1]oct-8-yl]naphthalene-1-carbonitrile, dihydrochloride, 4-{3-[(Furan-2-ylmethyl)amino]-8-azabicyclo[3.2.1]oct-8-yl}naphthalene-1-carbonitrile, hydrochloride, 4-{3-[(Pyridin-2-ylmethyl)amino]-8-azabicyclo[3.2.1]oct-8-yl}naphthalene-1-carbonitrile, dihydrochloride, 4-[3-(2-Isopropoxyethylamino)-8-azabicyclo[3.2.1]oct-8-yl]naphthalene-1-carbonitrile, hydrochloride, 4-(1,4-Dioxa-8-azaspiro[4.5]dec-8-yl)naphthalene-1-carbonitrile, 4-(3-Hydroxyimino-8-azabicyclo[3.2.1]oct-8-yl)naphthalene-1-carbonitrile, 3-Chloropropionic acid endo-8-(4-cyanonaphthalen-1-yl)-8-azabicyclo[3.2.1]oct-3-yl ester,
4-(3-exo-Ethynyl-3-endo-hydroxy-8-azabicyclo[3.2.1]oct-8-yl)naphthalene-1-carbonitrile,
4-[3-(2-[1,3]Dioxan-2-ylethyl)-3-hydroxy-8-azabicyclo[3.2.1]oct-8-yl]naphthalene-1-carbonitrile,
4-(3-Amino-8-azabicyclo[3.2.1]oct-8-yl)naphthalene-1-carbonitrile, hydrochloride,
2-Chloro-N-[8-(4-cyanonaphthalen-1-yl)-8-azabicyclo[3.2.1]oct-3-yl]acetamide, hydrochloride,
N-[8-(4-Cyanonaphthalen-1-yl)-8-azabicyclo[3.2.1]oct-3-yl]-2-diethylaminoacetamide, hydrochloride,
2-Cyanoethyl endo-8-(4-cyanonaphthalen-1-yl)-8-azabicyclo[3.2.1]oct-3-yl N,N-diisopropylamidophosphate,
Endo-8-(4-cyanonaphthalen-1-yl)-8-azabicyclo[3.2.1]oct-3-yl hydrogen N,N-diisopropylamidophosphate,
[8-(4-Cyanonaphthalen-1-yl)-8-azabicyclo[3.2.1]oct-3-yl]urea,
Dimethylcarbamic acid endo-8-(4-cyanonaphthalen-1-yl)-8-azabicyclo[3.2.1]oct-3-yl ester,
4-[3-exo-(4-ethylpiperazin-1-yl methyl)-3-endo-hydroxy-8-azabicyclo[3.2.1]oct-8-yl]naphthalene-1-carbonitrile,
4-(3-endo-hydroxy-3-exo-hydroxymethyl-8-azabicyclo[3.2.1]oct-8-yl)naphthalene-1-carbonitrile,
4-(3-endo-Hydroxy-3-exo-{[2-(1H-imidazol-4yl)ethylamino]methyl}-8-azabicyclo[3.2.1]oct-8-yl)naphthalene-1-carbonitrile,
4-(3-endo-Hydroxy-3-exo-methoxymethyl-8-azabicyclo[3.2.1]oct-8-yl)naphthalene-1-carbonitrile,
Acrylic acid endo-8-(4-cyanonaphthalen-1-yl)-8-azabicyclo[3.2.1]oct-3-yl ester,
4-(2-Methyl-3-oxo-8-azabicyclo[3.2.1]oct-8-yl)naphthalene-1-carbonitrile,
4-(3-exo-Benzyl-3-endo-hydroxy-8-azabicyclo[3.2.1]oct-8-yl)naphthalene-1-carbonitrile,
8-(4-Cyanonaphthalen-1-yl)-8-azabicyclo[3.2.1]oct-2-ene-2-carboxylic acid methyl ester,
8-(4-Cyanonaphthalen-1-yl)-8-azabicyclo[3.2.1]octane-2-carboxylic acid methyl ester,
4-(2-Hydroxymethyl-8-azabicyclo[3.2.1]oct-2-en-8-yl)naphthalene-1-carbonitrile,
(1R,2R,3S,5S)-3-Benzoyloxy-8-(4-cyanonaphthalen-1-yl)-8-azabicyclo[3.2.1]octane-2-carboxylic acid methyl ester,
(1R,2R,3S,5S)-4-(3-Hydroxy-2-hydroxymethyl-8-azabicyclo[3.2.1]oct-8-yl)naphthalene-1-carbonitrile,
2-Cyanoethyl endo-8-(4-cyanonaphthalen-1-yl)-8-azabicyclo[3.2.1]oct-3-yl N,N-diisopropylamidophosphite,
2-Cyanoethyl endo-8-(4-cyanonaphthalen-1-yl)-8-azabicyclo[3.2.1]oct-3-yl diisopropylamidophosphate,
2-Cyanoethyl ethyl endo-8-(4-cyanonaphthalen-1-yl)-8-azabicyclo[3.2.1]oct-3-yl phosphate,
Ethyl endo-8-(4-cyanonaphthalen-1-yl)-8-azabicyclo[3.2.1]oct-3-yl hydrogen phosphate,
Bis(2-cyanoethyl) endo-8-(4-cyanonaphthalen-1-yl)-8-azabicyclo[3.2.1]oct-3-yl phosphate,
2-Cyanoethyl endo-8-(4-cyanonaphthalen-1-yl)-8-azabicyclo[3.2.1]oct-3-yl phenyl phosphate,
Endo-8-(4-cyanonaphthalen-1-yl)-8-azabicyclo[3.2.1]oct-3-yl phenyl hydrogen phosphate,
N-[8-(4-cyanonaphthalen-1-yl)-8-azabicyclo[3.2.1]oct-3-yl]acetamide,
3-Chloro-N-[8-(4-cyanonaphthalen-1-yl)-8-azabicyclo[3.2.1]oct-3-yl]propanamide,
N-[8-(4-cyanonaphthalen-1-yl)-8-azabicyclo[3.2.1]oct-3-yl]-3-(4-ethylpiperazin-1-yl)propanamide, dihydrochloride,
N-[8-(4-Cyanonaphthalen-1-yl)-8-azabicyclo[3.2.1]oct-3-yl]-3-diethylaminopropionamide, hydrochloride,
N-[8-(4-cyanonaphthalen-1-yl)-8-azabicyclo[3.2.1]oct-3-yl]-3-(1H-imidazol-1-yl)propanamide hydrochloride,
N-[8-(4-Cyanonaphthalen-1-yl)-8-azabicyclo[3.2.1]oct-3-yl]-2-(ethoxyethoxy)acetamide,
N'-[8-(4-cyanonaphthalen-1-yl)-8-azabicyclo[3.2.1]oct-3-yl]-4-methylbenzenesulfonylhydrazone, and
3-exo-[8-(4-Cyanonaphthalen-1-yl)-3-endo-hydroxy-8-azabicyclo[3.2.1]oct-3-yl]-N,N-dimethylpropanamide.

* * * * *